(12) United States Patent
Yasuma et al.

(10) Patent No.: US 7,820,837 B2
(45) Date of Patent: Oct. 26, 2010

(54) CONDENSED RING COMPOUND

(75) Inventors: Tsuneo Yasuma, Osaka (JP); Nobuyuki Negoro, Osaka (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 243 days.

(21) Appl. No.: 10/558,846

(22) PCT Filed: May 28, 2004

(86) PCT No.: PCT/JP2004/007770

§ 371 (c)(1),
(2), (4) Date: Nov. 30, 2005

(87) PCT Pub. No.: WO2004/106276

PCT Pub. Date: Dec. 9, 2004

(65) Prior Publication Data

US 2006/0258722 A1 Nov. 16, 2006

(30) Foreign Application Priority Data

May 30, 2003 (JP) ............................. 2003-153986
May 7, 2004 (JP) ............................. 2004-139144

(51) Int. Cl.
*C07D 311/00* (2006.01)
*C07D 333/00* (2006.01)
*C07D 277/60* (2006.01)

(52) U.S. Cl. .................... 549/407; 549/49; 548/152
(58) Field of Classification Search ................ 549/407, 549/49; 548/152
See application file for complete search history.

(56) References Cited

U.S. PATENT DOCUMENTS

| | | | |
|---|---|---|---|
| 6,875,780 B2 * | 4/2005 | Auerbach et al. ............ | 514/345 |
| 7,244,763 B2 * | 7/2007 | Bratton et al. .............. | 514/532 |
| 2002/0103242 A1 | 8/2002 | Sahoo et al. | |
| 2004/0058965 A1 | 3/2004 | Momose et al. | |

FOREIGN PATENT DOCUMENTS

| | | |
|---|---|---|
| EP | 1 398 313 | 3/2004 |
| EP | 1 535 915 | 6/2005 |
| EP | 1535915 A1 | 6/2005 |
| EP | 1559422 A1 | 8/2005 |
| JP | 2001-122817 | 5/2001 |
| WO | 98/00403 | 1/1998 |
| WO | WO 98/38156 | 9/1998 |
| WO | WO 99/11255 | 3/1999 |
| WO | WO 99/11255 A1 * | 3/1999 |
| WO | WO 00/64876 | 11/2000 |
| WO | WO 01/47859 A1 | 7/2001 |
| WO | 01/66098 | 9/2001 |
| WO | 02/00633 | 1/2002 |
| WO | 02/26729 | 4/2002 |
| WO | WO02/053547 A1 | 7/2002 |
| WO | WO 02/057783 A2 | 7/2002 |
| WO | WO 02/083616 * | 10/2002 |
| WO | WO 03/011842 A1 | 2/2003 |
| WO | WO 03/074051 A1 | 9/2003 |
| WO | WO 03/089418 A1 | 10/2003 |
| WO | WO 03/099793 A1 | 12/2003 |
| WO | WO 2004/010936 A2 | 2/2004 |
| WO | WO 2004/011446 A1 | 2/2004 |
| WO | 2004/019869 | 3/2004 |
| WO | WO 2004/022551 A1 | 3/2004 |
| WO | WO 2004/041266 A1 | 5/2004 |
| WO | 2004/058174 | 7/2004 |
| WO | 2004/082601 | 9/2004 |
| WO | 2004/091604 | 10/2004 |
| WO | 2004/098498 | 11/2004 |
| WO | WO 2005/087710 A1 | 9/2005 |
| WO | 2005/115384 | 12/2005 |

OTHER PUBLICATIONS

Supplementary European Search Report issued Aug. 21, 2009 in connection with corresponding European Applicant No. 04 74 5580.

* cited by examiner

*Primary Examiner*—D. Margaret Seaman
*Assistant Examiner*—Nizal S Chandrakumar
(74) *Attorney, Agent, or Firm*—Wenderoth, Lind & Ponack, L.L.P.

(57) ABSTRACT

The present invention aims at providing a novel fused ring compound having a GPR40 receptor function modulating action and being useful as an insulin secretagogue or a pharmaceutical agent for the prophylaxis or treatment of diabetes, more particularly, a compound represented by the formula:

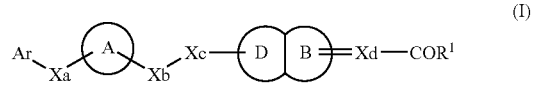

wherein Ar is an optionally substituted cyclic group,
ring A is a ring optionally further substituted (provided that the ring is not thiazole, oxazole, imidazole and pyrazole),
Xa and Xb are each independently a bond or a spacer having a main chain of 1 to 5 atom(s),
Xc is O, S, SO or SO$_2$,

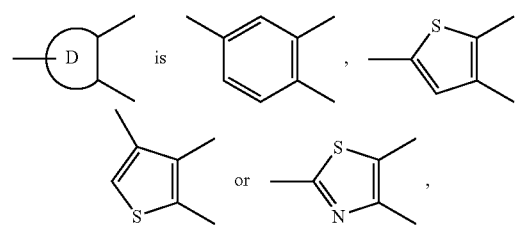

ring B is a 5- to 7-membered ring,
Xd is a bond, CH or CH$_2$,
-----is a single bond when Xd is a bond or CH$_2$, or a double bond when Xd is CH, and
R$^1$ is an optionally substituted hydroxy group, and a salt thereof.

7 Claims, No Drawings

CONDENSED RING COMPOUND

This application is the National Phase filing of International Patent Application No. PCT/JP2004/007770, filed May 28, 2004.

TECHNICAL FIELD

The present invention relates to a novel fused ring compound having a GPR40 receptor function modulating action.

BACKGROUND ART

An amino acid sequence of GPR40 derived from human and a DNA encoding same are described (WO2000/22129 and Biochem Biophys Res Commun. 1997, Oct. 20; 239(2)).

A carboxylic acid having an aromatic ring and a derivative thereof are known to have various physiological activities.

There are known alkanoic acid derivatives (JP-A-2002-265457).

There are known isoxazole derivatives having an insulin secretion promoting action and a hypoglycemic action and being useful for the prophylaxis or treatment of diabetes and the like (JP-A-2002-212171).

There are known nitrogen-containing 5-membered heterocyclic compounds having a hypoglycemic action and a hypolipidemic action and being useful for the prophylaxis or treatment of diabetes and the like (JP-A-2001-226350).

There are known alkoxyiminoalkanoic acid derivatives having a hypoglycemic action and a hypolipidemic action and being useful for the prophylaxis or treatment of diabetes and the like (JP-A-2001-199971).

There are known oxyiminoalkanoic acid derivatives having a hypoglycemic action and a hypolipidemic action and being useful for the prophylaxis or treatment of diabetes and the like (JP-A-2000-198772).

There are known 1,3-azole derivatives having a retinoid-related receptor function regulating action and being useful for the prophylaxis or treatment of diabetic complications and the like (JP-A-2000-80086).

There are known oxyiminoalkanoic acid derivatives having a hypoglycemic action and a hypolipidemic action and being useful for the prophylaxis or treatment of diabetes and the like (JP-A-2000-34266).

There are known oxazole derivatives having an insulin secretion promoting action and a hypoglycemic action and being useful for the prophylaxis or treatment of diabetes and the like (JP-A-09-323983).

There are known benzofuran derivatives having a hypoglycemic and hypolipidemic action (JP-A-08-311065).

It has been reported that fatty acid binds to GPR40 (WO02/057783).

DISCLOSURE OF THE INVENTION

The present invention aims at providing a novel fused ring compound having a GPR40 receptor function modulating action and being useful as an insulin secretagogue or a pharmaceutical agent for the prophylaxis or treatment of diabetes and the like.

The present inventors have intensively conducted various studies and found that the compound represented by the following formula (I) unexpectedly has a superior GPR40 receptor agonist activity, shows superior properties as a pharmaceutical product such as stability and the like, based on its specific chemical structure, and can be a safe and useful pharmaceutical agent for the prophylaxis or treatment of GPR40 receptor related disease state or diseases in mammal, and, based on these findings, completed the present invention.

Accordingly, the present invention relates to

[1] a compound represented by the formula:

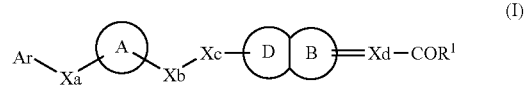

(I)

wherein Ar is an optionally substituted cyclic group,
ring A is a ring optionally further substituted (provided that the ring is not thiazole, oxazole, imidazole and pyrazole),
Xa and Xb are each independently a bond or a spacer having a main chain of 1 to 5 atom(s),
Xc is O, S, SO or $SO_2$,

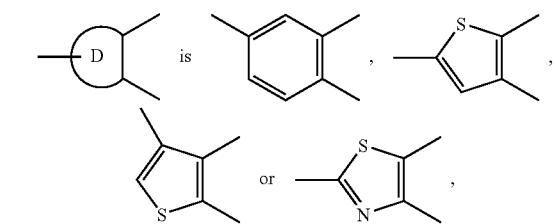

ring B is a 5- to 7-membered ring,
Xd is a bond, CH or $CH_2$,
----- is a single bond when Xd is a bond or $CH_2$, or a double bond when Xd is CH,
$R^1$ is an optionally substituted hydroxy group, provided that
(i) when ring A is benzene, the cyclic group represented by Ar is not a quinolinyl group,
(ii) when ring B is a 5- to 7-membered aromatic ring, the ring represented by ring A is not thiophene and furan,
(iii) when ring B is benzene, the ring represented by ring A is not 5-membered aromatic heterocycle, and
(iv) when ring B is cyclohexane, Xd is not a bond, provided that
[6-(4-biphenylyl)methoxy-2-tetralin]acetic acid;
methyl [6-(4-biphenylyl)methoxy-2-tetralin]acetate;
[7-(4-biphenylyl)methoxy-1,2,3,4-tetrahydro-2-oxo-3-quinoline]acetic acid; and
methyl [7-(4-biphenylyl)methoxy-1,2,3,4-tetrahydro-2-oxo-3-quinoline]acetate are excluded,
or a salt thereof (hereinafter sometimes to be abbreviated as compound (I));
[2] a prodrug of compound (I);
[3] compound (I) wherein the cyclic group represented by Ar is an aromatic hydrocarbon group;
[4] compound (I) wherein Xa is a bond;
[5] compound (I) wherein ring A is benzene;
[6] compound (I) wherein Xb is —$CH_2$—;
[7] compound (I) wherein Xc is O;
[8] compound (I) wherein

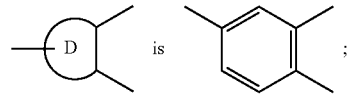

[9] compound (I) wherein ring B is a 5- to 7-membered non-aromatic ring;

[10] compound of the aforementioned [9], wherein ring B is cyclopentane or tetrahydrofuran;

[11] compound (I) wherein Xd is $CH_2$;

[12] compound (I) wherein $R^1$ is a hydroxy group;

[13] compound (I) represented by the formula:

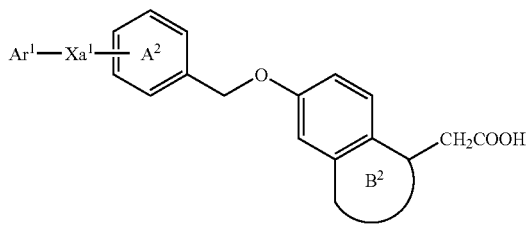

(I-2)

wherein $Ar^1$ is an optionally substituted phenyl group or optionally substituted indanyl group, $Xa^1$ is a bond or a spacer having a main chain of 1 to 5 atom(s), ring $A^2$ is a benzene ring optionally further substituted, and ring $B^2$ is a 5- to 7-membered ring;

[14] compound (I) represented by the formula:

(I-4)

wherein $Ar^2$ is an optionally substituted thiazolyl group, $Xa^2$ is a bond or a spacer having a main chain of 1 to 5 atom(s), ring $A^3$ is a benzene ring optionally further substituted, and ring $B^2$ is a 5- to 7-membered ring;

[15] a pharmaceutical agent comprising compound (I) or a prodrug thereof;

[16] a pharmaceutical agent of the aforementioned [15], which is an agent for the prophylaxis or treatment of diabetes;

[17] an insulin secretagogue comprising compound (I) or a prodrug thereof;

[18] a GPR40 receptor function modulator comprising a compound represented by the formula:

(I')

wherein ring $A^1$ is an optionally substituted ring,

Xb is a bond or a spacer having a main chain of 1 to 5 atom(s),

Xc is O, S, SO or $SO_2$,

ring $B^1$ is a 5- to 7-membered non-aromatic ring,

Xd is a bond, CH or $CH_2$,

------ is a single bond when Xd is a bond or $CH_2$, or a double bond when Xd is CH, and $R^1$ is an optionally substituted hydroxy group, or a salt thereof (hereinafter sometimes to be abbreviated as compound (I')), or a prodrug thereof;

[19] a method of modulating a GPR40 receptor function in a mammal, which comprises administering an effective amount of compound (I') or a prodrug thereof to the mammal; and

[20] use of compound (I') or a prodrug thereof for the production of a GPR40 receptor function modulator.

DETAILED DESCRIPTION OF THE INVENTION

Unless otherwise specified, as the "halogen atom" in the present specification, fluorine atom, chlorine atom, bromine atom and iodine atom can be mentioned.

Unless otherwise specified, as the "optionally substituted hydrocarbon group" in the present specification, for example, "optionally substituted $C_{1-6}$ alkyl group", "optionally substituted $C_{2-6}$ alkenyl group", "optionally substituted $C_{2-6}$ alkynyl group", "optionally substituted $C_{3-8}$ cycloalkyl group", "optionally substituted $C_{6-14}$ aryl group", "optionally substituted $C_{7-16}$ aralkyl group" and the like can be mentioned.

Unless otherwise specified, as the "$C_{1-6}$ alkyl group" in the present specification, for example, methyl, ethyl, propyl, isopropyl, butyl, isobutyl, sec-butyl, tert-butyl, pentyl, isopentyl, neopentyl, hexyl and the like can be mentioned.

Unless otherwise specified, as the "$C_{2-6}$ alkenyl group" in the present specification, for example, vinyl, propenyl, isopropenyl, 2-buten-1-yl, 4-penten-1-yl, 5-hexen-1-yl and the like can be mentioned.

Unless otherwise specified, as the "$C_{2-6}$ alkynyl group" in the present specification, for example, 2-butyn-1-yl, 4-pentyn-1-yl, 5-hexyn-1-yl and the like can be mentioned.

Unless otherwise specified, as the "$C_{3-8}$ cycloalkyl group" in the present specification, for example, cyclopropyl, cyclobutyl, cyclopentyl, cyclohexyl and the like can be mentioned.

Unless otherwise specified, as the "$C_{6-14}$ aryl group" in the present specification, for example, phenyl, 1-naphthyl, 2-naphthyl, 2-biphenylyl, 3-biphenylyl, 4-biphenylyl, 2-anthryl and the like can be mentioned. The $C_{6-14}$ aryl may be optionally saturated partially, and as the partially saturated $C_{6-14}$ aryl, for example, tetrahydronaphthyl and the like can be mentioned.

Unless otherwise specified, as the "$C_{7-16}$ aralkyl group" in the present specification, for example, benzyl, phenethyl, diphenylmethyl, 1-naphthylmethyl, 2-naphthylmethyl, 2,2-diphenylethyl, 3-phenylpropyl, 4-phenylbutyl, 5-phenylpentyl, 2-biphenylylmethyl, 3-biphenylylmethyl, 4-biphenylylmethyl and the like can be mentioned.

Unless otherwise specified, as the "optionally substituted hydroxy group" in the present specification, for example, "hydroxy group", "optionally substituted $C_{1-10}$ alkoxy group", "optionally substituted heterocyclyloxy group", "optionally substituted $C_{6-14}$ aryloxy group", "optionally substituted $C_{7-16}$ aralkyloxy group" and the like can be mentioned.

Unless otherwise specified, as the "$C_{1-6}$ alkoxy group" in the present specification, for example, methoxy, ethoxy, propoxy, isopropoxy, butoxy, isobutoxy, tert-butoxy, pentyloxy, hexyloxy and the like can be mentioned. As the "$C_{1-10}$ alkoxy group" in the present specification, heptyloxy, octyloxy, nonyloxy, decyloxy and the like can be mentioned besides the above-mentioned $C_{1-6}$ alkoxy group.

Unless otherwise specified, as the "$C_{1-6}$ alkoxy-$C_{1-6}$ alkoxy group" in the present specification, for example, methoxymethoxy, methoxyethoxy, ethoxymethoxy, ethoxyethoxy and the like can be mentioned.

As the "heterocyclyloxy group" in the present specification, hydroxy group substituted by a "heterocyclic group" below can be mentioned. As preferable examples of the heterocyclyloxy group, tetrahydropyranyloxy, thiazolyloxy, pyridyloxy, pyrazolyloxy, oxazolyloxy, thienyloxy, furyloxy and the like can be mentioned.

Unless otherwise specified, as the "$C_{6-14}$ aryloxy group" in the present specification, for example, phenoxy, 1-naphthyloxy, 2-naphthyloxy and the like can be mentioned.

Unless otherwise specified, as the "$C_{7-16}$ aralkyloxy group" in the present specification, for example, benzyloxy, phenethyloxy and the like can be mentioned.

Unless otherwise specified, as the "optionally substituted mercapto group" in the present specification, for example, "mercapto group", "optionally substituted $C_{1-10}$ alkylthio group", "optionally substituted heterocyclylthio group", "optionally substituted $C_{6-14}$ arylthio group", "optionally substituted $C_{7-16}$ aralkylthio group" and the like can be mentioned.

Unless otherwise specified, as the "$C_{1-6}$ alkylthio group" in the present specification, for example, methylthio, ethylthio, propylthio, isopropylthio, butylthio, sec-butylthio, tert-butylthio and the like can be mentioned. As the "$C_{1-10}$ alkylthio group" in the present specification, heptylthio, octylthio, nonylthio, decylthio and the like can be mentioned besides the above-mentioned $C_{1-6}$ alkylthio group.

Unless otherwise specified, as the "heterocyclylthio group" in the present specification, mercapto group substituted by a "heterocyclic group" below can be mentioned. As preferable examples of the heterocyclylthio group, tetrahydropyranylthio, thiazolylthio, pyridylthio, pyrazolylthio, oxazolylthio, thienylthio, furylthio and the like can be mentioned.

Unless otherwise specified, as the "$C_{6-14}$ arylthio group" in the present specification, for example, phenylthio, 1-naphthylthio, 2-naphthylthio and the like can be mentioned.

Unless otherwise specified, as the "$C_{7-16}$ aralkylthio group" in the present specification, for example, benzylthio, phenethylthio and the like can be mentioned.

Unless otherwise specified, as the "heterocyclic group" in the present specification, for example, a 5- to 14-membered (monocyclic, bicyclic or tricyclic) heterocyclic group containing 1 to 4 heteroatom(s) of one or two kind(s) selected from a nitrogen atom, a sulfur atom and an oxygen atom as a ring-constituting atom, besides carbon atoms, preferably (i) 5- to 14-membered (preferably 5- to 10-membered) aromatic heterocyclic group, (ii) 5- to 10-membered non-aromatic heterocyclic group and the like can be mentioned. Of these, 5- or 6-membered aromatic heterocyclic group is preferable. Specifically, aromatic heterocyclic group such as thienyl (e.g., 2-thienyl, 3-thienyl), furyl (e.g., 2-furyl, 3-furyl), pyridyl (e.g., 2-pyridyl, 3-pyridyl, 4-pyridyl), thiazolyl (e.g., 2-thiazolyl, 4-thiazolyl, 5-thiazolyl), oxazolyl (e.g., 2-oxazolyl, 4-oxazolyl, 5-oxazolyl), pyrazinyl, pyrimidinyl (e.g., 2-pyrimidinyl, 4-pyrimidinyl), pyrrolyl (e.g., 1-pyrrolyl, 2-pyrrolyl, 3-pyrrolyl), imidazolyl (e.g., 1-imidazolyl, 2-imidazolyl, 4-imidazolyl), pyrazolyl (e.g., 1-pyrazolyl, 3-pyrazolyl, 4-pyrazolyl), triazolyl (e.g., 1-triazolyl, 2-triazolyl), tetrazolyl, pyridazinyl (e.g., 3-pyridazinyl, 4-pyridazinyl), isothiazolyl (e.g., 3-isothiazolyl, 4-isothiazolyl, 5-isothiazolyl), isoxazolyl (e.g., 3-isoxazolyl, 4-isoxazolyl, 5-isoxazolyl), indolyl (e.g., 1-indolyl, 2-indolyl, 3-indolyl), 2-benzothiazolyl, 2-benzoxazolyl, benzimidazolyl (e.g., 1-benzimidazolyl, 2-benzimidazolyl), benzo[b]thienyl (e.g., 2-benzo[b]thienyl, 3-benzo[b]thienyl), benzo[b]furanyl (e.g., 2-benzo[b]furanyl, 3-benzo[b]furanyl), quinolyl (e.g., 2-quinolyl, 3-quinolyl, 4-quinolyl, 5-quinolyl, 8-quinolyl), isoquinolyl (e.g., 1-isoquinolyl, 3-isoquinolyl, 4-isoquinolyl, 5-isoquinolyl) and the like;

non-aromatic heterocyclic group such as pyrrolidinyl (e.g., 1-pyrrolidinyl, 2-pyrrolidinyl, 3-pyrrolidinyl), oxazolidinyl (e.g., 2-oxazolidinyl), imidazolinyl (e.g., 1-imidazolinyl, 2-imidazolinyl, 4-imidazolinyl), piperidinyl (e.g., 1-piperidinyl, 2-piperidinyl, 3-piperidinyl, 4-piperidinyl), piperazinyl (e.g., 1-piperazinyl, 2-piperazinyl), morpholinyl (e.g., 2-morpholinyl, 3-morpholinyl, 4-morpholinyl), thiomorpholinyl (e.g., 2-thiomorpholinyl, 3-thiomorpholinyl, 4-thiomorpholinyl), tetrahydropyranyl and the like, and the like can be mentioned.

Unless otherwise specified, as the "$C_{1-6}$ alkyl-carbonyl group" in the present specification, for example, acetyl, isobutanoyl, isopentanoyl and the like can be mentioned.

Unless otherwise specified, as the "$C_{1-6}$ alkoxy-carbonyl group" in the present specification, for example, methoxycarbonyl, ethoxycarbonyl, propoxycarbonyl, tert-butoxycarbonyl and the like can be mentioned.

Unless otherwise specified, as the "$C_{3-8}$ cycloalkyl-carbonyl group" in the present specification, for example, cyclopentylcarbonyl, cyclohexylcarbonyl and the like can be mentioned.

Unless otherwise specified, as the "$C_{6-14}$ aryl-carbonyl group" in the present specification, for example, benzoyl, 1-naphthoyl, 2-naphthoyl and the like can be mentioned.

Unless otherwise specified, as the "$C_{7-16}$ aralkyl-carbonyl group" in the present specification, for example, phenylacetyl, 2-phenylpropanoyl and the like can be mentioned.

Unless otherwise specified, as the "$C_{6-14}$ aryloxy-carbonyl group" in the present specification, for example, phenyloxycarbonyl, naphthyloxycarbonyl and the like can be mentioned.

Unless otherwise specified, as the "$C_{7-16}$ aralkyloxy-carbonyl group" in the present specification, for example, benzyloxycarbonyl, phenethyloxycarbonyl and the like can be mentioned.

Unless otherwise specified, as the "nitrogen-containing heterocyclyl-carbonyl group" in the present specification, for example, pyrrolidinylcarbonyl, piperidinocarbonyl and the like can be mentioned.

Unless otherwise specified, as the "$C_{1-6}$ alkylsulfonyl group" in the present specification, for example, methylsulfonyl, ethylsulfonyl and the like can be mentioned.

Unless otherwise specified, as the "$C_{6-14}$ arylsulfonyl group" in the present specification, for example, phenylsulfonyl, 1-naphthylsulfonyl, 2-naphthylsulfonyl and the like can be mentioned.

Unless otherwise specified, as the "$C_{1-6}$ alkylsulfinyl group" in the present specification, for example, methylsulfinyl, ethylsulfinyl and the like can be mentioned.

Unless otherwise specified, as the "$C_{6-14}$ arylsulfinyl group" in the present specification, for example, phenylsulfinyl, 1-naphthylsulfinyl, 2-naphthylsulfinyl and the like can be mentioned.

Unless otherwise specified, as the "optionally esterified carboxyl group" in the present specification, for example, carboxyl, $C_{1-6}$ alkoxy-carbonyl group (e.g., methoxycarbonyl, ethoxycarbonyl, propoxycarbonyl, tert-butoxycarbonyl etc.), $C_{6-14}$ aryloxy-carbonyl group (e.g., phenoxycarbonyl etc.), $C_{7-16}$ aralkyloxy-carbonyl group (e.g., benzyloxycarbonyl, phenethyloxycarbonyl etc.) and the like can be mentioned.

Unless otherwise specified, as the "optionally halogenated $C_{1-6}$ alkyl group" in the present specification, the above-mentioned "$C_{1-6}$ alkyl group" optionally substituted by 1 to 5 above-mentioned "halogen atoms" can be mentioned. For example, methyl, ethyl, propyl, isopropyl, butyl, tert-butyl, isobutyl, trifluoromethyl and the like can be mentioned.

Unless otherwise specified, as the "optionally halogenated $C_{1-6}$ alkoxy group" in the present specification, the above-mentioned "$C_{1-6}$ alkoxy group" optionally substituted by 1 to 5 above-mentioned "halogen atom" can be mentioned. For example, methoxy, ethoxy, isopropoxy, tert-butoxy, trifluoromethoxy and the like can be mentioned.

Unless otherwise specified, as the "mono- or di-$C_{1-6}$ alkyl-amino group" in the present specification, amino group mono- or di-substituted by the above-mentioned "$C_{1-6}$ alkyl group" can be mentioned. For example, methylamino, ethylamino, propylamino, dimethylamino, diethylamino and the like can be mentioned.

Unless otherwise specified, as the "mono- or di-$C_{6-14}$ aryl-amino group" in the present specification, amino group mono- or di-substituted by the above-mentioned "$C_{6-14}$ aryl group" can be mentioned. For example, phenylamino, diphenylamino, 1-naphthylamino, 2-naphthylamino and the like can be mentioned.

Unless otherwise specified, as the "mono- or di-$C_{7-16}$ aralkyl-amino group" in the present specification, amino group mono- or di-substituted by the above-mentioned "$C_{7-16}$ aralkyl group" can be mentioned. For example, benzylamino, phenethylamino and the like can be mentioned.

Unless otherwise specified, as the "N—$C_{1-6}$ alkyl-N—$C_{6-14}$ aryl-amino group" in the present specification, amino group substituted by the above-mentioned "$C_{1-6}$ alkyl group" and the above-mentioned "$C_{6-14}$ aryl group" can be mentioned. For example, N-methyl-N-phenylamino, N-ethyl-N-phenylamino and the like can be mentioned.

Unless otherwise specified, as the "N—$C_{1-6}$ alkyl-N—$C_{7-16}$ aralkyl-amino group" in the present specification, amino group substituted by the above-mentioned "$C_{1-6}$ alkyl group" and the above-mentioned "$C_{7-16}$ aralkyl group" can be mentioned. For example, N-methyl-N-benzylamino, N-ethyl-N-benzylamino and the like can be mentioned.

Unless otherwise specified, as the "mono- or di-$C_{1-6}$ alkyl-carbamoyl group" in the present specification, carbamoyl group mono- or di-substituted by the above-mentioned "$C_{1-6}$ alkyl group" can be mentioned. For example, methylcarbamoyl, ethylcarbamoyl, dimethylcarbamoyl, diethylcarbamoyl, ethylmethylcarbamoyl and the like can be mentioned.

Unless otherwise specified, as the "mono- or di-$C_{6-14}$ aryl-carbamoyl group" in the present specification, carbamoyl group mono- or di-substituted by the above-mentioned "$C_{6-14}$ aryl group" can be mentioned. For example, phenylcarbamoyl, 1-naphthylcarbamoyl, 2-naphthylcarbamoyl and the like can be mentioned.

Unless otherwise specified, as the "mono- or di-$C_{3-8}$ cycloalkyl-carbamoyl group" in the present specification, a carbamoyl group mono- or di-substituted by the above-mentioned "$C_{3-8}$ cycloalkyl group" can be mentioned. For example, cyclopropylcarbamoyl and the like can be mentioned.

Unless otherwise specified, as the "mono- or di-$C_{7-16}$ aralkyl-carbamoyl group" in the present specification, a carbamoyl group mono- or di-substituted by the above-mentioned "$C_{7-16}$ aralkyl group" can be mentioned. For example, benzylcarbamoyl and the like can be mentioned.

Unless otherwise specified, as the "mono- or di-5- to 7-membered heterocyclyl-carbamoyl group" in the present specification, carbamoyl group mono- or di-substituted by 5- to 7-membered heterocyclic group can be mentioned. As the 5- to 7-membered heterocyclic group, a heterocyclic group containing 1 to 4 heteroatom(s) of one or two kind(s) selected from a nitrogen atom, a sulfur atom and an oxygen atom as a ring-constituting atom, besides carbon atoms can be mentioned. As preferable examples of the "mono- or di-5- to 7-membered heterocyclyl-carbamoyl group", 2-pyridylcarbamoyl, 3-pyridylcarbamoyl, 4-pyridylcarbamoyl, 2-thienylcarbamoyl, 3-thienylcarbamoyl and the like can be mentioned.

Unless otherwise specified, as the "mono- or di-$C_{1-6}$ alkyl-sulfamoyl group" in the present specification, sulfamoyl group mono- or di-substituted by the above-mentioned "$C_{1-6}$ alkyl group" can be used, for example, methylsulfamoyl, ethylsulfamoyl, dimethylsulfamoyl, diethylsulfamoyl and the like can be mentioned.

Unless otherwise specified, as the "mono- or di-$C_{6-14}$ aryl-sulfamoyl group" in the present specification, sulfamoyl group mono- or di-substituted by the above-mentioned "$C_{6-14}$ aryl group" can be used, for example, phenylsulfamoyl, diphenylsulfamoyl, 1-naphthylsulfamoyl, 2-naphthylsulfamoyl and the like can be mentioned.

Unless otherwise specified, as the "mono- or di-$C_{7-16}$ aralkyl-sulfamoyl group" in the present specification, a sulfamoyl group mono- or di-substituted by the above-mentioned "$C_{7-16}$ aralkyl group" can be mentioned. For example, benzylsulfamoyl and the like can be mentioned.

Unless otherwise specified, as the "optionally substituted $C_{1-6}$ alkyl group", "optionally substituted $C_{2-6}$ alkenyl group", "optionally substituted $C_{2-6}$ alkynyl group", "optionally substituted $C_{1-10}$ alkoxy group (including optionally substituted $C_{1-6}$ alkoxy group)" and "optionally substituted $C_{1-10}$ alkylthio group (including optionally substituted $C_{1-6}$ alkylthio group)" in the present specification, for example, "$C_{1-6}$ alkyl group", "$C_{2-6}$ alkenyl group", "$C_{2-6}$ alkynyl group", "$C_{1-10}$ alkoxy group (including $C_{1-6}$ alkoxy group)", and "$C_{1-10}$ alkylthio group (including $C_{1-6}$ alkylthio group)", each of which optionally has 1 to 5 substituent(s) at substitutable position(s) selected from (1) halogen atom;
(2) hydroxy group;
(3) amino group;
(4) nitro group;
(5) cyano group;
(6) heterocyclic group (preferably furyl, pyridyl, thienyl, pyrazolyl, thiazolyl, oxazolyl) optionally substituted by 1 to 3 substituent(s) selected from halogen atom, hydroxy group, amino group, nitro group, cyano group, optionally halogenated $C_{1-6}$ alkyl group, mono- or di-$C_{1-6}$ alkyl-amino group, $C_{6-14}$ aryl group, mono- or di-$C_{6-14}$ aryl-amino group, $C_{3-8}$ cycloalkyl group, $C_{1-6}$ alkoxy group, $C_{1-6}$ alkoxy-$C_{1-6}$ alkoxy group, $C_{1-6}$ alkylthio group, $C_{1-6}$ alkylsulfinyl group, $C_{1-6}$ alkylsulfonyl group, optionally esterified carboxyl group, carbamoyl group, thiocarbamoyl group, mono- or di-$C_{1-6}$ alkyl-carbamoyl group, mono- or di-$C_{6-14}$ aryl-carbamoyl group, sulfamoyl group, mono- or di-$C_{1-6}$ alkyl-sulfamoyl group and mono- or di-$C_{6-14}$ aryl-sulfamoyl group;

(7) mono- or di-$C_{1-6}$ alkyl-amino group;
(8) mono- or di-$C_{6-14}$ aryl-amino group;
(9) mono- or di-$C_{7-16}$ aralkyl-amino group;
(10) N—$C_{1-6}$ alkyl-N—$C_{6-14}$ aryl-amino group;
(11) N—$C_{1-6}$ alkyl-N—$C_{7-16}$ aralkyl-amino group;
(12) $C_{3-8}$ cycloalkyl group;
(13) optionally halogenated $C_{1-6}$ alkoxy group;
(14) $C_{1-6}$ alkylthio group;
(15) $C_{1-6}$ alkylsulfinyl group;
(16) $C_{1-6}$ alkylsulfonyl group;
(17) optionally esterified carboxyl group;
(18) $C_{1-6}$ alkyl-carbonyl group;
(19) $C_{3-8}$ cycloalkyl-carbonyl group;
(20) $C_{6-14}$ aryl-carbonyl group;
(21) carbamoyl group;
(22) thiocarbamoyl group;
(23) mono- or di-$C_{1-6}$ alkyl-carbamoyl group;
(24) mono- or di-$C_{6-14}$ aryl-carbamoyl group;
(25) mono- or di-5- to 7-membered heterocyclyl-carbamoyl group;
(26) $C_{1-6}$ alkyl-carbonylamino group (e.g., acetylamino, propionylamino) optionally substituted by carboxyl group;
(27) $C_{6-14}$ aryloxy group optionally substituted by 1 to 3 substituent(s) selected from halogen atom, hydroxy group, amino group, nitro group, cyano group, optionally halogenated $C_{1-6}$ alkyl group, mono- or di-$C_{1-6}$ alkyl-amino group, $C_{6-14}$ aryl group, mono- or di-$C_{6-14}$ aryl-amino group, $C_{3-8}$ cycloalkyl group, $C_{1-6}$ alkoxy group, $C_{1-6}$ alkoxy-$C_{1-6}$ alkoxy group, $C_{1-6}$ alkylthio group, $C_{1-6}$ alkylsulfinyl group, $C_{1-6}$ alkylsulfonyl group, optionally esterified carboxyl group, carbamoyl group, thiocarbamoyl group, mono- or di-$C_{1-6}$ alkyl-carbamoyl group, mono- or di-$C_{6-14}$ aryl-carbamoyl group, sulfamoyl group, mono- or di-$C_{1-6}$ alkyl-sulfamoyl group and mono- or di-$C_{6-14}$ aryl-sulfamoyl group;
(28) $C_{6-14}$ aryl group optionally substituted by 1 to 3 substituent(s) selected from halogen atom, hydroxy group, amino group, nitro group, cyano group, optionally halogenated $C_{1-6}$ alkyl group, mono- or di-$C_{1-6}$ alkyl-amino group, $C_{6-14}$ aryl group, mono- or di-$C_{6-14}$ aryl-amino group, $C_{3-8}$ cycloalkyl group, $C_{1-6}$ alkoxy group, $C_{1-6}$ alkoxy-$C_{1-6}$ alkoxy group, $C_{1-6}$ alkylthio group, $C_{1-6}$ alkylsulfinyl group, $C_{1-6}$ alkylsulfonyl group, optionally esterified carboxyl group, carbamoyl group, thiocarbamoyl group, mono- or di-$C_{1-6}$ alkyl-carbamoyl group, mono- or di-$C_{6-14}$ aryl-carbamoyl group, sulfamoyl group, mono- or di-$C_{1-6}$ alkyl-sulfamoyl group and mono- or di-$C_{6-14}$ aryl-sulfamoyl group;
(29) heterocyclyloxy group;
(30) sulfamoyl group;
(31) mono- or di-$C_{1-6}$ alkyl-sulfamoyl group;
(32) mono- or di-$C_{6-14}$ aryl-sulfamoyl group;
(33) $C_{7-16}$ aralkyloxy group optionally substituted by 1 to 3 substituent(s) selected from halogen atom, hydroxy group, amino group, nitro group, cyano group, optionally halogenated $C_{1-6}$ alkyl group, mono- or di-$C_{1-6}$ alkyl-amino group, $C_{6-14}$ aryl group, mono- or di-$C_{6-14}$ aryl-amino group, $C_{3-8}$ cycloalkyl group, $C_{1-6}$ alkoxy group, $C_{1-6}$ alkoxy-$C_{1-6}$ alkoxy group, $C_{1-6}$ alkylthio group, $C_{1-6}$ alkylsulfinyl group, $C_{1-6}$ alkylsulfonyl group, optionally esterified carboxyl group, carbamoyl group, thiocarbamoyl group, mono- or di-$C_{1-6}$ alkyl-carbamoyl group, mono- or di-$C_{6-14}$ aryl-carbamoyl group, sulfamoyl group, mono- or di-$C_{1-6}$ alkyl-sulfamoyl group and mono- or di-$C_{6-14}$ aryl-sulfamoyl group; and the like, can be mentioned.

As the "optionally substituted $C_{3-8}$ cycloalkyl group", "optionally substituted $C_{6-14}$ aryl group", "optionally substituted $C_{7-16}$ aralkyl group", "optionally substituted heterocyclic group", "optionally substituted heterocyclyloxy group", "optionally substituted $C_{6-14}$ aryloxy group", "optionally substituted $C_{7-16}$ aralkyloxy group", "optionally substituted heterocyclylthio group", "optionally substituted $C_{6-14}$ arylthio group" and "optionally substituted $C_{7-16}$ aralkylthio group" in the present specification, for example, "$C_{3-8}$ cycloalkyl group", "$C_{6-14}$ aryl group", "$C_{7-16}$ aralkyl group", "heterocyclic group", "heterocyclyloxy group", "$C_{6-14}$ aryloxy group", "$C_{7-16}$ aralkyloxy group", "heterocyclylthio group", "$C_{6-14}$ arylthio group" and "$C_{7-16}$ aralkylthio group", each of which optionally has 1 to 5 substituent(s) at substitutable position(s) selected from (1) halogen atom;
(2) hydroxy group;
(3) amino group;
(4) nitro group;
(5) cyano group;
(6) optionally substituted $C_{1-6}$ alkyl group;
(7) optionally substituted $C_{2-6}$ alkenyl group;
(8) optionally substituted $C_{2-6}$ alkynyl group;
(9) $C_{6-14}$ aryl group optionally substituted by 1 to 3 substituent(s) selected from halogen atom, hydroxy group, amino group, nitro group, cyano group, optionally halogenated $C_{1-6}$ alkyl group, mono- or di-$C_{1-6}$ alkyl-amino group, $C_{6-14}$ aryl group, mono- or di-$C_{6-14}$ aryl-amino group, $C_{3-8}$ cycloalkyl group, $C_{1-6}$ alkoxy group, $C_{1-6}$ alkoxy-$C_{1-6}$ alkoxy group, $C_{1-6}$ alkylthio group, $C_{1-6}$ alkylsulfinyl group, $C_{1-6}$ alkylsulfonyl group, optionally esterified carboxyl group, carbamoyl group, thiocarbamoyl group, mono- or di-$C_{1-6}$ alkyl-carbamoyl group, mono- or di-$C_{6-14}$ aryl-carbamoyl group, sulfamoyl group, mono- or di-$C_{1-6}$ alkyl-sulfamoyl group and mono- or di-$C_{6-14}$ aryl-sulfamoyl group;
(10) $C_{6-14}$ aryloxy group optionally substituted by 1 to 3 substituent(s) selected from halogen atom, hydroxy group, amino group, nitro group, cyano group, optionally halogenated $C_{1-6}$ alkyl group, mono- or di-$C_{1-6}$ alkyl-amino group, $C_{6-14}$ aryl group, mono- or di-$C_{6-14}$ aryl-amino group, $C_{3-8}$ cycloalkyl group, $C_{1-6}$ alkoxy group, $C_{1-6}$ alkoxy-$C_{1-6}$ alkoxy group, $C_{1-6}$ alkylthio group, $C_{1-6}$ alkylsulfinyl group, $C_{1-6}$ alkylsulfonyl group, optionally esterified carboxyl group, carbamoyl group, thiocarbamoyl group, mono- or di-$C_{1-6}$ alkyl-carbamoyl group, mono- or di-$C_{6-14}$ aryl-carbamoyl group, sulfamoyl group, mono- or di-$C_{1-6}$ alkyl-sulfamoyl group and mono- or di-$C_{6-14}$ aryl-sulfamoyl group;
(11) $C_{7-16}$ aralkyloxy group optionally substituted by 1 to 3 substituent(s) selected from halogen atom, hydroxy group, amino group, nitro group, cyano group, optionally halogenated $C_{1-6}$ alkyl group, mono- or di-$C_{1-6}$ alkyl-amino group, $C_{6-14}$ aryl group, mono- or di-$C_{6-14}$ aryl-amino group, $C_{3-8}$ cycloalkyl group, $C_{1-6}$ alkoxy group, $C_{1-6}$ alkoxy-$C_{1-6}$ alkoxy group, $C_{1-6}$ alkylthio group, $C_{1-6}$ alkylsulfinyl group, $C_{1-6}$ alkylsulfonyl group, optionally esterified carboxyl group, carbamoyl group, thiocarbamoyl group, mono- or di-$C_{1-6}$ alkyl-carbamoyl group, mono- or di-$C_{6-14}$ aryl-carbamoyl group, sulfamoyl group, mono- or di-$C_{1-6}$ alkyl-sulfamoyl group and mono- or di-$C_{6-14}$ aryl-sulfamoyl group;

(12) heterocyclic group (preferably furyl, pyridyl, thienyl, pyrazolyl, thiazolyl, oxazolyl) optionally substituted by 1 to 3 substituent(s) selected from halogen atom, hydroxy group, amino group, nitro group, cyano group, optionally halogenated $C_{1-6}$ alkyl group, mono- or di-$C_{1-6}$ alkyl-amino group, $C_{6-14}$ aryl group, mono- or di-$C_{6-14}$ aryl-amino group, $C_{3-8}$ cycloalkyl group, $C_{1-6}$ alkoxy group, $C_{1-6}$ alkoxy-$C_{1-6}$ alkoxy group, $C_{1-6}$ alkylthio group, $C_{1-6}$ alkylsulfinyl group, $C_{1-6}$ alkylsulfonyl group, optionally esterified carboxyl group, carbamoyl group, thiocarbamoyl group, mono- or di-$C_{1-6}$ alkyl-carbamoyl group, mono- or di-$C_{6-14}$ aryl-carbamoyl group, sulfamoyl group, mono- or di-$C_{1-6}$ alkyl-sulfamoyl group and mono- or di-$C_{6-14}$ aryl-sulfamoyl group;

(13) mono- or di-$C_{1-6}$ alkyl-amino group;
(14) mono- or di-$C_{6-14}$ aryl-amino group;
(15) mono- or di-$C_{7-16}$ aralkyl-amino group;
(16) N—$C_{1-6}$ alkyl-N—$C_{6-14}$ aryl-amino group;
(17) N—$C_{1-6}$ alkyl-N—$C_{7-16}$ aralkyl-amino group;
(18) $C_{3-8}$ cycloalkyl group;
(19) optionally substituted $C_{1-6}$ alkoxy group;
(20) $C_{1-6}$ alkylthio group;
(21) $C_{1-6}$ alkylsulfinyl group;
(22) $C_{1-6}$ alkylsulfonyl group;
(23) optionally esterified carboxyl group;
(24) $C_{1-6}$ alkyl-carbonyl group;
(25) $C_{3-8}$ cycloalkyl-carbonyl group;
26) $C_{6-14}$ aryl-carbonyl group;
27) carbamoyl group;
28) thiocarbamoyl group;
(29) mono- or di-$C_{1-6}$ alkyl-carbamoyl group;
(30) mono- or di-$C_{6-14}$ aryl-carbamoyl group;
(31) mono- or di-5- to 7-membered heterocyclyl-carbamoyl group;
(32) sulfamoyl group;
(33) mono- or di-$C_{1-6}$ alkyl-sulfamoyl group;
(34) mono- or di-$C_{6-14}$ aryl-sulfamoyl group; and the like, can be mentioned.

Unless otherwise specified, as the "optionally substituted amino group" in the present specification, amino group optionally substituted by 1 or 2 substituent(s) selected from
(1) optionally substituted $C_{1-6}$ alkyl group;
(2) optionally substituted $C_{2-6}$ alkenyl group;
(3) optionally substituted $C_{2-6}$ alkynyl group;
(4) optionally substituted $C_{3-8}$ cycloalkyl group;
(5) optionally substituted $C_{6-14}$ aryl group;
(6) optionally substituted $C_{1-6}$ alkoxy group;
(7) optionally substituted acyl group;
(8) optionally substituted heterocyclic group (preferably furyl, pyridyl, thienyl, pyrazolyl, thiazolyl, oxazolyl);
(9) sulfamoyl group;
(10) mono- or di-$C_{1-6}$ alkyl-sulfamoyl group;
(11) mono- or di-$C_{6-14}$ aryl-sulfamoyl group; and the like, can be mentioned. When the "optionally substituted amino group" is an amino group substituted by 2 substituents, these substituents may form a nitrogen-containing heterocycle together with the adjacent nitrogen atom. As the "nitrogen-containing heterocycle", for example, a 5- to 7-membered nitrogen-containing heterocycle containing at least one nitrogen atom and optionally further containing 1 or 2 heteroatom(s) selected from an oxygen atom, a sulfur atom and a nitrogen atom as a ring-constituting atom, besides carbon atoms can be mentioned. As referable examples of the nitrogen-containing heterocycle, pyrrolidine, imidazolidine, pyrazolidine, piperidine, piperazine, morpholine, thiomorpholine, thiazolidine, oxazolidine and the like can be mentioned.

Unless otherwise specified, as the "optionally substituted acyl group" in the present specification, groups represented by the formula: —$COR^2$, —CO—$OR^2$, —$SO_2R^2$, —$SOR^2$, —$PO(OR^2)(OR^3)$, —CO—$NR^{2a}R^{3a}$ and —CS—$NR^{2a}R^{3a}$, wherein $R^2$ and $R^3$ are the same or different and each is a hydrogen atom, an optionally substituted hydrocarbon group or an optionally substituted heterocyclic group, and $R^{2a}$ and $R^{3a}$ are the same or different and each is a hydrogen atom, an optionally substituted hydrocarbon group or an optionally substituted heterocyclic group, or $R^{2a}$ and $R^{3a}$ may form an optionally substituted nitrogen-containing heterocycle together with the adjacent nitrogen atom, and the like can be mentioned.

As the "nitrogen-containing heterocycle" of the "optionally substituted nitrogen-containing heterocycle" which $R^{2a}$ and $R^{3a}$ form together with the adjacent nitrogen atom, for example, a 5- to 7-membered nitrogen-containing heterocycle containing at least one nitrogen atom and optionally further containing 1 to 2 heteroatom(s) selected from an oxygen atom, a sulfur atom and a nitrogen atom as a ring-constituting atom, besides carbon atoms can be mentioned. As preferable examples of the "nitrogen-containing heterocycle", pyrrolidine, imidazolidine, pyrazolidine, piperidine, piperazine, morpholine, thiomorpholine, thiazolidine, oxazolidine and the like can be mentioned.

The nitrogen-containing heterocycle optionally has 1 to 2 substituent(s) at substitutable position(s). As these substituent(s), a hydroxy group, an optionally halogenated $C_{1-6}$ alkyl group, a $C_{6-14}$ aryl group, a $C_{7-16}$ aralkyl group and the like can be mentioned.

As preferable examples of "optionally substituted acyl group", formyl group; carboxyl group; carbamoyl group; $C_{1-6}$ alkyl-carbonyl group; $C_{1-6}$ alkoxy-carbonyl group; $C_{3-8}$ cycloalkyl-carbonyl group; $C_{6-14}$ aryl-carbonyl group; $C_{7-16}$ aralkyl-carbonyl group; $C_{6-14}$ aryloxy-carbonyl group; $C_{7-16}$ aralkyloxy-carbonyl group; mono- or di-$C_{1-6}$ alkylcarbamoyl group; mono- or di-$C_{6-14}$ aryl-carbamoyl group; mono- or di-$C_{3-8}$ cycloalkyl-carbamoyl group; mono- or di-$C_{7-16}$ aralkyl-carbamoyl group; $C_{1-6}$ alkylsulfonyl group; $C_{6-14}$ arylsulfonyl group optionally substituted by nitro group; nitrogen-containing heterocyclyl-carbonyl group; $C_{1-6}$ alkyl-sulfinyl group; $C_{6-14}$ arylsulfinyl group; thiocarbamoyl group; sulfamoyl group; mono- or di-$C_{1-6}$ alkyl-sulfamoyl group; mono- or di-$C_{6-14}$ aryl-sulfamoyl group; mono- or di-$C_{7-16}$ aralkyl-sulfamoyl group; and the like can be mentioned.

The definition of each symbol in the formulas (I) and (I') is explained in detail in the following.

Ar is an optionally substituted cyclic group. Here, as the "cyclic group", for example, $C_{3-8}$ cycloalkyl group, aromatic hydrocarbon group (e.g., $C_{6-14}$ aryl group), heterocyclic group and the like can be mentioned. Preferable and specific examples of the "cyclic group" include cyclopropyl, cyclohexyl, phenyl, naphthyl, thienyl, furyl, thiazolyl, oxazolyl, imidazolyl, pyrazolyl, triazolyl, pyridyl, pyrazinyl, benzo[b]thienyl, indolyl, indanyl and the like.

The cyclic group represented by Ar is preferably an aromatic hydrocarbon group (e.g., $C_{6-14}$ aryl group), more preferably phenyl.

The cyclic group represented by Ar may have, for example, 1-5, preferably 1-3, substituent(s) at substitutable position(s). As the "substituent", those exemplarily shown as substituents for the aforementioned "optionally substituted $C_{3-8}$ cycloalkyl group" can be used. When the cyclic group has 2 or more substituents, the respective substituents may be the same or different.

The substituent is preferably halogen atom; cyano group; optionally halogenated $C_{1-6}$ alkyl group; $C_{6-14}$ aryl group; hydroxy group; $C_{1-10}$ alkoxy group optionally substituted by 1 to 3 substituent(s) selected from $C_{3-8}$ cycloalkyl group, optionally halogenated $C_{1-6}$ alkoxy group and the like; heterocyclyloxy group (preferably tetrahydropyranyloxy); $C_{7-16}$ aralkyloxy group; carboxyl group; $C_{1-6}$ alkyl-carbonyl group; $C_{6-14}$ aryl-carbonyl group; or the like.

As the "ring" represented by ring A and ring $A^1$, for example, aromatic rings such as aromatic hydrocarbon, aromatic heterocycle and the like; non-aromatic rings such as alicyclic hydrocarbon, non-aromatic heterocycle and the like can be mentioned.

As the aromatic hydrocarbon, for example, an aromatic hydrocarbon having 6 to 14 carbon atoms can be mentioned. As preferable examples of aromatic hydrocarbon, benzene, naphthalene, anthracene, phenanthrene, acenaphthylene and the like can be mentioned.

As the aromatic heterocycle, for example, a 5- to 7-membered monocyclic aromatic heterocycle containing, as a ring-constituting atom besides carbon atoms, 1 to 4 heteroatom(s) selected from an oxygen atom, a sulfur atom and a nitrogen atom, or a fused aromatic heterocycle can be mentioned. As the fused aromatic heterocycle, a ring wherein these 5- to 7-membered monocyclic aromatic heterocycles, and a 6-membered ring containing 1 or 2 nitrogen atom(s), a benzene ring or a 5-membered ring containing one sulfur atom are fused, and the like can be mentioned.

As preferable examples of aromatic heterocycle, furan, thiophene, pyridine, pyrimidine, pyridazine, pyrazine, pyrrole, imidazole, pyrazole, isoxazole, isothiazole, oxazole, thiazole, oxadiazole, thiadiazole, triazole, tetrazole, quinoline, quinazoline, quinoxaline, benzofuran, benzothiophene, benzoxazole, benzothiazole, benzimidazole, indole, 1H-indazole, 1H-pyrrolo[2,3-b]pyrazine, 1H-pyrrolopyridine, 1H-imidazopyridine, 1H-imidazopyrazine, triazine, isoquinoline, benzothiadiazole and the like can be mentioned.

As the alicyclic hydrocarbon, saturated or unsaturated alicyclic hydrocarbon having 3 to 12 carbon atoms, such as cycloalkane, cycloalkene, cycloalkadiene and the like can be mentioned.

As preferable examples of cycloalkane, cycloalkane having 3 to 10 carbon atoms, such as cyclopropane, cyclobutane, cyclopentane, cyclohexane, cycloheptane, cyclooctane, bicyclo[2.2.1]heptane, bicyclo[2.2.2]octane, bicyclo[3.2.1]octane, bicyclo[3.2.2]nonane, bicyclo[3.3.1]nonane, bicyclo[4.2.1]nonane, bicyclo[4.3.1]decane and the like can be mentioned.

As preferable examples of cycloalkene, cycloalkene having 3 to 10 carbon atoms, such as cyclobutene, cyclopentene, cyclohexene and the like can be mentioned.

As preferable examples of cycloalkadiene, cycloalkadiene having 4 to 10 carbon atoms, such as 2,4-cyclopentadiene, 2,4-cyclohexadiene, 2,5-cyclohexadiene and the like can be mentioned.

As the non-aromatic heterocycle, for example, 5- to 7-membered monocyclic non-aromatic heterocycle containing, as a ring-constituting atom besides carbon atom, 1 to 4 heteroatom(s) selected from an oxygen atom, a sulfur atom and a nitrogen atom, or a fused non-aromatic heterocycle can be mentioned. As the fused non-aromatic heterocycle, for example, a ring wherein these 5- to 7-membered monocyclic non-aromatic heterocycles, and a 6-membered ring containing 1 or 2 nitrogen atom(s), a benzene ring or a 5-membered ring containing one sulfur atom are fused, and the like can be mentioned.

As preferable examples of the non-aromatic heterocycle, dihydrofuran, tetrahydrofuran, dihydrothiophene, tetrahydrothiophene, pyrrolidine, pyrroline, pyrazolidine, piperidine, piperazine, morpholine, thiomorpholine, hexamethyleneimine, oxazolidine, thiazolidine, imidazolidine, imidazoline, tetrahydrofuran, azepane, oxepane, tetrahydropyridine and the like can be mentioned.

Of the above-mentioned rings, aromatic rings such as benzene, pyrazole, thiazole, oxazole, furan, thiophene, oxadiazole, triazole, tetrazole, pyrimidine, benzimidazole, indole and the like are preferable, and benzene is particularly preferable.

The ring represented by ring A is not thiazole, oxazole, imidazole and pyrazole.

The "ring" represented by ring A and ring $A^1$ may have, for example, 1-5, preferably 1-3, substituent(s) at substitutable position(s). As the "substituent", those exemplarily shown as substituents for the aforementioned "optionally substituted $C_{3-8}$ cycloalkyl group" can be used. When the ring has 2 or more substituents, the respective substituents may be the same or different.

The substituent is preferably halogen atom, $C_{7-16}$ aralkyl group, $C_{6-14}$ aryl group, $C_{1-10}$ alkoxy group, $C_{7-16}$ aralkyloxy group and the like.

The ring A is preferably benzene.

The "ring" represented by ring $A^1$ optionally has a substituent represented by the formula: Ar—Xa- (the symbols are as defined above).

The ring $A^1$ is preferably ring A having a substituent represented by the formula: Ar—Xa- (the symbols are as defined above).

Xa and Xb are each independently a bond or a spacer having a main chain of 1 to 5 atom(s).

For example, when Xa is a spacer having a main chain of 1 to 5 atom(s), the "main chain" means a divalent straight chain connecting Ar and ring A, and "the number of atoms of the main chain" is counted so as the number of atoms of the main chain is minimum.

Similarly, when Xb is a spacer having a main chain of 1 to 5 atom(s), the "main chain" means a divalent straight chain connecting ring A and Xc, and "the number of atoms of the main chain" is counted so as the number of atoms of the main chain is minimum.

The above-mentioned "main chain" consists of 1-5 atom(s) selected from a carbon atom and a heteroatom (e.g., an oxygen atom, a sulfur atom, a nitrogen atom and the like), and may be saturated or unsaturated. The carbon atom and sulfur atom may be oxidized.

As the "spacer having a main chain of 1 to 5 atom(s)", for example, (1) —$(CH_2)_k$— (k=an integer of 1-5);

(2) —$(CH_2)_{k1}$-Q-$(CH_2)_{k2}$— [k1 and k2 are independently an integer of 0-4, and k1+k2=an integer of 0-4; Q is O, $S(O)_{k3}$ (k3 is an integer of 0-2), CO or $N(R^4)$ ($R^4$ is a hydrogen atom or a substituent)];

(3) —$(CH_2)_{k4}$—$NR^4CO$—$(CH_2)_{k5}$— (k4 and k5 are independently an integer of 0-3, and k4+k5=an integer of 0-3, $R^4$ is as defined above) and the like can be mentioned.

As the substituent for $R^4$, those exemplarily shown as substituents for the aforementioned "optionally substituted $C_{3-8}$ cycloalkyl group" can be used. Of these, optionally substituted $C_{1-6}$ alkyl group (preferably $C_{1-6}$ alkyl group, $C_{7-16}$ aralkyl group and the like) and $C_{3-8}$ cycloalkyl group are preferable.

Specific examples of the "spacer having a main chain of 1 to 5 atom(s)" include
(1a) —CH$_2$—, —CH$_2$CH$_2$—, —CH$_2$CH$_2$CH$_2$—;
(2a) —O—, —CH$_2$O—, —CH$_2$CH$_2$O—, —OCH$_2$—, —O—CH$_2$CH$_2$—, —O—CH$_2$CH$_2$CH$_2$—;
(2b) —S—, —CH$_2$S—, —CH$_2$CH$_2$S—, —SCH$_2$—, —S—CH$_2$CH$_2$—, —S—CH$_2$CH$_2$CH$_2$—;
(2c) —CO—, —CO—CH$_2$—;
(2d) —NH—CH$_2$—, —NH—CH$_2$CH$_2$—, —CH$_2$NH— or —CH$_2$—NH—CH$_2$CH$_2$— each optionally having, on the N atom, a substituent selected from C$_{1-6}$ alkyl group, C$_{7-16}$ aralkyl group and C$_{3-8}$ cycloalkyl group;
(3a) —CH$_2$—NH—CO—; and the like.

Xa is preferably a bond; —O—; —S—; —CH$_2$—; —CO—; —CH$_2$O—; —CH$_2$S—; —CH$_2$NH— optionally having, on the N atom, a substituent selected from C$_{1-6}$ alkyl group and C$_{7-16}$ aralkyl group; —OCH$_2$—; —SCH$_2$—; —NH—CH$_2$— optionally having, on the N atom, a substituent selected from C$_{1-6}$ alkyl group and C$_{7-16}$ aralkyl group; —CH$_2$CH$_2$O—; —CH$_2$CH$_2$S—; —CH$_2$—NH—CO— optionally having, on the N atom, a substituent selected from C$_{1-6}$ alkyl group and C$_{7-16}$ aralkyl group; and the like. Xa is more preferably a bond.

Xb is preferably —CH$_2$—; —CH$_2$CH$_2$—; —CO—CH$_2$—; —CH$_2$CH$_2$CH$_2$—; —O—CH$_2$CH$_2$—; —S—CH$_2$CH$_2$—; —O—CH$_2$CH$_2$CH$_2$—; —S—CH$_2$CH$_2$CH$_2$—; —NH—CH$_2$CH$_2$— or —CH$_2$—NH—CH$_2$CH$_2$— each optionally having, on the N atom, a substituent selected from C$_{3-8}$ cycloalkyl group and C$_{7-16}$ aralkyl group; and the like. Xb is more preferably —CH$_2$—.

Xc is O, S, SO or SO$_2$, preferably O.

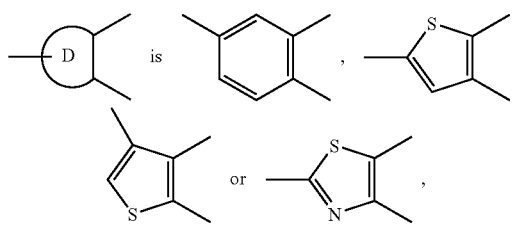

preferably

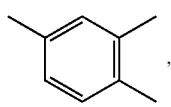

As the "5- to 7-membered ring" represented by ring B, for example, 5- to 7-membered rings from the ring exemplarily shown for ring A can be mentioned. Of these, 5- to 7-membered non-aromatic rings such as cycloalkane having 5 to 7 carbon atoms (preferably cyclopentane, cyclohexane, cycloheptane), cycloalkene having 5 to 7 carbon atoms (preferably cyclopentene, cyclohexene), 5- to 7-membered monocyclic non-aromatic heterocycle (preferably tetrahydrofuran, oxepane) and the like are preferable.

The ring B is more preferably cyclopentane or tetrahydrofuran, particularly preferably tetrahydrofuran.

As a preferable combination of ring D and ring B, a combination of benzene as ring D, and cyclopentane or tetrahydrofuran as ring B (ring B is preferably tetrahydrofuran) can be mentioned. That is,

is preferably

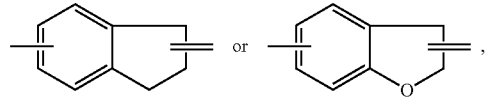

more preferably

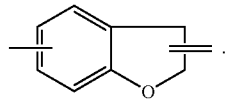

As the "5- to 7-membered non-aromatic ring" represented by ring B$^1$, those exemplarily shown as the aforementioned ring B can be mentioned.

The ring B$^1$ is preferably cyclopentane or tetrahydrofuran, more preferably tetrahydrofuran.

As a preferable combination of ring D and ring B$^1$, a combination of benzene as ring D, and cyclopentane or tetrahydrofuran as ring B$^1$ (ring B$^1$ is preferably tetrahydrofuran) can be mentioned. That is,

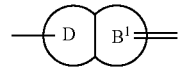

is preferably

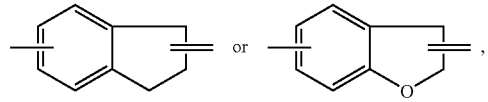

more preferably

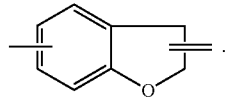

Xd is a bond, CH or CH$_2$, preferably CH$_2$.

R$^1$ is preferably a hydroxy group or a C$_{1-6}$ alkoxy group, more preferably a hydroxy group.

In the formula (I),
(i) when ring A is benzene, the cyclic group represented by Ar is not a quinolinyl group,
(ii) when ring B is a 5- to 7-membered aromatic ring, the ring represented by ring A is not thiophene and furan,
(iii) when ring B is benzene, the ring represented by ring A is not 5-membered aromatic heterocycle, and
(iv) when ring B is cyclohexane, Xd is not a bond.

The compound represented by the formula (I) does not include
[6-(4-biphenylyl)methoxy-2-tetralin]acetic acid;
methyl [6-(4-biphenylyl)methoxy-2-tetralin]acetate;
[7-(4-biphenylyl)methoxy-1,2,3,4-tetrahydro-2-oxo-3-quinoline]acetic acid; and
methyl [7-(4-biphenylyl)methoxy-1,2,3,4-tetrahydro-2-oxo-3-quinoline]acetate.

As preferable examples of compound (I), the following compounds can be mentioned.

[Compound A]

A compound wherein

Ar is an aromatic hydrocarbon group (preferably $C_{6-14}$ aryl group; more preferably phenyl) optionally having 1-3 substituent(s) selected from a halogen atom; a cyano group; an optionally halogenated $C_{1-6}$ alkyl group; a $C_{6-14}$ aryl group; a hydroxy group; a $C_{1-10}$ alkoxy group optionally substituted by 1 to 3 substituent(s) selected from a $C_{3-8}$ cycloalkyl group, an optionally halogenated $C_{1-6}$ alkoxy group and the like; a heterocyclyloxy group (preferably tetrahydropyranyloxy); a $C_{7-16}$ aralkyloxy group; a carboxyl group; a $C_{1-6}$ alkyl-carbonyl group; a $C_{6-14}$ aryl-carbonyl group; and the like;

ring A is an aromatic ring (preferably benzene, furan, thiophene, oxadiazole, triazole, tetrazole, pyrimidine, benzimidazole, indole; more preferably benzene) optionally having 1-3 substituent(s) selected from a halogen atom, a $C_{7-16}$ aralkyl group, a $C_{6-14}$ aryl group, a $C_{1-10}$ alkoxy group, a $C_{7-16}$ aralkyloxy group and the like;

Xa is a bond; —O—; —S—; —CH$_2$—; —CO—; —CH$_2$O—; —CH$_2$S—; —CH$_2$NH— optionally having, on the N atom, a substituent selected from a $C_{1-6}$ alkyl group and a $C_{7-16}$ aralkyl group; —OCH$_2$—; —SCH$_2$—; —NH—CH$_2$— optionally having, on the N atom, a substituent selected from a $C_{1-6}$ alkyl group and a $C_{7-16}$ aralkyl group; —CH$_2$CH$_2$O—; —CH$_2$CH$_2$S—; or —CH$_2$—NH—CO— optionally having, on the N atom, a substituent selected from a $C_{1-6}$ alkyl group and a $C_{7-16}$ aralkyl group (preferably a bond);

Xb is —CH$_2$—; —CH$_2$CH$_2$—; —CO—CH$_2$—; —CH$_2$CH$_2$CH$_2$—; —O—CH$_2$CH$_2$—; —S—CH$_2$CH$_2$—; —O—CH$_2$CH$_2$CH$_2$—; —S—CH$_2$CH$_2$CH$_2$—; or —NH—CH$_2$CH$_2$— or —CH$_2$—NH—CH$_2$CH$_2$— each optionally having, on the N atom, a substituent selected from $C_{3-8}$ cycloalkyl group and $C_{7-16}$ aralkyl group (preferably Xc is O;

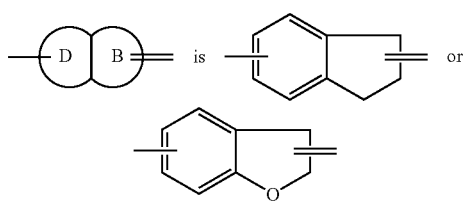

(preferably

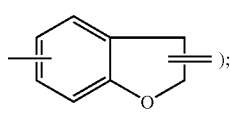);

Xd is CH$_2$; and

R$^1$ is a hydroxy group or a $C_{1-6}$ alkoxy group (preferably a hydroxy group);

[Compound B]

A compound represented by the formula:

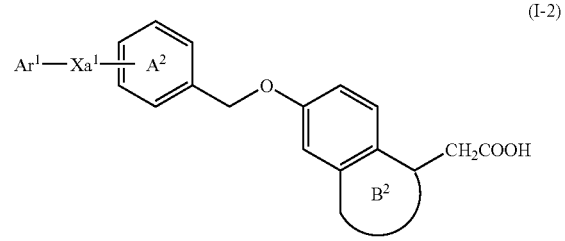

(I-2)

wherein Ar$^1$ is an optionally substituted phenyl group or an optionally substituted indanyl group, Xa$^1$ is a bond or a spacer having a main chain of 1 to 5 atom(s), ring A$^2$ is a benzene ring optionally further substituted, ring B$^2$ is a 5- to 7-membered ring (hereinafter sometimes to be abbreviated as compound (I-2)).

Here, Ar$^1$ is preferably a phenyl group or an indanyl group each optionally having substituent(s) selected from halogen atom, nitro group, carboxyl group, optionally halogenated $C_{1-6}$ alkyl group, hydroxy-$C_{1-6}$ alkyl group, carboxy-$C_{1-6}$ alkylcarbonylamino-$C_{1-6}$ alkyl group, optionally halogenated $C_{1-6}$ alkoxy group, $C_{6-14}$ aryl group, $C_{6-14}$ aryloxy group and $C_{7-16}$ aralkyloxy group. Specifically, a phenyl group optionally having substituent(s) selected from halogen atom, nitro group, carboxy group, optionally halogenated $C_{1-6}$ alkyl group, hydroxy-$C_{1-6}$ alkyl group, carboxy-$C_{1-6}$ alkylcarbonylamino-$C_{1-6}$ alkyl group, optionally halogenated $C_{1-6}$ alkoxy group, $C_{6-14}$ aryl group, $C_{6-14}$ aryloxy group and $C_{7-16}$ aralkyloxy group is preferably, and a phenyl group optionally having substituent(s) selected from halogen atom and optionally halogenated $C_{1-6}$ alkyl group is particularly preferable.

Xa$^1$ is preferably a bond, —O—, —CH$_2$—O—, —CO—, —CONH—, —N(CH$_3$)CH$_2$—, —S—CH$_2$—, —C=C— or the like, and a bond, —O— or —CH$_2$—O— is particularly preferable.

Ring A$^2$ is preferably a benzene ring optionally further substituted by a $C_{1-6}$ alkyl group.

In the formula (I-2) and the below-mentioned formulas (I-4), (I-1) and (I-3),

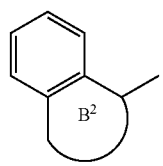

is preferably

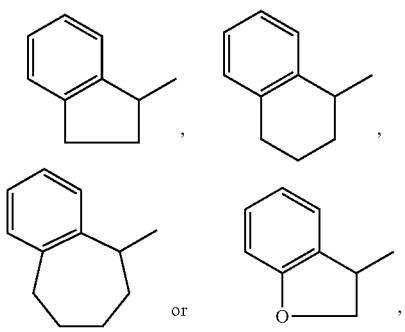

more preferably

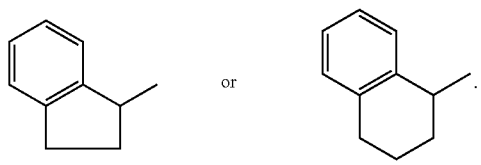

[Compound C]
A compound represented by the formula:

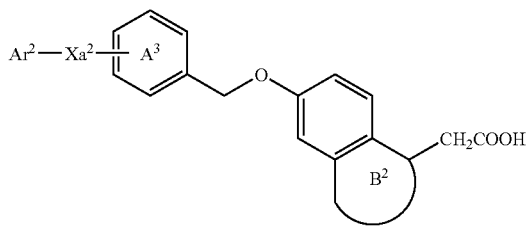

wherein Ar² is an optionally substituted thiazolyl group, Xa² is a bond or a spacer having a main chain of 1 to 5 atom(s), ring A³ is a benzene ring optionally further substituted, and ring B² is a 5- to 7-membered ring (hereinafter sometimes to be abbreviated as compound (I-4)).

Here, Ar² is preferably a thiazolyl group (e.g., 2-thiazolyl group) optionally having substituent(s) selected from a $C_{6-14}$ aryl group and a $C_{1-6}$ alkyl group.

Xa² is preferably —N(R⁵)—(CH₂)m- or —S—(CH₂)m- (R⁵ is a hydrogen atom or a $C_{1-6}$ alkyl group, and m is an integer of 0 to 3), and —N(R⁵)—(CH₂)m- is particularly preferable.

As R⁵, a $C_{1-3}$ alkyl group such as methyl, ethyl, propyl and the like are preferable, and methyl is particularly preferable.

Ring A³ is preferably a benzene ring.

[Compound D]
{6-[(2',6'-dimethylbiphenyl-3-yl)methoxy]-1,2,3,4-tetrahydronaphthalen-1-yl}acetic acid (Example 11);
8-[(2',6'-dimethylbiphenyl-3-yl)methoxy]-2,3,4,5-tetrahydro-1-benzoxepine-4-carboxylic acid (Example 13);
{5-[(2',6'-dimethylbiphenyl-3-yl)methoxy]-2,3-dihydro-1H-inden-1-yl}acetic acid (Example 17);
{6-[(2',6'-dimethylbiphenyl-3-yl)methoxy]-2,3-dihydro-1-benzofuran-3-yl}acetic acid (Example 33);
(6-{[3-(2-methyl-1-naphthyl)benzyl]oxy}-2,3-dihydro-1-benzofuran-3-yl)acetic acid (Example 47);
[6-({4-[(2-phenyl-1H-indol-1-yl)methyl]benzyl}oxy)-2,3-dihydro-1-benzofuran-3-yl]acetic acid (Example 66);
(6-{[4'-(benzyloxy)-2',6'-dimethylbiphenyl-3-yl]methoxy}-2,3-dihydro-1-benzofuran-3-yl)acetic acid (Example 70);
(6-{[4'-(2-ethoxyethoxy)-2',6'-dimethylbiphenyl-3-yl]methoxy}-2,3-dihydro-1-benzofuran-3-yl)acetic acid (Example 72);
calcium {6-[(4-{[(2-phenylethyl)(4-phenyl-1,3-thiazol-2-yl)amino]methyl}benzyl)oxy]-2,3-dihydro-1-benzofuran-3-yl}acetate (Example 73); and
(6-{[6-(benzyloxy)-2',6'-dimethylbiphenyl-3-yl]methoxy}-2,3-dihydro-1-benzofuran-3-yl)acetic acid (Example 75).

The present invention further provides a compound represented by the below-mentioned the formula (I-1), and a compound represented by the formula (I-3).

A compound represented by the formula:

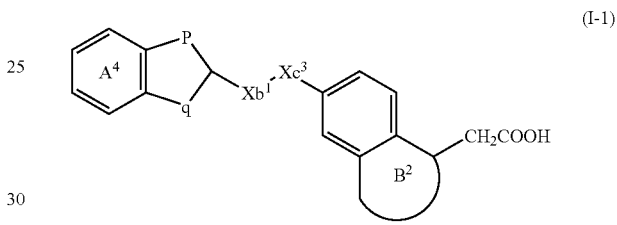

wherein ring A⁴ is an optionally substituted benzene ring,
p and q are independently an optionally substituted carbon chain having 0 to 4 carbon atom(s).
Xb¹ is a bond or a spacer having a main chain of 1 to 5 atoms,
Xc³ is O, S, SO or SO₂,
ring B² is a 5- to 7-membered ring, or a salt thereof (hereinafter sometimes to be abbreviated as compound (I-1)).

Here, ring A⁴ is preferably a benzene ring optionally having substituent(s) selected from (1) halogen atom, (2) $C_{1-6}$ alkyl group, (3) $C_{1-6}$ alkoxy group, (4) $C_{6-14}$ aryl group optionally substituted by halogen atom, $C_{1-6}$ alkyl or $C_{1-6}$ alkoxy, (5) $C_{6-14}$ aryloxy group and (6) $C_{7-16}$ aralkyloxy group.

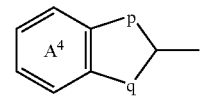

is preferably

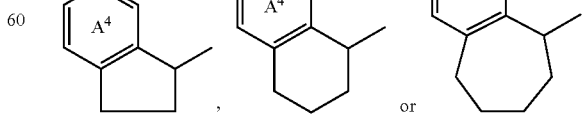

Xb¹ is preferably a bond.
Xc³ is preferably O.

A compound represented by the formula:

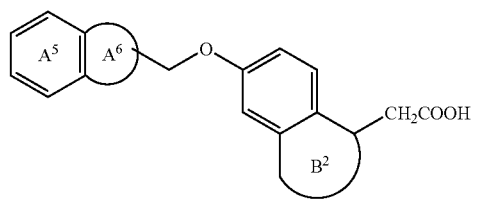

wherein ring $A^5$ is an optionally substituted benzene ring,
ring $A^6$ is an optionally substituted 5-membered heterocycle, and
ring $B^2$ is a 5- to 7-membered ring, or a salt thereof (hereinafter sometimes to be abbreviated as compound (I-3)).
Here,

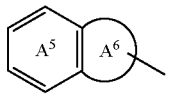

is preferably

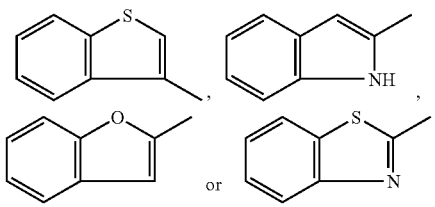

each optionally having substituent(s) selected from a halogen atom (e.g., chlorine atom) and an optionally halogenated $C_{1-6}$ alkyl group (e.g., methyl, trifluoromethyl).

As a salt of compounds (compound (I), compound (I'), compound (I-1), compound (I-2), compound (I-3), compound (I-4) and the like) used in the present invention, for example, metal salts, ammonium salts, salts with organic bases, salts with inorganic acids, salts with organic acids, salts with basic or acidic amino acids and the like can be mentioned.

Preferable examples of the metal salt include alkali metal salts such as sodium salt, potassium salt and the like; alkaline earth metal salts such as calcium salt, magnesium salt, barium salt and the like; aluminum salt, and the like.

Preferable examples of the salt with organic base include a salt with trimethylamine, triethylamine, pyridine, picoline, 2,6-lutidine, ethanolamine, diethanolamine, triethanolamine, cyclohexylamine, dicyclohexylamine, N,N'-dibenzylethylenediamine and the like.

Preferable examples of the salt with inorganic acid include a salt with hydrochloric acid, hydrobromic acid, nitric acid, sulfuric acid, phosphoric acid and the like.

Preferable examples of the salt with organic acid include a salt with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like.

Preferable examples of the salt with basic amino acid include a salt with arginine, lysine, ornithine and the like. Preferable examples of the salt with acidic amino acid include a salt with aspartic acid, glutamic acid and the like.

Of the above-mentioned salts, a pharmacologically acceptable salt is preferable.

The prodrug of the compounds or salts thereof (compound (I), compound (I'), compound (I-1), compound (I-2), compound (I-3), compound (I-4) etc.) (hereinafter sometimes to be abbreviated as the compound of the present invention) to be used in the present invention means a compound which is converted to the compound of the present invention with a reaction due to an enzyme, gastric acid, etc. under the physiological condition in the living body, that is, a compound which is converted to the compound of the present invention by enzymatic oxidation, reduction, hydrolysis, etc.; a compound which is converted to the compound of the present invention by hydrolysis etc. due to gastric acid, and the like.

A prodrug of the compound of the present invention may be a compound obtained by subjecting an amino group in the compound of the present invention to an acylation, alkylation or phosphorylation (e.g., a compound obtained by subjecting an amino group in the compound of the present invention to an eicosanoylation, alanylation, pentylaminocarbonylation, (5-methyl-2-oxo-1,3-dioxolen-4-yl)methoxycarbonylation, tetrahydrofuranylation, pyrrolidylmethylation, pivaloyloxymethylation and tert-butylation, etc.); a compound obtained by subjecting a hydroxy group in the compound of the present invention to an acylation, alkylation, phosphorylation or boration (e.g., a compound obtained by subjecting an hydroxy group in the compound of the present invention to an acetylation, palmitoylation, propanoylation, pivaloylation, succinylation, fumarylation, alanylation, dimethylaminomethylcarbonylation, etc.); a compound obtained by subjecting a carboxyl group in the compound of the present invention to an esterification or amidation (e.g., a compound obtained by subjecting a carboxyl group in the compound of the present invention to an ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification and methylamidation, etc.) and the like. Of these, a compound wherein the carboxy group in the compound of the present invention is esterified with a $C_{1-6}$ alkyl group such as methyl, ethyl, tert-butyl and the like is preferably used. Any of these compounds can be produced from the compound of the present invention by a method known per se.

A prodrug of the compound of the present invention may be a compound that converts to the compound of the present invention under physiological conditions as described in Development of Pharmaceutical Products, vol. 7, Molecule Design, 163-198, Hirokawa Shoten (1990).

Hereinafter the production methods of the compound of the present invention are explained.

Each symbol in the schematic drawings of the following reaction schemes is as defined above unless particularly described. Each compound described in the reaction schemes may form a salt as long as it does not inhibit the reaction, and as such salt, those similar to the salts of the compound used in the present invention can be mentioned.

The compound obtained in each reaction can be used in the form of a reaction mixture or a crude product for the next reaction. In addition, it can be isolated from a reaction mixture by a conventional method, and easily purified by conventional separation means (e.g., recrystallization, distillation, chromatography and the like).

Compound (I) (for example, compounds represented by the formulas (Ia), (Ia'), (Ib) and (Ib') (to be abbreviated as compound (Ia), compound (Ia'), compound (Ib), compound (Ib'), respectively)) can be produced, for example, according the method shown by the following Reaction Scheme 1 or a method analogous thereto.

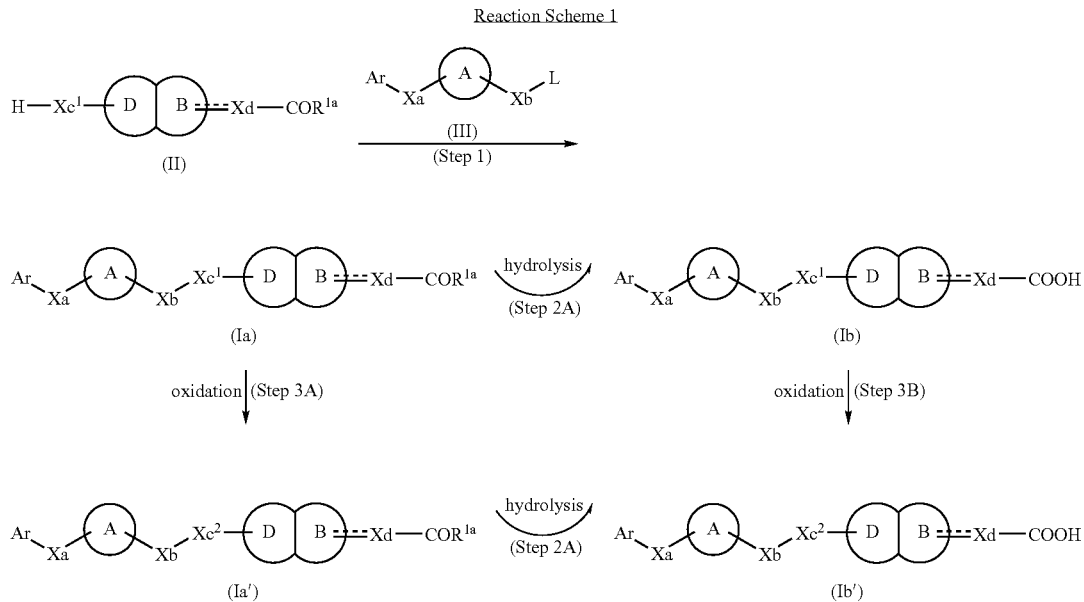

Reaction Scheme 1 wherein $Xc^1$ is O or S, $Xc^2$ is SO or $SO_2$, $R^{1a}$ is an optionally substituted $C_{1-6}$ alkoxy group, and L is a hydroxy group or a leaving group.

As the "leaving group" for L, for example, a halogen atom, an optionally halogenated $C_{1-6}$ alkylsulfonyloxy group (e.g., methanesulfonyloxy, ethanesulfonyloxy, trichloromethanesulfonyloxy, trifluoromethanesulfonyloxy), a $C_{6-10}$ arylsulfonyloxy group optionally having substituent(s) [e.g., $C_{6-10}$ arylsulfonyloxy group (e.g., phenylsulfonyloxy, naphthylsulfonyloxy) optionally having 1 to 3 substituent(s) selected from $C_{1-6}$ alkyl group, $C_{1-6}$ alkoxy group and nitro group, and the like; preferably phenylsulfonyloxy group, m-nitrophenylsulfonyloxy group, p-toluenesulfonyloxy group and the like], acyloxy group (e.g., trichloroacetoxy, trifluoroacetoxy) and the like can be mentioned.

<Step 1> Compound (Ia) can be produced by reacting a compound represented by the formula (II) with a compound represented by the formula (III) (abbreviated as compound (II) and compound (III), respectively).

(i) When L is a hydroxy group, compound (Ia) can be produced by subjecting compound (II) and compound (III) to Mitsunobu reaction (e.g., described in Synthesis, pages 1-27, 1981, and the like). In the reaction, compound (II) and compound (III) are reacted in the presence of azodicarboxylates such as diethyl azodicarboxylate, diisopropyl azodicarboxylate, 1,1'-(azodicarbonyl)dipiperidine and the like and phosphines such as triphenylphosphine, tributylphosphine and the like.

The amount of the azodicarboxylate and phosphine to be used is respectively about 1 to about 5 mol, preferably about 1 to about 2 mol, relative to 1 mol of compound (II).

The reaction is advantageously carried out using a solvent inert to the reaction. While the solvent is not particularly limited as long as the reaction proceeds, for example, solvents such as ethers (e.g., diethyl ether, diisopropyl ether, diphenyl ether, tetrahydrofuran, 1,4-dioxane, 1,2-dimethoxyethane and the like); aromatic hydrocarbons (e.g., benzene, toluene and the like); saturated hydrocarbons (e.g., cyclohexane, hexane and the like); amides (e.g., N,N-dimethylformamide, N,N-dimethylacetamide, hexamethylphosphoric triamide and the like); halogenated hydrocarbons (e.g., dichloromethane, chloroform, carbon tetrachloride, 1,2-dichloroethane and the like); nitriles (e.g., acetonitrile, propionitrile and the like); ketones (e.g., acetone, ethyl methyl ketone and the like); sulfoxides (e.g., dimethyl sulfoxide and the like) and the like, or a mixed solvent thereof and the like are preferable.

The amount of compound (III) to be used is about 0.5 to about 5 mol, preferably about 1 to about 2 mol, relative to 1 mol of compound (II).

The reaction time is generally 5 min. to 100 hrs., preferably 30 min. to 72 hrs. The reaction temperature is generally −20° C. to 200° C., preferably 0° C. to 100° C.

(ii) When L is a leaving group, compound (Ia) can be produced by reacting compound (II) with compound (III) in the presence of a base.

As the base, for example, alkali metal hydroxides such as lithium hydroxide, sodium hydroxide, potassium hydroxide and the like; alkaline earth metal hydroxides such as barium hydroxide and the like; alkali metal carbonates such as sodium carbonate, potassium carbonate, cesium carbonate and the like; alkali metal hydrogen carbonates such as sodium hydrogen carbonate and the like; acetates such as sodium acetate, ammonium acetate and the like; aromatic amines such as pyridine, lutidine and the like; tertiary amines such as triethylamine, tripropylamine, tributylamine, N-ethyldiisopropylamine, cyclohexyldimethylamine, 4-dimethylaminopyridine, N,N-dimethylaniline, N-methylpiperidine, N-methylpyrrolidine, N-methylmorpholine and the like; alkali metal hydrides such as sodium hydride, potassium hydride and the like; metal amides such as sodium amide, lithium diisopropylamide, lithium hexamethyldisilazide and the like; alkali metal alkoxides having 1 to 6 carbon atom(s) such as sodium methoxide, sodium ethoxide, sodium tert-butoxide, potassium tert-butoxide and the like, and the like can be mentioned.

The amount of the base to be used is about 1 to about 10 mol, preferably about 1 to about 3 mol, relative to 1 mol of compound (II).

The reaction is advantageously carried out using a solvent inert to the reaction. As the solvent, those similar to the solvents for the above-mentioned "when L is a hydroxy group" can be used.

The amount of compound (III) to be used is about 0.8 to about 10 mol, preferably about 0.9 to about 2 mol, relative to 1 mol of compound (II).

The reaction time is generally 10 min. to 12 hrs., preferably 20 min. to 6 hrs. The reaction temperature is generally −70° C. to 150° C., preferably −20° C. to 100° C.

<Step 2A> Compound (Ib) can be produced by subjecting compound (Ia) to hydrolysis.

The hydrolysis is carried out using an acid or a base according to a conventional method.

As the acid, for example, mineral acids (e.g., hydrochloric acid, sulfuric acid and the like); Lewis acids (e.g., boron trichloride, boron tribromide and the like); organic acids (e.g., trifluoroacetic acid, p-toluenesulfonic acid and the like) and the like can be mentioned. Lewis acid can be used concurrently with thiol or sulfide.

As the base, for example, alkali metal hydroxides (e.g., lithium hydroxide, sodium hydroxide, potassium hydroxide and the like); alkaline earth metal hydroxides (e.g., barium hydroxide and the like); alkali metal carbonates (e.g., sodium carbonate, potassium carbonate and the like); alkali metal alkoxides having 1 to 6 carbon atom(s) (e.g., sodium methoxide, sodium ethoxide, potassium tert-butoxide and the like); organic bases (including hydrate) (e.g., triethylamine, imidazole, formamidine and the like) and the like can be mentioned.

The amount of the acid and base to be used is about 0.5 to about 10 mol, preferably about 0.5 to about 6 mol, relative to 1 mol of compound (Ia).

The hydrolysis is carried out without solvent, or using a solvent inert to the reaction. While the solvent is not particularly limited as long as the reaction proceeds, for example, solvents such as alcohols (e.g., methanol, ethanol, propanol and the like); aromatic hydrocarbons (e.g., benzene, toluene and the like); saturated hydrocarbons (e.g., cyclohexane, hexane and the like); organic acids (e.g., formic acid, acetic acid and the like); ethers (e.g., tetrahydrofuran, dioxane, 1,2-dimethoxyethane and the like); amides (e.g., N,N-dimethylformamide, N,N-dimethylacetamide and the like); halogenated hydrocarbons (e.g., dichloromethane, chloroform, carbon tetrachloride, 1,2-dichloroethane and the like); nitrites (e.g., acetonitrile, propionitrile and the like); ketones (e.g., acetone, methylethylketone and the like); sulfoxides (e.g., dimethyl sulfoxide and the like); water and the like, a mixed solvent thereof and the like are preferable.

The reaction time is generally 10 min. to 100 hrs., preferably 10 min. to 24 hrs. The reaction temperature is generally −10° C. to 200° C., preferably 0° C. to 120° C.

<Step 3A> Compound (Ia') can be produced by subjecting compound (Ia) wherein $Xc^1$ is S to oxidation (e.g., described in Jikken Kagaku Koza, $4^{th}$ Ed., Vol. 24, pages 350-352 and 363-366, The Chemical Society of Japan ed., and the like).

Oxidation is generally conducted using an oxidizing agent according to a conventional method.

As the oxidizing agent, hydrogen peroxide, peracetic acid, sodium metaperiodate, potassium permanganate, sodium perborate, m-chloroperbenzoic acid (MCPBA), acyl nitrates, dinitrogen tetraoxide, halogens, N-bromosuccinimide (NBS), N-chlorosuccinimide (NCS) and the like can be mentioned.

The amount of the oxidizing agent to be used is about 0.5 to about 10 mol, preferably about 1 to about 5 mol, relative to 1 mol of compound (Ia).

The oxidation can be conducted without solvent, or using a solvent inert to the reaction. While the solvent is not particularly limited as long as the reaction proceeds, for example, solvents such as alcohols (e.g., methanol, ethanol, propanol and the like); aromatic hydrocarbons (e.g., benzene, toluene and the like); organic acids (e.g., acetic acid, trifluoroacetic acid and the like); halogenated hydrocarbons (e.g., dichloromethane, chloroform, carbon tetrachloride, 1,2-dichloroethane and the like); water and the like, a mixed solvent thereof and the like are preferable.

The reaction time is generally 10 min. to 100 hrs., preferably 10 min. to 24 hrs. The reaction temperature is generally −20° C. to 150° C., preferably 0° C. to 100° C.

<Step 2B> Compound (Ib') can be produced by subjecting a compound represented by the formula (Ia') to hydrolysis.

This reaction can be carried out in the same manner as in Step 2A, or a method analogous thereto.

<Step 3B> Compound (Ib') can be produced by subjecting a compound represented by the formula (Ib) (compound wherein $Xc^1$ is S) to oxidation.

The oxidation can be carried out in the same manner as in Step 3A, or a method analogous thereto.

Compound (II) to be used in Reaction Scheme 1 can be produced by, for example, a method described in J. Med. Chem., Vol. 39, pages 4928-4934, 1996; Bioorg. Med. Chem., Vol. 9, pages 1325-1335, 2001; Heterocycles, Vol. 41, pages 647-650, 1995; J. Med. Chem., Vol. 43, pages 2049-2063, 2000; J. Chem. Soc. Perkin Trans. 1, pages 2895-2900, 1996 and the like, or a method analogous thereto.

The compound (III) used in Reaction Scheme 1 can be obtained easily as a commercial product, or can also be produced by a method known per se.

For example, of compounds (III), compound (III') wherein Xa is —$(CH_2)_{k1}$-Q-$(CH_2)_{k2}$— (the symbols are as defined above) and Xb is Xba-$CH_2$ (Xba is a bond or a spacer having a main chain of 1 to 4 atom(s) (hereinafter sometimes to be abbreviated as compound (III')) can be produced by a method shown in Reaction Scheme 2, or a method analogous thereto.

As the "spacer having a main chain of 1 to 4 atom(s)" for Xba, a spacer having "a main chain of 1 to 4 atom(s)" is used from "spacers having a main chain of 1 to 5 carbon atom(s)" exemplarily shown for Xa.

Reaction Scheme 2

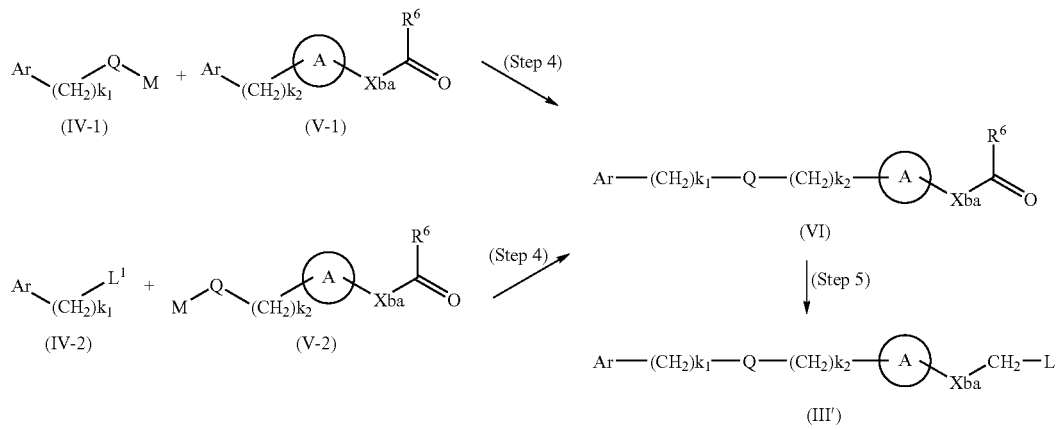

wherein $L^1$ is a leaving group, $R^6$ is a hydrogen atom or an optionally substituted $C_{1-6}$ alkoxy group, and M is a hydrogen atom or a metal (e.g., potassium, sodium, lithium, magnesium, copper, mercury, zinc, thallium, boron, tin and the like, which may be formed into a complex.

As the leaving group for $L^1$, those exemplarily shown for the aforementioned L can be used.

<Step 4> Compound (VI) can be produced by reacting (i) compound (IV-1) with compound (V-1), or (ii) compound (IV-2) with compound (V-2). In the following, compound (IV-1) and compound (IV-2) are generally referred to as compound (IV), unless otherwise specified, and compound (V-1) and compound (V-2) are generally referred to as compound (V), unless otherwise specified.

The reaction of compound (IV) with compound (V) is generally carried out in the presence of a base. As the base, alkali metal hydrides (e.g., sodium hydride, potassium hydride and the like); alkali metal hydroxides (e.g., lithium hydroxide, sodium hydroxide, potassium hydroxide and the like); alkaline earth metal hydroxides (e.g., magnesium hydroxide, calcium hydroxide and the like); alkali metal carbonates (e.g., sodium carbonate, potassium carbonate and the like); alkali metal hydrogen carbonates (e.g., sodium hydrogen carbonate, potassium hydrogen carbonate and the like); alkali metal alkoxides having 1 to 6 carbon atom(s) (e.g., sodium methoxide, sodium ethoxide, sodium tert-butoxide and the like); organic bases (e.g., trimethylamine, triethylamine, diisopropylethylamine, pyridine, picoline, N-methylpyrrolidine, N-methylmorpholine, 1,5-diazabicyclo[4.3.0]-5-nonene, 1,4-diazabicyclo[2.2.2]octane, 1,8-diazabicyclo[5.4.0]-7-undecene and the like); organic lithiums (e.g., methyllithium, n-butyllithium, sec-butyllithium, tert-butyllithium and the like); lithium amides (including hydrate) (e.g., lithium diisopropylamide and the like) and the like can be mentioned.

The reaction of compound (IV) with compound (V) is advantageously carried out using a solvent inert to the reaction. While the solvent is not particularly limited as long as the reaction proceeds, solvents such as alcohols (e.g., methanol, ethanol, propanol, isopropanol, butanol, tert-butanol and the like); ethers (e.g., dioxane, tetrahydrofuran, diethyl ether, tert-butyl methyl ether, diisopropyl ether, ethylene glycol-dimethyl ether and the like); esters (e.g., ethyl formate, ethyl acetate, n-butyl acetate and the like); halogenated hydrocarbons (e.g., dichloromethane, chloroform, carbon tetrachloride, trichloroethylene and the like); hydrocarbons (e.g., n-hexane, benzene, toluene and the like); amides (e.g., formamide, N,N-dimethylformamide, N,N-dimethylacetamide and the like); nitriles (e.g., acetonitrile, propionitrile and the like); sulfoxides (e.g., dimethyl sulfoxide and the like); sulfolane; hexamethylphosphoramide; water and the like, a mixed solvent thereof and the like are preferable.

The reaction of compound (IV) with compound (V) can be generally promoted by the use of a metal catalyst. As the metal catalyst, metal complexes having various ligands can be used and, for example, palladium compounds [e.g., palladium(II)acetate, tetrakis(triphenylphosphine)palladium(0), bis(triphenylphosphine)palladium(II)chloride, dichlorobis(triethylphosphine)palladium(0), tris(dibenzylideneacetone)dipalladium-2,2'-bis(diphenylphosphino)-1,1'-binaphthyl, a complex of palladium(II)acetate and 1,1'-bis(diphenylphosphino)ferrocene, and the like]; nickel compounds [e.g., tetrakis(triphenylphosphine)nickel(0), bis(triethylphosphine)nickel(II) chloride, bis(triphenylphosphine)nickel(II) chloride and the like]; rhodium compounds [e.g., tris(triphenylphosphine)rhodium(III) chloride and the like]; cobalt compounds; copper compounds [e.g., copper oxide, copper(II) chloride and the like]; platinum compounds and the like can be mentioned. Of these, palladium compounds, nickel compounds and copper compounds are preferable. The amount of the metal catalyst to be used is about 0.000001 to about 5 mol, preferably about 0.0001 to about 1 mol, relative to 1 mol of compound (IV). When a metal catalyst unstable to oxygen is used in this reaction, the reaction is preferably carried out in an inert gas (e.g., argon gas or nitrogen gas) stream.

The amount of compound (V) to be used is about 0.1 to about 10 mol, preferably about 0.5 to about 2 mol, relative to 1 mol of compound (IV). The amount of the base to be used is about 1 to about 20 mol, preferably about 1 to about 5 mol, relative to 1 mol of compound (IV).

The reaction temperature is about −10° C. to about 250° C., preferably about 0° C. to about 150° C. While the reaction time varies depending on the kinds of compound (IV), compound (V), metal catalyst, base and solvent, reaction temperature and the like, it is generally about 1 min. to about 200 hrs., preferably about 5 min. to about 100 hrs.

<Step 5> Compound (III') can be produced from compound (VI).

Compound (III') wherein L is a hydroxy group can be produced by subjecting compound (VI) to reduction.

The reduction is generally carried out using a reducing agent according to a conventional method.

As the reducing agent, for example, metal hydrides (e.g., aluminum hydride, diisobutylaluminum hydride, tributyltin hydride and the like); metal hydride complexes (e.g., sodium cyanoborohydride, sodium triacetoxyborohydride, sodium borohydride, lithium aluminum hydride and the like); borane complexes (e.g., borane tetrahydrofuran complex, borane dimethyl sulfide complex and the like); alkylboranes (e.g., thexylborane, disiamylborane and the like); diborane; metals (e.g., zinc, aluminum, tin, iron and the like); alkali metals (e.g., sodium, lithium and the like)/liquid ammonia (Birch reduction) and the like can be mentioned.

The amount of the reducing agent to be used is appropriately determined according to the kind of the reducing agent. For example, the amount of the metal hydride, metal hydride complex, borane complex, alkylborane or diborane to be used is about 0.25 to about 10 mol, preferably about 0.5 to about 5 mol, relative to 1 mol of compound (VI), respectively, and the amount of the metal (including alkali metal used for Birch reduction) to be used is about 1 to about 20 equivalents, preferably about 1 to about 5 equivalents, relative to 1 mol of compound (VI).

This reaction is advantageously carried out using a solvent inert to the reaction. While the solvent is not particularly limited as long as the reaction proceeds, for example, solvents such as alcohols (e.g., methanol, ethanol, 1-propanol, 2-propanol, tert-butyl alcohol and the like); ethers (e.g., diethyl ether, diisopropyl ether, diphenyl ether, tetrahydrofuran, 1,4-dioxane, 1,2-dimethoxyethane and the like); aromatic hydrocarbons (e.g., benzene, toluene and the like); saturated hydrocarbons (e.g., cyclohexane, hexane and the like); amides (e.g., N,N-dimethylformamide, N,N-dimethylacetamide, hexamethylphosphoric triamide and the like); organic acids (e.g., formic acid, acetic acid, propanoic acid, trifluoroacetic acid, ethanesulfonic acid and the like) and the like, a mixed solvent thereof and the like are preferable.

While the reaction time varies depending on the reagent and solvent to be used, it is generally 10 min. to 100 hrs., preferably 30 min. to 50 hrs. The reaction temperature is generally −20° C. to 100° C., preferably 0° C. to 80° C.

Compound (III') wherein L is a leaving group can be produced by reacting compound (III') wherein L is a hydroxy group with a halogenating agent or a sulfonylating agent.

As the halogenating agent, for example, thionyl chloride, phosphorus tribromide and the like can be used. Compound (III') wherein L is a halogen atom (e.g., chlorine, bromine and the like) can be produced by a reaction with a halogenating agent.

The reaction between compound (III') and a halogenating agent is generally carried out in a solvent that does not adversely affect the reaction. As the solvent that does not adversely affect the reaction, for example, halogenated hydrocarbons (e.g., dichloromethane, chloroform, carbon tetrachloride and the like); aromatic hydrocarbons (e.g., benzene, toluene, xylene and the like); ethers (e.g., diethyl ether, diisopropyl ether, tert-butyl methyl ether, tetrahydrofuran, dioxane, dimethoxyethane and the like); esters (e.g., methyl acetate, ethyl acetate, n-butyl acetate, tert-butyl acetate and the like) and the like can be mentioned. In addition, an excess amount of a halogenating agent may be used as a solvent.

The amount of the halogenating agent to be used is generally about 1 to about 10 mol relative to 1 mol of compound (III'). The reaction temperature is generally −20° C. to 100° C. The reaction time is generally 0.5 to 24 hrs.

As the sulfonylating agent, for example, methanesulfonyl chloride, benzenesulfonyl chloride, p-toluenesulfonyl chloride and the like can be used. Compound (III') wherein L is, for example, methanesulfonyloxy, benzenesulfonyloxy, p-toluenesulfonyloxy and the like can be produced by a reaction with a sulfonylating agent.

The amount of the sulfonylating agent to be used is generally about 1 to about 10 mol relative to 1 mol of compound (III').

The reaction between compound (III') and a sulfonylating agent is generally carried out in a solvent that does not adversely affect the reaction in the presence of a base. As the solvent that does not adversely affect the reaction, for example, halogenated hydrocarbons (e.g., dichloromethane, chloroform, carbon tetrachloride and the like); aromatic hydrocarbons (e.g., benzene, toluene, xylene and the like); ethers (e.g., diethyl ether, diisopropyl ether, tert-butyl methyl ether, tetrahydrofuran, dioxane, dimethoxyethane and the like); esters (e.g., methyl acetate, ethyl acetate, n-butyl acetate, tert-butyl acetate and the like) and the like can be mentioned.

As the base, for example, amines (e.g., triethylamine, N-methylmorpholine and the like); alkali metal salts (e.g., sodium hydrogen carbonate, potassium hydrogen carbonate, potassium carbonate and the like) and the like can be mentioned.

The amount of the base to be used is generally about 1 to about 10 mol relative to 1 mol of compound (III').

The reaction temperature is generally −20° C. to 100° C. The reaction time is generally 0.5 to 24 hrs.

Compound (I-2) can be produced, for example, according to the method shown by the following Reaction Scheme 3 or a method analogous thereto.

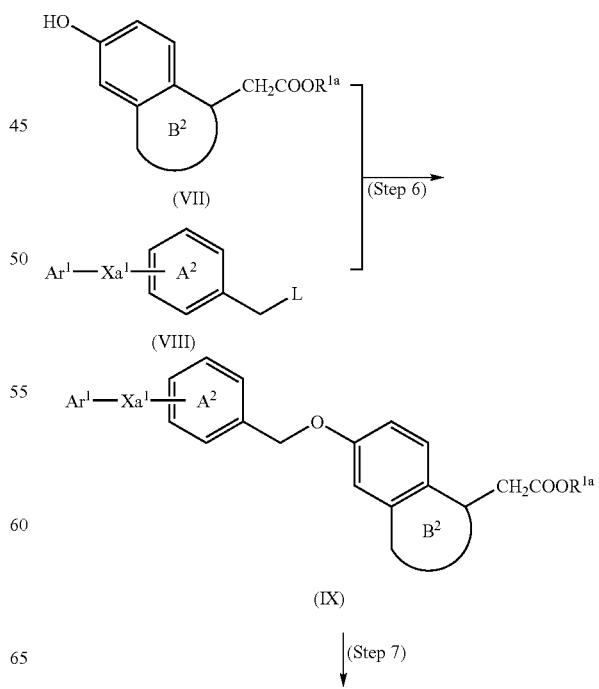

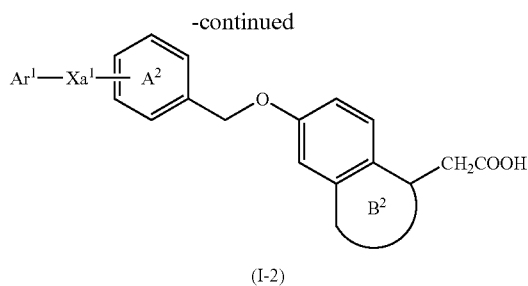

(I-2)

<Step 6> Compound (IX) can be produced in the same manner as in Step 1 from compound (VII) and compound (VIII).

The compound (VII) and compound (VIII) can be obtained easily as commercial products, or can also be produced by a method known per se, or a method analogous thereto.

<Step 7> Compound (I-2) can be produced in the same manner as in Step 2A from compound (IX).

Compound (I-4) can be produced, for example, according to the method shown by the following Reaction Scheme 4 or a method analogous thereto.

<Step 8> Compound (XI) can be produced in the same manner as in Step 1 from compound (VII) and compound (X).

The compound (X) can be obtained easily as a commercial product, or can also be produced by a method known per se, or a method analogous thereto.

<Step 9> Compound (I-4) can be produced in the same manner as in Step 2A from compound (XI).

Of compounds (I-4), a compound wherein $Xa^2$ is $-N(R^5)-(CH_2)m-$ can be also produced, for example, according to the method shown by the following Reaction Scheme 5 or a method analogous thereto.

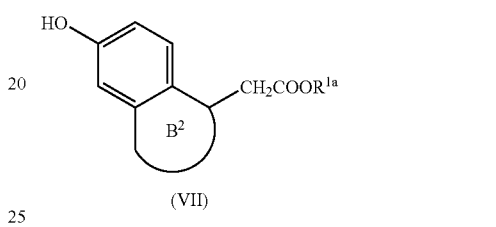

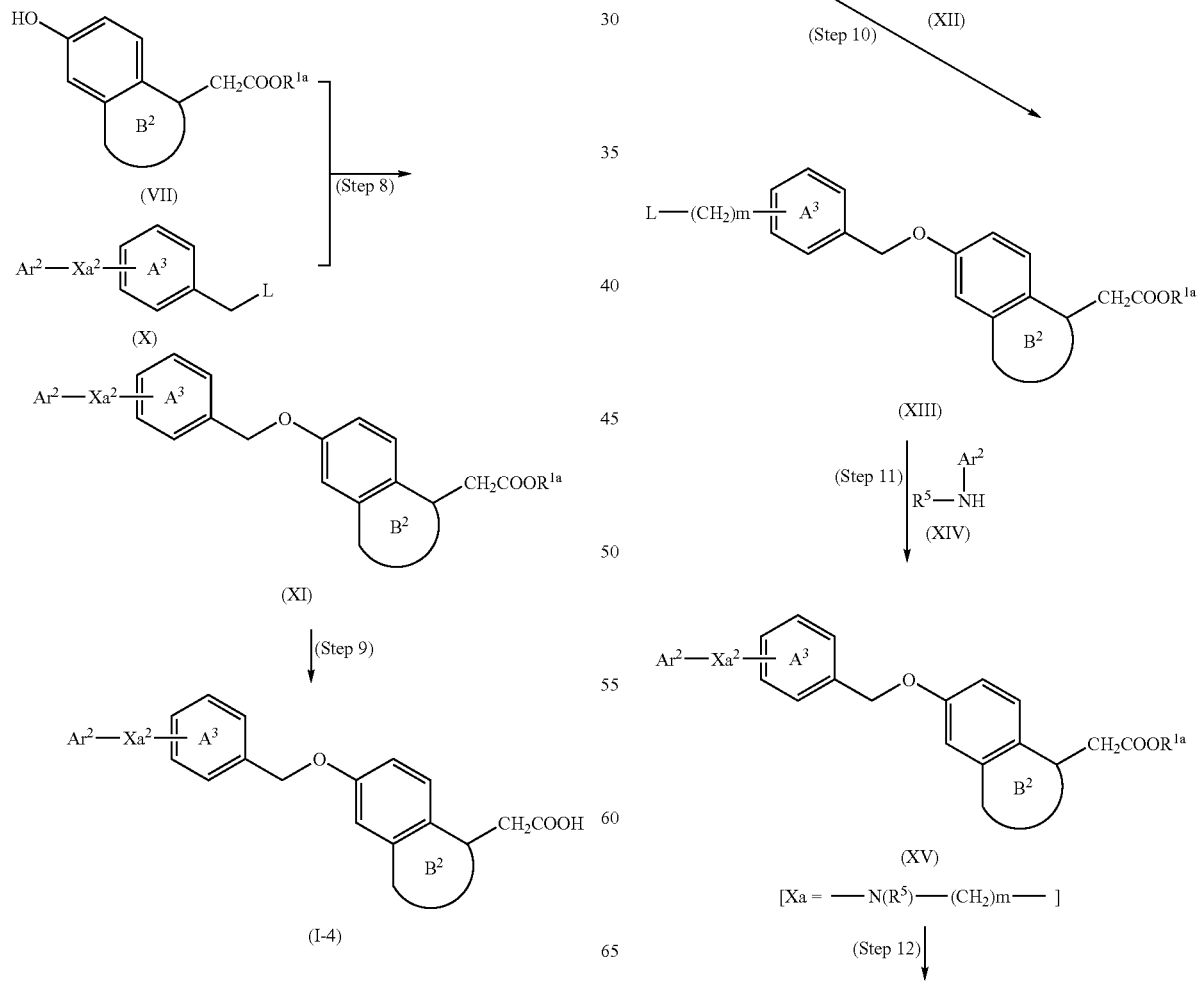

-continued

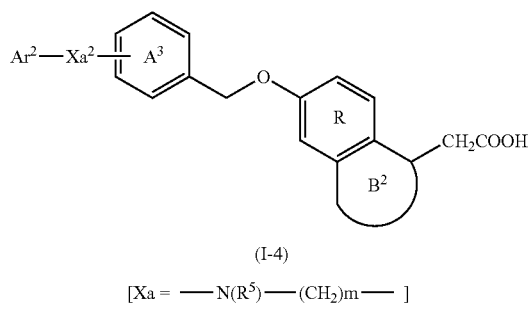

(I-4)

[Xa = —N(R⁵)—(CH₂)m—]

<Step 10> Compound (XIII) can be produced in the same manner as in Step 1 from compound (VII) and compound (XII).

<Step 11> Of compounds (XV), a compound wherein Xa is —N(R⁵)—(CH₂)m- can be also produced in the same manner as in Step 4 from compound (XIII) and compound (XIV).

The compounds (XII) and (XIV) can be obtained easily as commercial products, or can also be produced by a method known per se or a method analogous thereto.

<Step 12> Of compounds (I-4), a compound wherein Xa is —N(R⁵)—(CH₂)m- can be produced in the same manner as in Step 2A from compound (XV) wherein Xa is —N(R⁵)—(CH₂)m-.

Production methods of compound (I-1) and compound (I-3) are explained in the following.

Compound (I-1) can be produced, for example, according to the method shown by the following Reaction Scheme 6 or a method analogous thereto.

The compounds (XVI), (XVII), (XVIII) and (XIX) can be obtained easily as commercial products, or can also be produced by a method known per se or a method analogous thereto.

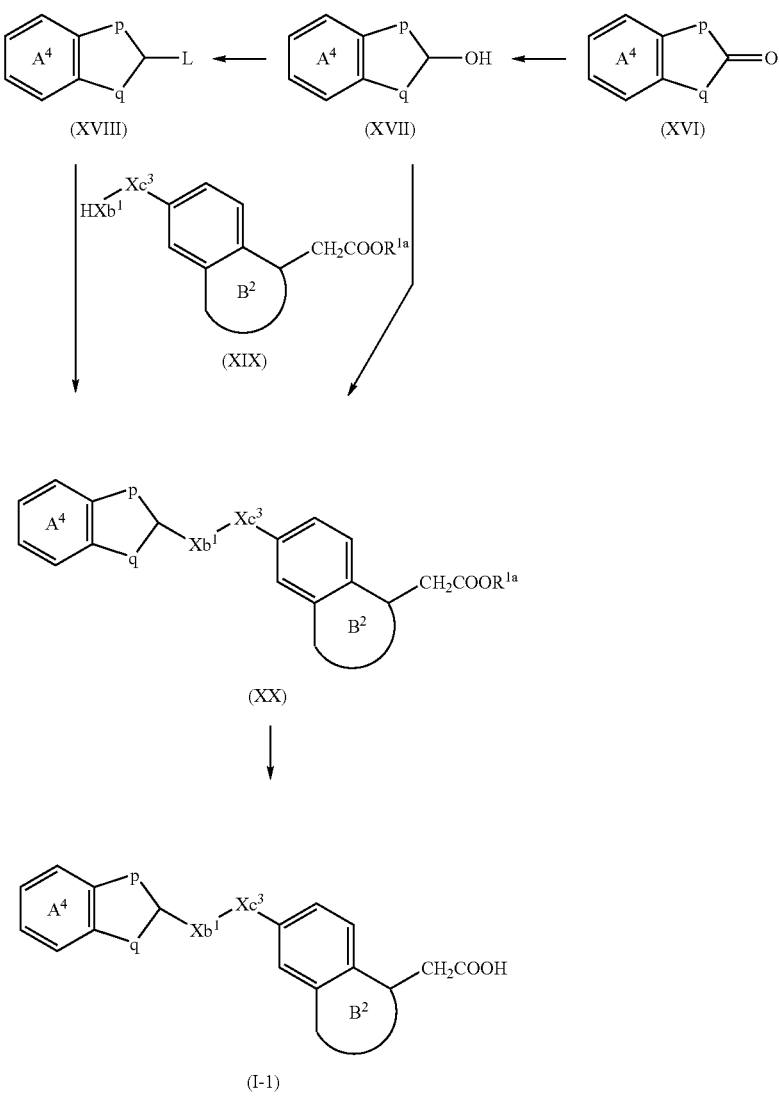

Compound (XVII) can be produced by reducing the carbonyl group of compound (XVI).

As the reducing agent to be used for the reduction, those exemplarily shown in the aforementioned step 5 can be mentioned. The amount of the reducing agent to be used is, for example, about 1 to about 10 mol, preferably about 1 to about 5 mol, per 1 mol of compound (XVI) for metal hydride and metal hydride complex, about 1 to about 10 mol, preferably about 1 to about 5 mol, per 1 mol of compound (XVI) for borane complex, alkylborane and diborane, and about 1 to about 20 equivalents, preferably about 1 to about 5 equivalents, per 1 mol of compound (XVI) for metal. When desired, Lewis acids may be used for this reaction. As the "Lewis acids", for example, aluminum chloride, aluminum bromide, titanium(IV) chloride, tin(II) chloride, zinc chloride, boron trichloride, boron tribromide, boron trifluoride and the like can be used. The amount of the Lewis acid to be used is about 1 to about 10 mol, preferably about 1 to about 5 mol, relative to 1 mol of compound (XVI).

The compound can also be reduced by hydrogenation. In this case, for example, catalysts such as palladium on carbon, platinum(IV) oxide, Raney nickel, Raney cobalt etc., and the like can be used. The amount of the catalyst to be used is about 5 to about 1000 wt %, preferably about 10 to about 300 wt %, relative to 1 mol of compound (XVI). Various hydrogen sources can also be used instead of gaseous hydrogen. As the "hydrogen source", formic acid, ammonium formate, triethylammonium formate, sodium phosphinate, hydrazine and the like can be used. The amount of the hydrogen source to be used is about 1 to about 10 mol, preferably about 1 to about 5 mol, relative to 1 mol of compound (XVI).

This reaction is advantageously carried out using a solvent inert to the reaction. While the solvent is not particularly limited as long as the reaction proceeds, for example, solvents such as alcohols (e.g., methanol, ethanol, 1-propanol, 2-propanol, tert-butyl alcohol and the like), ethers (e.g., diethyl ether, diisopropyl ether, diphenyl ether, tetrahydrofuran, 1,4-dioxane, 1,2-dimethoxyethane and the like), hydrocarbons (e.g., benzene, toluene, cyclohexane, hexane and the like), amides (e.g., N,N-dimethylformamide, N,N-dimethylacetamide, hexamethylphosphoric triamide and the like), organic acids (e.g., formic acid, acetic acid, propionic acid, trifluoroacetic acid, methanesulfonic acid and the like) and the like, a mixed solvent thereof and the like are preferable.

While the reaction time varies depending on the kind and amount of the reducing agent or the activity and amount of the catalyst, it is generally about 1 hr to about 100 hrs., preferably about 1 hr to about 50 hrs. The reaction temperature is generally about $-20°$ C. to about $120°$ C., preferably about $0°$ C. to about $80°$ C. When a hydrogenation catalyst is used, the pressure of hydrogen is generally about 1 to about 100 atm.

Compound (XVIII) can be produced by converting hydroxy group of compound (XVII) to a "leaving group".

When the "leaving group" for L is a halogen atom, as the halogenating agent to be used for halogenation, for example, thionyl halides (e.g., thionyl chloride, thionyl bromide and the like), phosphoryl halides (e.g., phosphoryl chloride, phosphoryl bromide and the like), phosphorus halides (phosphorus pentachloride, phosphorus trichloride, phosphorus pentabromide, phosphorus tribromide and the like), oxalyl halides (e.g., oxalyl chloride and the like), phosgene and the like can be mentioned. The halogenating agent is used in a proportion of about 0.1 to about 30 mol, preferably about 0.2 to about 10 mol, relative to 1 mol of compound (XVII).

This reaction is carried out in the presence of a base, where desired. As the "base", tertiary amines such as triethylamine, tripropylamine, tributylamine, N-ethyldiisopropylamine, cyclohexyldimethylamine, 4-dimethylaminopyridine, N,N-dimethylaniline, N-methylpiperidine, N-methylpyrrolidine, N-methylmorpholine and the like, and the like can be mentioned. The base is used in a proportion of about 1 to about 20 mol, preferably about 1 to about 10 mol, relative to 1 mol of compound (XVII).

This reaction is advantageously carried out without solvent, or using a solvent inert to the reaction. While the solvent is not particularly limited as long as the reaction proceeds, for example, solvents such as hydrocarbons (e.g., benzene, toluene, cyclohexane, hexane and the like), ethers (e.g., diethyl ether, diisopropyl ether, diphenyl ether, tetrahydrofuran, 1,4-dioxane, 1,2-dimethoxyethane and the like), amides (e.g., N,N-dimethylformamide, N,N-dimethylacetamide, hexamethylphosphoric triamide and the like), halogenated hydrocarbons (e.g., dichloromethane, chloroform, carbon tetrachloride, 1,2-dichloroethane and the like) and the like, a mixed solvent thereof and the like are preferable.

The reaction time is generally about 10 min. to about 12 hrs., preferably about 10 min. to about 5 hrs. The reaction temperature is generally about $-10°$ C. to about $200°$ C., preferably about $-10°$ C. to about $120°$ C.

When the "leaving group" for L is an optionally halogenated $C_{1-6}$ alkylsulfonyloxy group or a $C_{6-10}$ arylsulfonyloxy group optionally having substituent(s), as the sulfonylating agent, for example, $C_{1-6}$ alkylsulfonyl halides (e.g., methanesulfonyl chloride and the like), $C_{6-10}$ arylsulfonyl halides (e.g., benzenesulfonyl chloride, p-toluenesulfonyl chloride and the like) and the like can be mentioned. The sulfonylating agent is used in a proportion of about 1 to about 20 mol, preferably about 1 to about 10 mol, relative to 1 mol of compound (XVII).

This reaction is advantageously carried out without solvent, or using a solvent inert to the reaction. While the solvent is not particularly limited as long as the reaction proceeds, for example, solvents such as hydrocarbons (e.g., benzene, toluene, cyclohexane, hexane and the like), ethers (e.g., diethyl ether, diisopropyl ether, diphenyl ether, tetrahydrofuran, 1,4-dioxane, 1,2-dimethoxyethane and the like), halogenated hydrocarbons (e.g., dichloromethane, chloroform, carbon tetrachloride, 1,2-dichloroethane and the like), esters (methyl acetate, ethyl acetate, butyl acetate and the like) and the like, a mixed solvent thereof and the like are preferable.

This reaction is carried out in the presence of a base, where desired. As the "base", tertiary amines (e.g., triethylamine, tripropylamine, tributylamine, N-ethyldiisopropylamine, cyclohexyldimethylamine, 4-dimethylaminopyridine, N,N-dimethylaniline, N-methylpiperidine, N-methylpyrrolidine, N-methylmorpholine and the like), inorganic bases (e.g., sodium hydroxide, potassium hydroxide, lithium hydroxide, barium hydroxide and the like), basic salts (e.g., sodium carbonate, potassium carbonate, cesium carbonate, sodium hydrogen carbonate, sodium acetate, ammonium acetate and the like) and the like can be mentioned. The base is used in a proportion of about 1 to about 20 mol, preferably about 1 to about 10 mol, relative to 1 mol of compound (XVII).

The reaction time is generally about 10 min. to about 12 hrs., preferably about 10 min. to about 5 hrs. The reaction temperature is generally about $-30°$ C. to about $150°$ C., preferably about $-20°$ C. to about $100°$ C.

Compound (XX) wherein $Xb^1$-$Xc^3$ is an oxygen atom or a sulfur atom can be produced by condensing compound (XVIII) with compound (XIX) in the presence of a base.

As the base to be used for this reaction, inorganic bases (e.g., sodium hydroxide, potassium hydroxide, lithium hydroxide, barium hydroxide and the like), basic salts (e.g., sodium carbonate, potassium carbonate, cesium carbonate, sodium hydrogen carbonate, sodium acetate, ammonium acetate and the like), aromatic amines (e.g., pyridine, lutidine and the like), tertiary amines (e.g., triethylamine, tripropylamine, tributylamine, N-ethyldiisopropylamine, cyclohexyldimethylamine, 4-dimethylaminopyridine, N,N-dimethylaniline, N-methylpiperidine, N-methylpyrrolidine, N-methylmorpholine and the like), alkali metal hydrides (e.g., sodium hydride, potassium hydride and the like), metal amides (e.g., sodium amide, lithium diisopropylamide, lithium hexamethyldisilazide and the like), metal alkoxides (e.g., sodium methoxide, sodium ethoxide, sodium tert-butoxide, potassium tert-butoxide and the like) and the like can be mentioned. The base is used in a proportion of about 1 to 10 mol, preferably about 1 to 3 mol, relative to 1 mol of compound (XVIII).

This reaction is advantageously carried out using a solvent inert to the reaction. While the solvent is not particularly limited as long as the reaction proceeds, for example, solvents such as alcohols (e.g., methanol, ethanol, 1-propanol, 2-propanol, tert-butyl alcohol and the like), ethers (e.g., diethyl ether, diisopropyl ether, diphenyl ether, tetrahydrofuran, 1,4-dioxane, 1,2-dimethoxyethane and the like), hydrocarbons (e.g., benzene, toluene, cyclohexane, hexane and the like), amides (e.g., N,N-dimethylformamide, N,N-dimethylacetamide, hexamethylphosphoric triamide and the like), halogenated hydrocarbons (dichloromethane, chloroform, carbon tetrachloride, 1,2-dichloroethane and the like), nitriles (e.g., acetonitrile, propionitrile and the like), esters (e.g., methyl acetate, ethyl acetate, butyl acetate and the like), sulfoxides (e.g., dimethyl sulfoxide and the like), water and the like, a mixed solvent thereof and the like are preferable.

The reaction time is generally about 10 min. to about 12 hrs., preferably about 20 min. to about 6 hrs. The reaction temperature is generally about −50° C. to about 150° C., preferably about −20° C. to about 100° C.

Compound (XX) wherein $Xb^1$-$Xc^3$ is an oxygen atom or a sulfur atom can also be produced by condensing compound (XVII) with compound (XIX) in the presence of a dehydrating agent, where desired.

As the dehydrating agent that can be used for this reaction, for example, acidic catalysts (e.g., hydrochloric acid, sulfuric acid, phosphoric acid, potassium hydrogen sulfate, oxalic acid, p-toluenesulfonic acid, 10-camphorsulfonic acid, boron trifluoride ether complex and the like), basic catalysts (e.g., sodium hydroxide, potassium hydroxide and the like) and the like can be mentioned. Furthermore, for example, carbodiimides (e.g., N,N'-dicyclohexylcarbodiimide and the like), alumina, sodium dioxide, phosphorus oxychloride, thionyl chloride, methanesulfonyl chloride and the like may be used. These acids and bases are used in a proportion of about 0.1 to 10 mol, preferably about 0.1 to 5.0 mol, relative to 1 mol of compound (XIX).

This reaction is advantageously carried out without solvent, or using a solvent inert to the reaction. While the solvent is not particularly limited as long as the reaction proceeds, for example, solvents such as alcohols (e.g., methanol, ethanol, propanol and the like), ethers (e.g., diethyl ether, tetrahydrofuran, dioxane, 1,2-dimethoxyethane and the like), organic acids (e.g., formic acid, acetic acid and the like), hydrocarbons (e.g., benzene, toluene, cyclohexane, hexane and the like), amides (e.g., N,N-dimethylformamide, N,N-dimethylacetamide and the like), sulfoxides (e.g., dimethyl sulfoxide and the like) and the like, a mixed solvent thereof and the like are preferable.

The reaction time is generally 30 min. to 24 hrs., preferably 30 min. to 5 hrs. The reaction temperature is generally 0° C. to 200° C., preferably 0° C. to 150° C.

Compound (XX) wherein $Xb^1$-$Xc^3$ is an oxygen atom can also be produced by subjecting compound (XVII) and compound (XIX) to Mitsunobu reaction.

This reaction is carried out in the same manner as in the aforementioned Step 1.

Compound (I-1) can be produced in the same manner as in Step 2A from compound (XX).

Compound (I-3) of the present invention can be produced, for example, according to the method shown by the following Reaction Scheme 7 or a method analogous thereto.

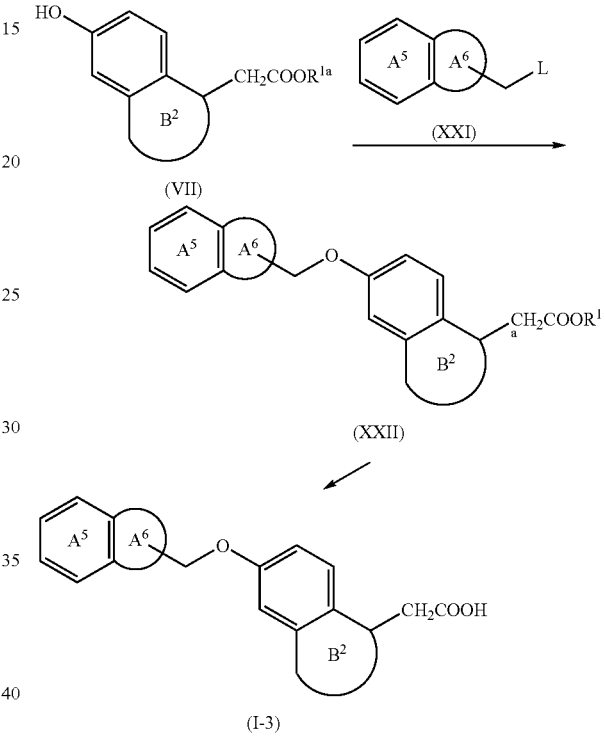

The compound (XXI) can be obtained easily as commercial products, or can also be produced by a method known per se or a method analogous thereto.

Compound (XXII) can be produced in the same manner as in Step 1 from compound (VII) and compound (XXI).

Compound (I-3) can be produced in the same manner as in Step 2A from compound (XXII).

In each of the aforementioned reactions, when the starting compound has amino group, carboxyl group, hydroxy group or mercapto group as a substituent, a protecting group generally used in peptide chemistry and the like may be introduced into these groups. By removing the protecting group as necessary after the reaction, the objective compound can be obtained.

As the amino-protecting group, for example, formyl group; $C_{1-6}$ alkyl-carbonyl group (e.g., acetyl, propionyl and the like), benzoyl group, $C_{1-6}$ alkoxy-carbonyl group (e.g., methoxycarbonyl, ethoxycarbonyl, tert-butoxycarbonyl (Boc) and the like), allyloxycarbonyl group (Aloc), phenyloxycarbonyl group, fluorenylmethyloxycarbonyl group (Fmoc), $C_{7-10}$ aralkyloxy-carbonyl group (e.g., benzyloxycarbonyl and the like), trityl group, phthaloyl group, dithiasuccinoyl group, N,N-dimethylaminomethylene group, each optionally having substituent(s), and the like can be used. As the substituent, for example, phenyl group, halogen atom, $C_{1-6}$ alkyl-carbonyl group (e.g., acetyl, propionyl, valeryl and the like), optionally halogenated $C_{1-6}$ alkoxy group, nitro group and the like are used. The number of the substituent(s) is about 1 to 3.

As the carboxyl-protecting group, for example, $C_{1-6}$ alkyl group, allyl group, benzyl group, phenyl group, trityl group, trialkylsilyl group, each optionally having substituent(s), and the like can be used. As the substituent, for example, halogen atom, formyl group, $C_{1-6}$ alkyl-carbonyl group (e.g., acetyl, propionyl, butylcarbonyl and the like), optionally halogenated $C_{1-6}$ alkoxy group, nitro group, $C_{1-6}$ alkyl group, $C_{6-10}$ aryl group (e.g., phenyl, naphthyl and the like) and the like are used. The number of the substituent(s) is about 1 to 3.

As the hydroxy-protecting group, for example, formyl group, or $C_{1-6}$ alkyl group, $C_{7-10}$ aralkyl group, $C_{1-6}$ alkyl-carbonyl group (e.g., acetyl, propionyl and the like), benzoyl group, phenyloxycarbonyl group, $C_{7-10}$ aralkyloxy-carbonyl group (e.g., benzyloxycarbonyl and the like), $C_{7-10}$ aralkyl-carbonyl group (e.g., benzylcarbonyl and the like), tetrahydropyranyl group, tetrahydrofuranyl group, furanyl group, silyl group, each optionally having substituent(s), and the like can be used. As the substituent, for example, halogen atom, $C_{1-6}$ alkyl group, $C_{7-10}$ aralkyl group (e.g., benzyl and the like), $C_{6-10}$ aryl group (e.g., phenyl, naphthyl and the like), $C_{1-6}$ alkoxy group, nitro group and the like are used. The number of the substituent(s) is about 1 to 4.

As the mercapto-protecting group, for example, $C_{1-6}$ alkyl group, $C_{7-20}$ aralkyl group (e.g., benzyl, trityl), each optionally having substituent(s), and the like can be mentioned. As the substituent, for example, halogen atom, $C_{1-6}$ alkyl group, phenyl group, $C_{7-10}$ aralkyl group (e.g., benzyl and the like), $C_{1-6}$ alkoxy group, nitro group and the like are used. The number of the substituent(s) is about 1 to 4.

For elimination of the protecting group, a method known per se or a method analogous thereto is used. For example, treatment with acid, base, ultraviolet rays, hydrazine, phenylhydrazine, sodium N-methyldithiocarbamate, tetrabutylammonium fluoride, palladium(II)acetate and the like or reduction are used.

In each of the above-mentioned reaction steps, where desired, the compound of the present invention can be synthesized by further using hydrolysis, deprotection, acylation, alkylation, hydrogenation, oxidation, reduction, carbon chain extension and substituent exchange reaction alone or in a combination of two or more thereof. For these reactions, for example, the methods described in Shin Jikken Kagaku Koza, Vols. 14 and 15, 1977 (Maruzen Press) and the like are employed.

When the object product is obtained in a free form by the above-mentioned reactions, the product may be converted to a salt by a conventional method, and when it is obtained as a salt, the product may be converted to a free form or a different salt by a conventional method. The compound of the present invention thus obtained can be isolated and purified from a reaction mixture by a known means, such as, phase transfer, concentration, solvent extraction, fractionation, crystallization, recrystallization, chromatography and the like.

When the compound of the present invention is present as a configurational isomer (stereoisomer), diastereomer, conformer or the like, each can be isolated by the above separation and purification methods on demand. In addition, when the compound of the present invention is in the form of racemates, they can be separated into S- and R-forms by any conventional optical resolution.

When the compound of the present invention includes stereoisomers, both the isomers alone and mixtures of each isomers are included in the scope of the present invention.

In addition, the compound of the present invention may be a hydrate or non-hydrate.

The compound of the present invention may be labeled with an isotope (e.g., $^{3}H$, $^{14}C$, $^{35}S$ and the like) or the like.

Since the compound of the present invention and a prodrug thereof have a GPR40 receptor function modulating action, particularly, a GPR40 receptor agonist activity, show low toxicity and fewer side effects, they are useful as safe GPR40 receptor function modulators, preferably GPR40 agonists.

The compound of the present invention and a prodrug thereof show a superior GPR40 receptor function modulating action in mammals (e.g., mouse, rat, hamster, rabbit, cat, dog, bovine, sheep, monkey, human etc.), and are useful as modulators of physiological function in which GPR40 receptor is involved or agents for the prophylaxis or treatment of disease state or disease in which GPR40 receptor is involved.

To be specific, the compound of the present invention and a prodrug thereof are useful as insulin secretion modulators (preferably insulin secretagogues), hypoglycemic drugs and pancreatic β cell protectors.

Particularly, the compound of the present invention and a prodrug thereof are useful as blood glucose level-dependent insulin secretagogues based on the GPR40 receptor agonist activity thereof. That is, different from sulfonylurea, the compound of the present invention and a prodrug thereof are useful as insulin secretagogues that do not cause hypoglycemia.

Moreover, the compound of the present invention and a prodrug thereof are useful as agents for the prophylaxis or treatment of diseases such as diabetes, impaired glucose tolerance, ketosis, acidosis, diabetic neuropathy, diabetic nephropathy, diabetic retinopathy, hyperlipidemia, genital disorder, skin disease, arthropathy, osteopenia, arteriosclerosis, thrombotic disease, dyspepsia, memory and learning disorder, obesity, hypoglycemia, hypertension, edema, insulin resistance, unstable diabetes, fatty atrophy, insulin allergy, insulinoma, lipotoxicity, hyperinsulinemia, cancer and the like; particularly, diseases such as diabetes, impaired glucose tolerance, ketosis, acidosis, diabetic neuropathy, diabetic nephropathy, diabetic retinopathy, hyperlipidemia, genital disorder, skin disease, arthropathy, osteopenia, arteriosclerosis, thrombotic disease, dyspepsia, memory and learning disorder and the like. Here, diabetes includes insulin-dependent (type I) diabetes, non-insulin-dependent (type II) diabetes and gestational diabetes. In addition, hyperlipidemia includes hypertriglyceridemia, hypercholesterolemia, hypo-high-density-lipoproteinemia, postprandial hyperlipidemia and the like.

For diagnostic criteria of diabetes, Japan Diabetes Society reported new diagnostic criteria in 1999.

According to this report, diabetes is a condition showing any of a fasting blood glucose level (glucose concentration of intravenous plasma) of not less than 126 mg/dl, a 75 g oral glucose tolerance test (75 g OGTT) 2 h level (glucose concentration of intravenous plasma) of not less than 200 mg/dl, and a non-fasting blood glucose level (glucose concentration of intravenous plasma) of not less than 200 mg/dl. A condition not falling under the above-mentioned diabetes and different from "a condition showing a fasting blood glucose level (glucose concentration of intravenous plasma) of less than 110 mg/dl or a 75 g oral glucose tolerance test (75 g OGTT) 2 h level (glucose concentration of intravenous plasma) of less than 140 mg/dl" (normal type) is called a "borderline type".

In addition, ADA (American Diabetes Association) reported new diagnostic criteria of diabetes in 1997 and WHO in 1998.

According to these reports, diabetes is a condition showing a fasting blood glucose level (glucose concentration of intravenous plasma) of not less than 126 mg/dl and a 75 g oral glucose tolerance test 2 h level (glucose concentration of intravenous plasma) of not less than 200 mg/dl.

According to the above-mentioned reports, impaired glucose tolerance is a condition showing a fasting blood glucose level (glucose concentration of intravenous plasma) of less than 126 mg/dl and a 75 g oral glucose tolerance test 2 h level (glucose concentration of intravenous plasma) of not less than 140 mg/dl and less than 200 mg/dl. According to the report of ADA, a condition showing a fasting blood glucose level (glucose concentration of intravenous plasma) of not less than 110 mg/dl and less than 126 mg/dl is called IFG (Impaired Fasting Glucose). According to the report of WHO, among the IFG (Impaired Fasting Glucose), a condition showing a 75 g oral glucose tolerance test 2 h level (glucose concentration of intravenous plasma) of less than 140 mg/dl is called IFG (Impaired Fasting Glycemia).

The compound of the present invention or a prodrug thereof can be also used as an agent for the prophylaxis or treatment of diabetes, borderline type, impaired glucose tolerance, IFG (Impaired Fasting Glucose) and IFG (Impaired Fasting Glycemia), as determined according to the above-mentioned new diagnostic criteria. Moreover, the compound of the present invention can prevent progress of borderline type, impaired glucose tolerance, IFG (Impaired Fasting Glucose) or IFG (Impaired Fasting Glycemia) into diabetes.

The compound of the present invention and a prodrug thereof show low toxicity, and can be safely administered orally or parenterally (e.g., topical, rectal, intravenous administration etc.) in the form of the compound of the present invention or a prodrug thereof as it is or after admixing with a pharmacologically acceptable carrier to give a pharmaceutical preparation such as tablets (including sugar-coated tablets and film-coated tablets), powders, granules, capsules (including soft capsules), liquids, injections, suppositories, sustained-release agents and the like, according to a method known per se employed for general production methods for pharmaceutical preparations.

The content of the compound of the present invention in a pharmaceutical preparation is about 0.01 to about 100% by weight relative to the whole preparation. While the dose varies depending on the administration subject, administration route, diseases, condition and the like, for example, the compound of the present invention (as an active ingredient) can be orally administered to an adult patient with diabetes (body weight about 60 kg) in about 0.01 to about 30 mg/kg body weight per day, preferably about 0.1 to about 20 mg/kg body weight per day, more preferably about 1 to about 20 mg/kg body weight per day, which may be given at once or in several portions a day.

As the pharmacologically acceptable carrier that may be used for the production of the pharmaceutical agent of the present invention, various organic or inorganic carrier substances conventionally used as a preparation material can be mentioned. For example, excipient, lubricant, binder and disintegrant for solid preparations, solvent, dissolution aids, suspending agent, isotonicity agent, buffer and soothing agent for liquid preparations and the like can be mentioned. Where necessary, conventional additives such as preservatives, antioxidants, coloring agents, sweetening agents, adsorbing agents, wetting agents and the like can be used as appropriate in suitable amounts.

As the excipient, for example, lactose, sucrose, D-mannitol, starch, corn starch, crystalline cellulose, light anhydrous silicic acid and the like can be mentioned.

As the lubricant, for example, magnesium stearate, calcium stearate, talc, colloidal silica and the like can be mentioned.

As the binder, for example, crystalline cellulose, sucrose, D-mannitol, dextrin, hydroxypropylcellulose, hydroxypropylmethylcellulose, polyvinylpyrrolidone, starch, saccharose, gelatin, methylcellulose, carboxymethylcellulose sodium and the like can be mentioned.

As the disintegrant, for example, starch, carboxymethylcellulose, carboxymethylcellulose calcium, carboxymethylstarch sodium, L-hydroxypropylcellulose and the like can be mentioned.

As the solvent, for example, water for injection, alcohol, propylene glycol, macrogol, sesame oil, corn oil, olive oil and the like can be mentioned.

As the dissolution aids, for example, polyethylene glycol, propylene glycol, D-mannitol, benzyl benzoate, ethanol, trisaminomethane, cholesterol, triethanolamine, sodium carbonate, sodium citrate and the like can be mentioned.

As the suspending agent, for example, surfactants such as stearyltriethanolamine, sodium lauryl sulfate, lauryl aminopropionate, lecithin, benzalkonium chloride, benzethonium chloride, glycerol monostearate and the like; hydrophilic polymers such as polyvinyl alcohol, polyvinylpyrrolidone, carboxymethylcellulose sodium, methylcellulose, hydroxymethylcellulose, hydroxyethylcellulose, hydroxypropylcellulose and the like, and the like can be mentioned.

As the isotonicity agent, for example, glucose, D-sorbitol, sodium chloride, glycerin, D-mannitol and the like can be mentioned.

As the buffer, for example, buffers such as phosphate, acetate, carbonate, citrate and the like, and the like can be mentioned.

As the soothing agent, for example, benzyl alcohol and the like can be mentioned.

As the preservative, for example, p-hydroxybenzoates, chlorobutanol, benzyl alcohol, phenethyl alcohol, dehydroacetic acid, sorbic acid and the like can be mentioned.

As the antioxidant, for example, sulfite, ascorbic acid, α-tocopherol and the like can be mentioned.

Moreover, the compound of the present invention and a prodrug thereof can be used in combination with drugs other than the compound of the present invention.

As the drugs that can be used in combination with the compound of the present invention (hereinafter sometimes to be abbreviated as a concomitant drug), for example, other therapeutic agents for diabetes, therapeutic agents for diabetic complications, therapeutic agents for hyperlipidemia, antihypertensive agents, antiobesity agents, diuretics, chemotherapeutic agents, immunotherapeutic agents, immunomodulators, antiinflammatory agents, antithrombotic agents, therapeutic agents for osteoporosis, antibacterial agents, antifungal agents, antiprotozoal agents, antibiotics, antitussives and expectorant drugs, sedatives, anesthetics, antiulcer agents, tranquilizers, antipsychotic agents, antitumor agents, muscle relaxants, antiepileptics, antidepressants, antiallergic agents, cardiac stimulants, antiarrhythmic agents, vasodilators, vasoconstrictors, narcotic antagonists, vitamins, vitamin derivatives, antiasthmatic agents, antidementia agents, therapeutic agents for pollakiuria or urinary incontinence, therapeutic agents for dysuria, therapeutic agents for atopic dermatitis, therapeutic agents for allergic rhinitis, vasopressors, endotoxin antagonists or antibodies, signal transduction inhibitors, inflammatory mediator action suppressants, inflammatory mediator action suppressing antibodies, anti-inflammatory mediator action suppressants, anti-inflammatory mediator action suppressing antibodies and the like can be mentioned. Specifically, the following agents can be mentioned.

As other therapeutic agents for diabetes, insulin preparations (e.g., animal insulin preparations extracted from pancreas of bovine and swine; human insulin preparations genetically synthesized using *Escherichia coli*, yeast; zinc insulin; protamine zinc insulin; fragment or derivative of insulin (e.g., INS-1 etc.), oral insulin preparation and the like), insulin sensitizers (e.g., pioglitazone or a salt thereof (preferably hydrochloride), rosiglitazone or a salt thereof (preferably maleate), Reglixane (JTT-501), Netoglitazone (MCC-555), GI-262570, KRP-297, FK-614, Rivoglitazone (CS-011), (γE)-γ-[[[4-[(5-methyl-2-phenyl-4-oxazolyl) methoxy]phenyl]methoxy]imino]benzenebutanoic acid and the like, compounds described in WO99/58510 (e.g., (E)-4-[4-(5-methyl-2-phenyl-4-oxazolylmethoxy)benzyloxyimino]-4-phenylbutyric acid), compounds described in WO01/38325, Tesaglitazar (AZ-242), Ragaglitazar (NN-622), Muraglitazar (BMS-298585), ONO-5816, BM-13-1258, LM-4156, MBX-102, LY-519818, MX-6054, LY-510929, Balaglitazone (NN-2344), T-131 or a salt thereof, THR-0921), α-glucosidase inhibitors (e.g., voglibose, acarbose, miglitol, emiglitate etc.), biguanides (e.g., phenformin, metformin, buformin etc.), insulin secretagogues [sulfonylurea (e.g., tolbutamide, glibenclamide, gliclazide, chlorpropamide, tolazamide, acetohexamide, glyclopyramide, glimepiride etc.), repaglinide, senaglinide, mitiglinide or calcium salt hydrate thereof, nateglinide etc.], GLP-1 receptor agonists [e.g., GLP-1, GLP-1MR agent, NN-2211, AC-2993 (exendin-4), BIM-51077, Aib(8,35) hGLP-1(7,37)NH$_2$, CJC-1131 etc.], dipeptidyl peptidase IV inhibitors (e.g., NVP-DPP-278, PT-100, P32/98, P93/01, NVP-DPP-728, LAF237, TS-021 etc.), β3 agonists (e.g., CL-316243, SR-58611-A, UL-TG-307, AJ-9677, AZ40140 etc.), amylin agonists (e.g., pramlintide etc.), phosphotyrosine phosphatase inhibitors (e.g., vanadic acid etc.), gluconeogenesis inhibitors (e.g., glycogen phosphorylase inhibitors, glucose-6-phosphatase inhibitors, glucagon antagonists etc.), SGLT (sodium-glucose cotransporter) inhibitors (e.g., T-1095 etc.), 11β-hydroxysteroid dehydrogenase inhibitors (e.g., BVT-3498 etc.), adiponectin or agonists thereof, IKK inhibitors (e.g., AS-2868 etc.), leptin resistance improving drugs, somatostatin receptor agonists (compounds described in WO01/25228, WO03/42204, compounds described in WO98/44921, WO98/45285, WO99/22735 etc.), glucokinase activators (e.g., Ro-28-1675) and the like can be mentioned.

Examples of the therapeutic agents for diabetic complications include aldose reductase inhibitors (e.g., Tolrestat, Epalrestat, Zenarestat, Zopolrestat, Fidarestat (SNK-860), Minalrestat (ARI-509), CT-112 etc.), neurotrophic factors and increasing drugs thereof (e.g., NGF, NT-3, BDNF, neurotrophin production-secretion promoters described in WO01/14372 (e.g., 4-(4-chlorophenyl)-2-(2-methyl-1-imidazolyl)-5-[3-(2-methylphenoxy)propyl]oxazole etc.) and the like), protein kinase C (PKC) inhibitors (e.g., LY-333531 etc.), AGE inhibitors (e.g., ALT-945, pimagedine, pyratoxanthine, N-phenacylthiazolium bromide (ALT-766), EXO-226, ALT-711, Pyridorin, Pyridoxamine etc.), active oxygen scavengers (e.g., thioctic acid etc.), cerebral vasodilators (e.g., tiapuride etc.), somatostatin receptor agonist (BIM23190), apoptosis signal regulating kinase-1 (ASK-1) inhibitors and the like.

Examples of the therapeutic agents for hyperlipidemia include statin compounds which are cholesterol synthesis inhibitors (e.g., pravastatin, simvastatin, lovastatin, atorvastatin, fluvastatin, cerivastatin or a salt thereof (e.g., sodium salt etc.) etc.), squalene synthase inhibitors (e.g., compounds described in WO97/10224, such as N-[[(3R,5S)-1-(3-acetoxy-2,2-dimethylpropyl)-7-chloro-5-(2,3-dimethoxyphenyl)-2-oxo-1,2,3,5-tetrahydro-4,1-benzoxazepin-3-yl] acetyl]piperidine-4-acetic acid and the like), fibrate compounds (e.g., bezafibrate, clofibrate, simfibrate, clinofibrate etc.), antioxidants (e.g., lipoic acid, probucol) and the like.

Examples of the antihypertensive agents include angiotensin converting enzyme inhibitors (e.g., captopril, enalapril, delapril etc.), angiotensin II antagonists (e.g., losartan, candesartan cilexetil, eprosartan, valsartan, telmisartan, irbesartan, tasosartan, 1-[[2'-(2,5-dihydro-5-oxo-4H-1,2,4-oxadiazol-3-yl)biphenyl-4-yl]methyl]-2-ethoxy-1H-benzimidazole-7-carboxylic acid etc.), calcium antagonists (e.g., manidipine, nifedipine, amlodipine, efonidipine, nicardipine etc.), clonidine and the like.

Examples of the antiobesity agents include antiobesity agents acting on the central nervous system (e.g., dexfenfluramine, fenfluramine, phentermine, sibutramine, amfepramone, dexamphetamine, mazindol, phenylpropanolamine, clobenzorex; MCH receptor antagonists (e.g., SB-568849; SNAP-7941; compounds encompassed in WO01/82925 and WO01/87834 etc.); neuropeptide Y antagonists (e.g., CP-422935 etc.); cannabinoid receptor antagonists (e.g., SR-141716, SR-147778 etc.); ghrelin antagonists; 11β-hydroxysteroid dehydrogenase inhibitors (e.g., BVT-3498 etc.) and the like), pancreatic lipase inhibitors (e.g., orlistat, ATL-962 etc.), β3 agonists (e.g., CL-316243, SR-58611-A, UL-TG-307, AJ-9677, AZ40140 etc.), peptide anorexiants (e.g., leptin, CNTF (Ciliary Neurotropic Factor) etc.), cholecystokinin agonists (e.g., lintitript, FPL-15849 etc.), feeding deterrent (e.g., P-57 etc.) and the like.

Examples of the diuretics include xanthine derivatives (e.g., sodium salicylate and theobromine, calcium salicylate and theobromine etc.), thiazide preparations (e.g., ethiazide, cyclopenthiazide, trichloromethiazide, hydrochlorothiazide, hydroflumethiazide, benzylhydrochlorothiazide, penflutizide, polythiazide, methyclothiazide etc.), antialdosterone preparations (e.g., spironolactone, triamterene etc.), carbonate dehydratase inhibitors (e.g., acetazolamide and the like), chlorobenzenesulfonamide preparations (e.g., chlortalidone, mefruside, indapamide etc.), azosemide, isosorbide, etacrynic acid, piretanide, bumetanide, furosemide and the like.

Examples of the chemotherapeutic agents include alkylating agents (e.g., cyclophosphamide, ifosfamide etc.), metabolic antagonists (e.g., methotrexate, 5-fluorouracil etc.), antitumor antibiotics (e.g., mitomycin, adriamycin etc.), plant-derived antitumor agent (e.g., vincristine, vindesine, Taxol etc.), cisplatin, carboplatin, etoposide and the like. Of these, Furtulon or NeoFurtulon, which are 5-fluorouracil derivatives, and the like are preferable.

Examples of the immunotherapeutic agents include microorganism or bacterial components (e.g., muramyl dipeptide derivative, Picibanil etc.), polysaccharides having immunity potentiating activity (e.g., lentinan, schizophyllan, krestin etc.), cytokines obtained by genetic engineering techniques (e.g., interferon, interleukin (IL) etc.), colony stimulating factors (e.g., granulocyte colony stimulating factor, erythropoietin etc.) and the like, with preference given to interleukins such as IL-1, IL-2, IL-12 and the like.

Examples of the antiinflammatory agents include non-steroidal antiinflammatory agents such as aspirin, acetoaminofen, indomethacin and the like.

Examples of the antithrombotic agents include heparin (e.g., heparin sodium, heparin calcium, dalteparin sodium etc.), warfarin (e.g., warfarin potassium etc.), anti-thrombin drugs (e.g., aragatroban etc.), thrombolytic agents (e.g., urokinase, tisokinase, alteplase, nateplase, monteplase, pamiteplase etc.), platelet aggregation inhibitors (e.g., ticlopidine hydrochloride, cilostazol, ethyl icosapentate, beraprost sodium, sarpogrelate hydrochloride etc.) and the like.

Examples of the therapeutic agents for osteoporosis include alfacalcidol, calcitriol, elcatonin, calcitonin salmon, estriol, ipriflavone, pamidronate disodium, alendronate sodium hydrate, incadronate disodium and the like.

Examples of the vitamins include vitamin $B_1$, vitamin $B_{12}$ and the like.

Examples of the antidementia agents include tacrine, donepezil, rivastigmine, galanthamine and the like.

Examples of the therapeutic agents for pollakiuria or urinary incontinence include flavoxate hydrochloride, oxybutynin hydrochloride, propiverine hydrochloride and the like.

Examples of the therapeutic agents for dysuria include acetylcholine esterase inhibitors (e.g., distigmine) and the like.

Furthermore, drugs having a cachexia-improving action established in animal models and clinical situations, such as cyclooxygenase inhibitors (e.g., indomethacin etc.) [Cancer Research, Vol. 49, pages 5935-5939, 1989], progesterone derivatives (e.g., megestrol acetate) [Journal of Clinical Oncology, Vol. 12, pages 213-225, 1994], glucosteroids (e.g., dexamethasone etc.), metoclopramide agents, tetrahydrocannabinol agents (publications are all as mentioned above), fat metabolism improving agents (e.g., eicosapentanoic acid etc.) [British Journal of Cancer, Vol. 68, pages 314-318, 1993], growth hormones, IGF-1, or antibodies to a cachexia-inducing factor such as TNF-α, LIF, IL-6, oncostatin M and the like, can be used in combination with the preparation of the present invention.

Furthermore, glycosylation inhibitors (e.g., ALT-711, etc.), nerve regeneration promoting drugs (e.g., Y-128, VX853, prosaptide, etc.), antidepressants (e.g., desipramine, amitriptyline, imipramine, etc.), antiepileptics (e.g., lamotrigine), antiarrhythmic agents (e.g., mexiletine), acetylcholine receptor ligands (e.g., ABT-594), endothelin receptor antagonists (e.g., ABT-627), monoamine uptake inhibitors (e.g., tramadol), narcotic analgesics (e.g., orphine), GABA receptor agonists (e.g., gabapentin), $a_2$ receptor agonists (e.g., clonidine), local analgesics (e.g., apsaicin), antianxiety drugs (e.g., benzothiazepines), hosphodiesterase inhibitors (e.g., sildenafil), dopamine receptor agonists (e.g., apomorphine) and the like can be also used in combination with the compound of the present invention.

By combining the compound of the present invention with a concomitant drug, superior effects such as (1) decreased dose of the compound of the present invention or a concomitant drug as compared to single administration of the compound of the present invention or a concomitant drug, (2) possible free choice of the drug to be combined with the compound of the present invention according to the conditions of patients (mild condition, severe condition and the like), (3) possible setting of a long treatment period by selecting a concomitant drug having different action and mechanism from those of the compound of the present invention, (4) possible designing of a sustained treatment effect by selecting a concomitant drug having different action and mechanism from those of the compound of the present invention, (5) a synergistic effect afforded by a combined use of the compound of the present invention and a concomitant drug, and the like can be achieved.

When the compound of the present invention and a concomitant drug are used in combination, the administration time of the compound of the present invention and the concomitant drug is not restricted, and the compound of the present invention and the concomitant drug can be administered to an administration subject simultaneously, or may be administered at staggered times. The dosage of the concomitant drug may be determined according to the dose clinically used, and can be appropriately selected depending on an administration subject, administration route, disease, combination and the like.

As the administration mode of the compound of the present invention and the concomitant drug, the following methods can be mentioned: (1) The compound of the present invention and the concomitant drug are simultaneously formulated to give a single preparation which is administered. (2) The compound of the present invention and the concomitant drug are separately formulated to give two kinds of preparations which are administered simultaneously by the same administration route. (3) The compound of the present invention and the concomitant drug are separately formulated to give two kinds of preparations which are administered by the same administration route at staggered times. (4) The compound of the present invention and the concomitant drug are separately formulated to give two kinds of preparations which are administered simultaneously by the different administration routes. (5) The compound of the present invention and the concomitant drug are separately formulated to give two kinds of preparations which are administered by the different administration routes at staggered times (for example, the compound of the present invention and the concomitant drug are administered in this order, or in the reverse order), and the like.

The present invention is further explained in detail by referring to the following Reference Examples, Examples, Formulation Examples and Experimental Example, which are mere working examples not to be construed as limitative and may be changed without departing from the scope of the present invention.

The term "room temperature" in the following Reference Examples and Examples indicates the range of generally from about 10° C. to about 35° C. As for "%", the yield is in mol/mol %, the solvent used for chromatography is in % by volume and other "%" is in % by weight. OH proton, NH proton etc. that could not be confirmed due to broad peak by proton NMR spectrum are not included in the data.

The other symbols used herein mean the following:
s: singlet
d: doublet
t: triplet
q: quartet
m: multiplet
br: broad
J: coupling constant
Hz: Hertz
$CDCl_3$: deuterated chloroform
DMSO-$d_6$: deuterated dimethyl sulfoxide
$^1$H NMR: proton nuclear magnetic resonance In the following Reference Examples and Examples, melting point, mass spectrum (MS) and nuclear magnetic resonance spectrum (NMR) were measured under the following conditions. melting point measurement tools: Yanagimoto micromelting point measuring apparatus, or Büchi melting point measuring apparatus type B-545 was used.

MS measurement tools: Waters Corporation ZMD, Waters Corporation ZQ2000 or Micromass Ltd., platform II, ionization method:

Electron Spray Ionization (ESI) or Atmospheric Pressure Chemical Ionization (APCI). Unless specifically indicated, ESI was used.

NMR measurement tools: Varian Inc. Varian Gemini 200 (200 MHz), Varian Gemini 300 (300 MHz), Bruker BioSpin Corp. AVANCE 300.

In Reference Examples and Examples, purification by preparative HPLC was performed under the following conditions. Preparative HPLC tools: Gilson, Inc., high through-put purification system column: YMC Combiprep ODS-A S-5 μm, 20×50 mm solvent:
  Solution A; 0.1% trifluoroacetic acid-containing water,
  Solution B; 0.1% trifluoroacetic acid-containing acetonitrile gradient cycle A: 0.00 min (Solution A/Solution B=90/10), 1.20 min (Solution A/Solution B=90/10), 4.75 min (Solution A/Solution B=0/100), 7.30 min (Solution A/Solution B=0/100), 7.40 min (Solution A/Solution B=90/10), 7.50 min (Solution A/Solution B=90/10).

gradient cycle B: 0.00 min (Solution A/Solution B=95/5), 1.00 min (Solution A/Solution B=95/5), 5.20 min (Solution A/Solution B=5/95), 6.40 min (Solution A/Solution B=5/95), 6.50 min (Solution A/Solution B=95/5), 6.60 min (Solution A/Solution B=95/5).

flow rate: 25 ml/min, detection method: UV 220 nm

REFERENCE EXAMPLE 1 ethyl 4-[5-benzyloxy)-2-formylphenoxy]butyrate

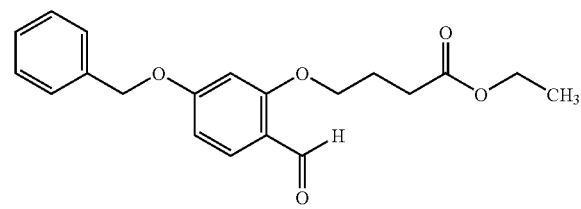

4-(Benzyloxy)-2-hydroxybenzaldehyde (5.8 g), ethyl 4-bromobutyrate (7.1 mL), potassium carbonate (10.5 g) and sodium iodide (3.8 g) were added to N,N-dimethylformamide (50 mL), and the mixture was stirred overnight at room temperature. The mixture was poured into water and extracted with ethyl acetate. The organic layer was washed with water and brine and dried over magnesium sulfate, and the solvent was evaporated. The residue was purified by silica gel column chromatography (ethyl acetate:hexane) to give the title compound (8.2 g) as an oil.

$^1$H NMR (CDCl$_3$) δ: 1.26(3H, t), 2.14-2.23(2H, m), 2.53 (2H, t), 4.06-4.20(4H, m), 5.12(2H, s), 6.53(1H, d), 6.62(1H, dd), 7.34-7.45(5H, m), 7.81(1H, d).

REFERENCE EXAMPLE 2 ethyl 8-(benzyloxy)-2,3-dihydro-1-benzoxepine-4-carboxylate

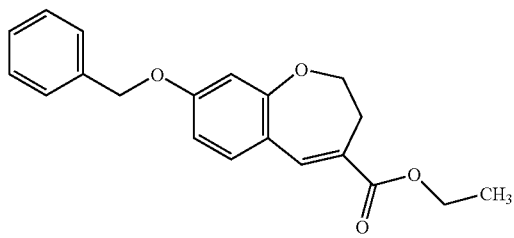

Ethyl 4-[5-(benzyloxy)-2-formylphenoxy]butyrate (8.2 g) was dissolved in diethyl carbonate (100 mL), and potassium t-butoxide (4 g) was added, and the mixture was stirred overnight at room temperature. 1 M hydrochloric acid was added, and the mixture was concentrated and extracted with ethyl acetate. The organic layer was washed with water and brine and dried over magnesium sulfate. The solvent was evaporated to give the title compound (5.2 g) as crude crystals. A part thereof was recrystallized from ethyl acetate-hexane to give crystals.

melting point: 75-76° C.

REFERENCE EXAMPLE 3 ethyl 8-hydroxy-2,3-dihydro-1-benzoxepine-4-carboxylate

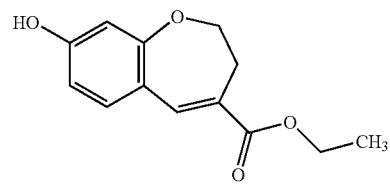

Ethyl 8-(benzyloxy)-2,3-dihydro-1-benzoxepine-4-carboxylate (2.5 g) was dissolved in trifluoroacetic acid (10 mL), and 42% hydrobromic acid (0.5 mL) was added, and the mixture was heated at 60° C. for 30 min. The mixture was concentrated and extracted with ethyl acetate. The organic layer was washed with water and back-extracted with 1 M aqueous sodium hydroxide solution. The aqueous layer was acidified with hydrochloric acid and extracted with ethyl acetate. The organic layer was washed with water and brine, and dried over magnesium sulfate, and the solvent was evaporated. The residue was dissolved in ethanol (100 mL), and thionyl chloride (1 mL) was added dropwise under ice-cooling. The mixture was stirred overnight at room temperature, and the solvent was evaporated. The residue was purified by silica gel column chromatography (ethyl acetate:hexane) to give crude crystals. The crystals were recrystallized from ethyl acetate-hexane to give the title compound (0.39 g) as crystals.

melting point: 131-132° C.

REFERENCE EXAMPLE 4 ethyl 8-hydroxy-2,3,4,5-tetrahydro-1-benzoxepine-4-carboxylate

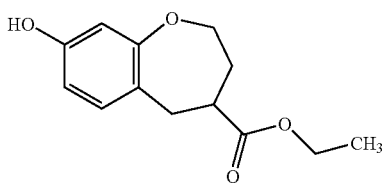

Ethyl 8-(benzyloxy)-2,3-dihydro-1-benzoxepine-4-carboxylate (3.5 g) was dissolved in ethanol (50 mL), and the solution was subjected to catalytic reduction using 10% palladium on carbon (0.35 g) for 3 days. The catalyst was filtered off, and the solvent of the filtrate was evaporated. The residue was purified by silica gel column chromatography (ethyl acetate:hexane) to give the title compound (2.7 g) as an oil.

$^1$H NMR (CDCl$_3$) δ: 1.25(3H, t), 2.12-2.25(2H, m), 2.52-2.68(1H, m), 2.89-3.11(2H, m), 3.76-3.88(1H, m), 4.14(2H, q), 4.23-4.34(1H, m), 4.78(1H, s), 6.44-6.50(2H, m), 7.00 (1H, d).

REFERENCE EXAMPLE 5

2',6'-dimethylbiphenyl-3-carbaldehyde

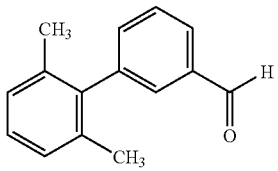

3-Bromobenzaldehyde (18.5 g, 100 mmol) and (2,6-dimethylphenyl)boronic acid (21.0 g, 140 mmol) were dissolved in a mixed solvent of 1 M aqueous sodium carbonate solution (200 mL), ethanol (100 mL) and toluene (200 mL). After argon substitution, tetrakis(triphenylphosphine)palladium(0) (5.78 g, 5.00 mmol) was added. The reaction mixture was stirred under an argon atmosphere at 80° C. for 20 hr. The reaction mixture was cooled, and water was added to the reaction mixture. The mixture was diluted with ethyl acetate, and the insoluble material was filtered through celite. The organic layer of the filtrate was washed with saturated brine, dried over anhydrous magnesium sulfate and concentrated under reduced pressure. The residue was purified by silica gel column chromatography (hexane-10% ethyl acetate/hexane) to give the title compound (20.4 g, yield 97%) as a colorless oil.

MS m/z 211 (MH$^+$)

REFERENCE EXAMPLE 6

(2',6'-dimethylbiphenyl-3-yl)methanol

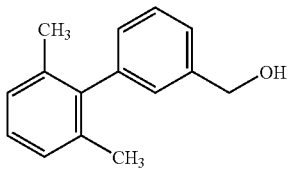

2',6'-Dimethylbiphenyl-3-carbaldehyde (18.5 g, 88.0 mmol) was dissolved in a mixed solvent of 1,2-dimethoxyethane (100 mL) and tetrahydrofuran (100 mL), and sodium borohydride (1.66 g, 44.0 mmol) was added under ice-cooling, and the mixture was stirred at the same temperature for 3 hr, further at room temperature for 3 hr. Diluted hydrochloric acid was added to the reaction mixture, and the mixture was extracted with ethyl acetate. The extract was washed with saturated brine, dried over anhydrous magnesium sulfate and concentrated under reduced pressure. The residue was purified by silica gel column chromatography (10%-50% ethyl acetate/hexane) to give the title compound (15.6 g, yield 83%) as a colorless oil.

$^1$H NMR (CDCl$_3$) δ: 1.66(1H, t, J=5.9 Hz), 2.03(6H, s), 4.74(2H, d, J=5.9 Hz), 7.07-7.19(5H, m), 7.35(1H, d, J=7.5 Hz), 7.43(1H, t, J=7.5 Hz).

REFERENCE EXAMPLE 7 ethyl (6-hydroxy-1,2,3,4-tetrahydronaphthalen-1-yl)acetate

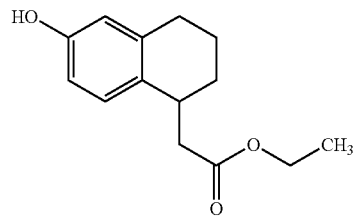

A mixture (3.34 g, 14.4 mmol) of ethyl (6-hydroxy-3,4-dihydronaphthalen-1-yl)acetate and ethyl (2E)-(6-hydroxy-3,4-dihydronaphthalen-1(2H)-ylidene)acetate, which was obtained during the process of Example 1, was dissolved in ethanol (70 mL), and 10% palladium on carbon (50% water wet, 0.2 g) was added, and the mixture was stirred under hydrogen atmosphere (balloon pressure) at room temperature for 18 hr. The catalyst was filtered off, and the filtrate was concentrated under reduced pressure. The residue was purified by silica gel column chromatography (5%-30% ethyl acetate/hexane) to give the title compound (1.95 g, yield 58%) as a pale-yellow oil.

MS m/z 235 (MH$^+$)

REFERENCE EXAMPLE 8

5-benzyloxy-1-indanone

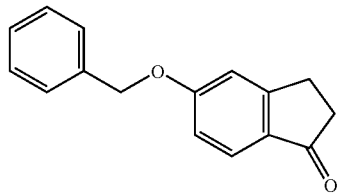

[Step 1]

A suspension of 5-methoxy-1-indanone (10.3 g, 63.5 mmol) in toluene (150 mL) was ice-cooled, and aluminum chloride (16.9 g, 127 mmol) was added by small portions, and the mixture was heated under reflux under nitrogen atmosphere for 4 hr. The reaction mixture was allowed to cool to room temperature and poured into iced water. The organic product was extracted with a mixed solvent of ethyl acetate and tetrahydrofuran. The extract was dried over anhydrous magnesium sulfate and concentrated under reduced pressure to give 5-hydroxy-1-indanone as yellow crystals.

[Step 2]

This product was suspended in acetone (120 mL), and benzyl bromide (10.9 g, 64.0 mmol) and potassium carbonate (12.3 g, 88.9 mmol) were added, and the mixture was heated under reflux under nitrogen atmosphere for 1 hr. The reaction mixture was allowed to cool to room temperature, and ethyl acetate and water were added. The organic layer was washed with saturated brine, dried over anhydrous magnesium sulfate and concentrated under reduced pressure to give the title compound (14.2 g, 94%) as pale-yellow crystals (recrystallized from ethyl acetate).

MS m/z 239 (MH$^+$).

REFERENCE EXAMPLE 9 ethyl (2E)-[5-(benzyloxy)-2,3-dihydro-1H-inden-1-ylidene]acetate

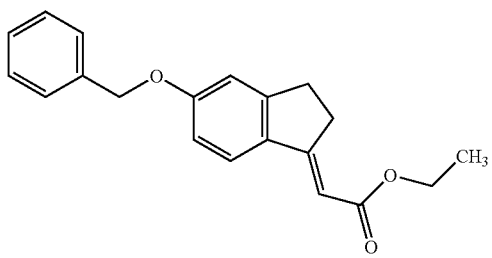

To an ice-cooled solution of triethyl phosphonoacetate (4.75 g, 21.2 mmol) in toluene (15 mL) was added by small portions sodium hydride (60% in oil, 0.848 g, 21.2 mmol), and the mixture was heated to 50° C. under nitrogen atmosphere and was stirred for 1 hr. The reaction mixture was ice-cooled, and a solution of 5-benzyloxy-1-indanone (3.36 g, 14.1 mmol) in toluene (15 mL) was added dropwise. The mixture was heated under reflux for 4 hr and cooled to room temperature. 1 M Hydrochloric acid was added, and the mixture was extracted with ethyl acetate. The extract was dried over anhydrous magnesium sulfate and concentrated under reduced pressure. The residue was purified by silica gel column chromatography (5%-30% ethyl acetate/hexane), and the obtained solid was recrystallized from ethyl acetate-hexane to give the title compound (2.11 g, yield 49%) as pale-yellow prism crystals.

MS m/z 309 (MH$^+$).

REFERENCE EXAMPLE 10 ethyl (5-hydroxy-2,3-dihydro-1H-inden-1-yl)acetate

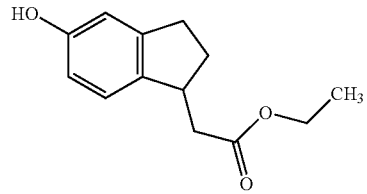

To a solution of ethyl (2E)-[5-(benzyloxy)-2,3-dihydro-1H-inden-1-ylidene]acetate (2.10 g, 6.81 mmol) in ethanol (20 mL) was added 10% palladium on carbon (50% water wet, 0.5 g), and the mixture was stirred under hydrogen atmosphere (balloon pressure) at room temperature for 24 hr. The catalyst was filtered off, and the filtrate was concentrated under reduced pressure. The residue was purified by silica gel column chromatography (5%-30% ethyl acetate/hexane) to give the title compound (1.45 g, yield 97%) as a colorless oil.

$^1$H NMR (CDCl$_3$) δ: 1.28(3H, t, J=7.1 Hz), 1.69-1.81(1H, m), 2.32-2.44(2H, m), 2.71(1H, dd, J=15.3, 5.8 Hz), 2.77-2.94(2H, m), 3.46-3.56(1H, m), 4.18(2H, q, J=7.1 Hz), 4.71 (1H, s), 6.62(1H, dd, J=8.1, 2.2 Hz), 6.70(1H, d, J=2.2 Hz), 7.02(1H, d, J=8.1 Hz).

REFERENCE EXAMPLE 11 methyl 4-{[(4-phenyl-1,3-thiazol-2-yl)(propyl)amino]methyl}benzoate

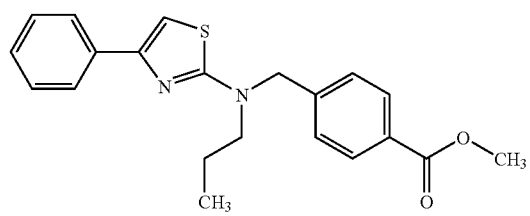

In the same manner as in Reference Example 38, the title compound was obtained as a colorless oil from 4-phenyl-N-propyl-1,3-thiazol-2-amine and methyl 4-(bromomethyl) benzoate. yield 75%.

$^1$H NMR (CDCl$_3$) δ: 0.93(3H, t, J=7.7 Hz), 1.64-1.74(2H, m), 3.40(2H, t, J=7.7 Hz), 3.91(3H, s), 4.85(2H, s), 6.72(1H, s), 7.23-7.42(5H, m), 7.82-7.85(2H, m), 7.99-8.01(2H, m).

REFERENCE EXAMPLE 12

(4-{[(4-phenyl-1,3-thiazol-2-yl)(propyl)amino]methyl}phenyl)methanol

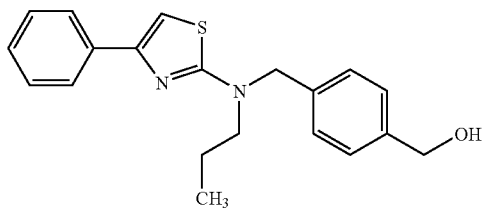

In the same manner as in Reference Example 41, the title compound was obtained as a colorless oil from methyl 4-{[(4-phenyl-1,3-thiazol-2-yl)(propyl)amino]methyl}benzoate. yield 67%.

$^1$H NMR (CDCl$_3$) δ: 0.93(3H, t, J=7.4 Hz), 1.62(1H, t, J=5.8 Hz), 1.64-1.74(2H, m), 3.40(2H, t, J=7.7 Hz), 4.69(2H, d, J=5.8 Hz), 4.79(2H, s), 6.70(1H, s), 7.24-7.39(7H, m), 7.84-7.87(2H, m).

REFERENCE EXAMPLE 13 ethyl (2E,4E)-5-(3-methoxyphenyl)penta-2,4-dienoate

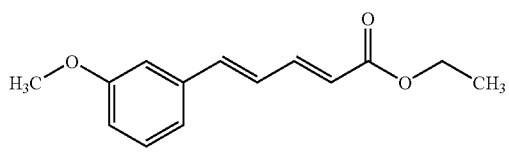

To an ice-cooled solution of triethyl 4-phosphonocrotonate (24.0 g, 95.9 mmol) in tetrahydrofuran (100 mL) was added by small portions sodium hydride (60% in oil, 3.84 g, 96.0 mmol), and the mixture was stirred under nitrogen atmosphere for 30 min. A solution of 3-methoxybenzaldehyde (12.3 g, 90.0 mmol) in tetrahydrofuran (100 mL) was added dropwise to the reaction mixture and the mixture was stirred at room temperature for 2 hr. N,N-Dimethylformamide (50 mL) was added and the mixture was further stirred for 18 hr. The reaction mixture was concentrated under reduced pressure, and 1 M hydrochloric acid was added, and the mixture was extracted with ethyl acetate. The extract was dried over anhydrous magnesium sulfate and concentrated under reduced pressure. The residue was purified by silica gel column chromatography (10%-30% ethyl acetate/hexane) to give the title compound (7.70 g, yield 37%) as a yellow oil.

MS m/z 233 (MH$^+$)

REFERENCE EXAMPLE 14 ethyl 5-(3-methoxyphenyl)pentanoate

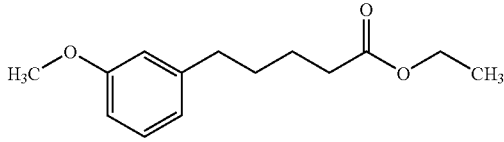

In the same manner as in Reference Example 10, the title compound was obtained as a colorless oil from ethyl (2E,4E)-5-(3-methoxyphenyl)penta-2,4-dienoate. yield 77%.

$^1$H NMR (CDCl$_3$) δ: 1.25(3H, t, J=7.2 Hz), 1.60-1.72(4H, m), 2.32(2H, t, J=7.0 Hz), 2.61(2H, t, J=7.0 Hz), 3.80(3H, s), 4.12(2H, q, J=7.2 Hz), 6.72-6.78(3H, m), 7.16-7.22(1H, m).

REFERENCE EXAMPLE 15

5-(3-methoxyphenyl)pentanoic acid

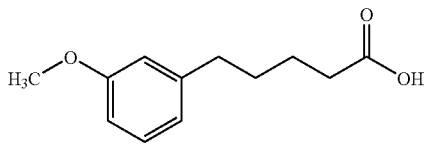

To a solution of ethyl 5-(3-methoxyphenyl)pentanoate (6.01 g, 25.4 mmol) in a mixed solvent of ethanol (50 mL) and tetrahydrofuran (50 mL) was added 2 M aqueous sodium hydroxide solution (25 mL), and the mixture was stirred at room temperature for 3 hr. Water was added to the reaction mixture, and the mixture was acidified with 1 M hydrochloric acid and extracted with ethyl acetate. The extract was washed with saturated brine, dried over anhydrous magnesium sulfate and concentrated under reduced pressure to give the title compound (5.28 g, yield 99%) as a red-brown oil.

$^1$H NMR (CDCl$_3$) δ: 1.66-1.70(4H, m), 2.36-2.41(2H, m), 2.59-2.64(2H, m), 3.80(3H, s), 6.72-6.78(3H, m), 7.17-7.22 (1H, m).

REFERENCE EXAMPLE 16

2-methoxy-6,7,8,9-tetrahydro-5H-benzo[7]annulen-5-one

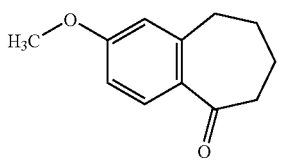

A mixture of phosphorus(V) oxide (10 g) and methanesulfonic acid (70 mL) was stirred at 100° C. for 1 hr. The obtained solution and 5-(3-methoxyphenyl)pentanoic acid (5.28 g, 25.4 mmol) were mixed and the mixture was stirred for 1 hr. The reaction mixture was poured into iced water and extracted with ethyl acetate. The extract was washed with saturated brine, dried over anhydrous magnesium sulfate and concentrated under reduced pressure. The residue was purified by silica gel column chromatography (hexane-30% ethyl acetate/hexane) to give the title compound (4.02 g, 83%) as a red-brown oil.

MS m/z 191 (MH$^+$).

REFERENCE EXAMPLE 17

2-(benzyloxy)-6,7,8,9-tetrahydro-5H-benzo[7]annulen-5-one

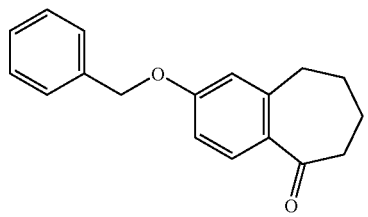

In the same manner as in Reference Example 8, the title compound was obtained as a colorless prism crystals from 2-methoxy-6,7,8,9-tetrahydro-5H-benzo[7]annulen-5-one. yield 91% (recrystallized from ethyl acetate-hexane).

MS m/z 267 (MH$^+$).

REFERENCE EXAMPLE 18 ethyl (2-hydroxy-6,7,8,9-tetrahydro-5H-benzo[7]annulen-5-yl)acetate

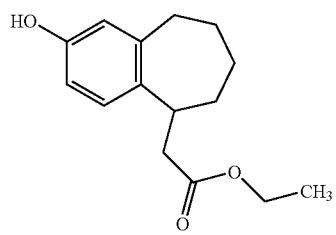

In the same manner as in Reference Examples 9 and 10, the title compound was obtained as a colorless oil from 2-(benzyloxy)-6,7,8,9-tetrahydro-5H-benzo[7]annulen-5-one. yield 89%.

MS m/z 249 (MH$^+$).

REFERENCE EXAMPLE 19

4-(chloromethyl)-7-hydroxy-2H-chromen-2-one

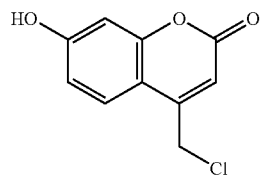

Ethyl 4-chloroacetoacetate (14.0 g, 85.0 mmol) was dissolved in conc. sulfuric acid (30 mL) under ice-cooling and resorcinol (8.81 g, 80.0 mmol) was added by small portions, and the mixture was stirred at room temperature for 2 hr. The reaction mixture was poured into iced water. The resulting solid was collected by filtration, washed with water and air dried to give the title compound (14.1 g, 84%).

MS m/z 211 (MH$^+$).

REFERENCE EXAMPLE 20 methyl (6-hydroxy-1-benzofuran-3-yl)acetate

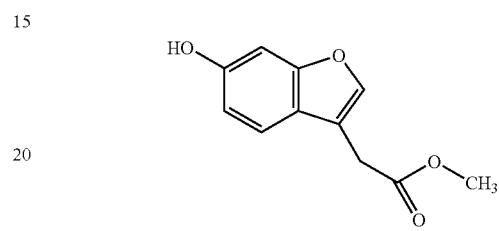

[Step 1]

A mixture of 4-(chloromethyl)-7-hydroxy-2H-chromen-2-one (10.9 g, 51.8 mmol) and 1 M aqueous sodium hydroxide solution (500 mL) was heated under reflux for 2 hr. The reaction mixture was allowed to cool, acidified with conc. sulfuric acid and extracted with ethyl acetate. The extract was washed with saturated brine, dried over anhydrous magnesium sulfate and concentrated under reduced pressure to give (6-hydroxy-1-benzofuran-3-yl)acetic acid (8.27 g, 83%) as brown crystals.

[Step 2]

This product (9.85 g, 51.3 mmol) was suspended in methanol (45 mL), and conc. sulfuric acid (5 mL) was added, and the mixture was heated under reflux for 4 hr. The reaction mixture was concentrated under reduced pressure, and water was added, and the mixture was extracted with diethyl ether. The extract was washed with saturated aqueous sodium hydrogen carbonate and saturated brine, dried over anhydrous magnesium sulfate and concentrated under reduced pressure. The residue was purified by silica gel column chromatography (10%-50% ethyl acetate/hexane), and the obtained solid was recrystallized from ethyl acetate-hexane to give the title compound (7.38 g, yield 70%) as pale-yellow prism crystals.

MS m/z 207 (MH$^+$).

REFERENCE EXAMPLE 21 methyl (6-hydroxy-2,3-dihydro-1-benzofuran-3-yl)acetate

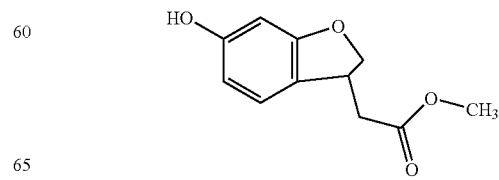

To a solution of methyl (6-hydroxy-1-benzofuran-3-yl)acetate (11.4 g, 55.3 mmol) in methanol (100 mL) was added 10% palladium on carbon (50% water wet, 2 g), and the mixture was stirred under hydrogen atmosphere (balloon pressure) at room temperature for 18 hr. The catalyst was filtered off, and the filtrate was concentrated under reduced pressure. The residue was purified by silica gel column chromatography (20%-50% ethyl acetate/hexane), and the obtained solid was recrystallized from ethyl acetate-hexane to give the title compound (8.74 g, yield 76%) as colorless prism crystals.

MS m/z 209 (MH$^+$).

REFERENCE EXAMPLE 22 ethyl 2',4'-dimethylbiphenyl-3-carboxylate

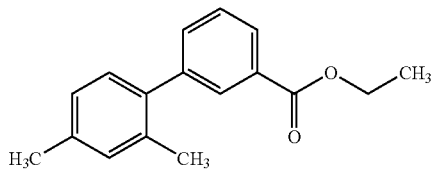

(2,4-Dimethylphenyl)boronic acid (3.0 g, 20.0 mmol), ethyl 3-bromobenzoate (4.3 g, 18.8 mmol) and cesium carbonate (9.8 g, 30.0 mmol) were added to a mixed solvent of ethanol (20 mL) and toluene (80 mL). After argon substitution, tetrakis(triphenylphosphine)palladium(0) (0.30 g, 0.26 mmol) was added, and the reaction mixture was stirred under an argon atmosphere at 70° C. for 18 hr. The reaction mixture was cooled, and the insoluble material was filtered through celite, and the filtrate was concentrated under reduced pressure. The obtained residue was subjected to silica gel column chromatography (ethyl acetate:hexane=1:10) to give the title compound (5.0 g, yield 100%) as a colorless oil.

$^1$H NMR (CDCl$_3$) δ: 1.39(3H, t, J=7.0 Hz), 2.23(3H, s), 2.37(3H, s), 4.38(2H, q, J=7.0 Hz), 7.02-7.54(5H, m), 8.00-8.05(2H, m).

REFERENCE EXAMPLE 23

(2',4'-dimethylbiphenyl-3-yl)methanol

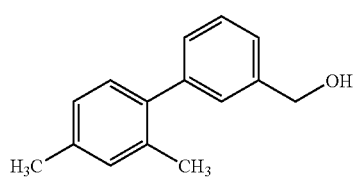

To a solution of ethyl 2',4'-dimethylbiphenyl-3-carboxylate (5.0 g, 19.7 mmol) in anhydrous tetrahydrofuran (50 mL) was added lithium aluminum hydride (0.91 g, 24.0 mmol) under ice-cooling, and the mixture was stirred at room temperature for 3 hr. The reaction solution was ice-cooled, and sodium sulfate decahydrate (8.0 g, 24.8 mmol) was added, and the mixture was stirred at room temperature for 1 hr. The precipitated insoluble material was filtered through celite, and the filtrate was concentrated under reduced pressure to give the title compound as a colorless oil. yield 96%.

$^1$H NMR (CDCl$_3$) δ: 2.24(3H, s), 2.36(3H, s), 4.73(2H, d, J=6.0 Hz), 7.00-7.45(7H, m).

REFERENCE EXAMPLE 24

2',4',6'-trimethylbiphenyl-3-carbaldehyde

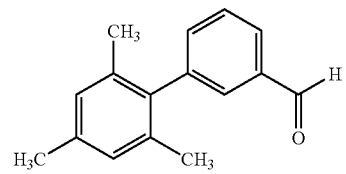

In the same manner as in Reference Example 22, the title compound was obtained as a colorless oil from 3-bromobenzaldehyde and (2,4,6-trimethylphenyl)boronic acid. yield 76%.

MS m/z 225 (MH$^+$)

REFERENCE EXAMPLE 25

(2',4',6'-trimethylbiphenyl-3-yl)methanol

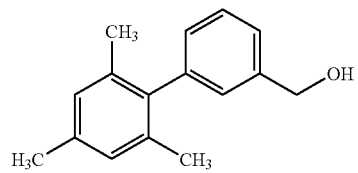

2',4',6'-Trimethylbiphenyl-3-carbaldehyde (2.36 g, 10.5 mmol) was dissolved in ethanol (20 mL), and sodium borohydride (0.40 g, 10.6 mmol) was added to this solution. After stirring under ice-cooling for 3 hr, aqueous citric acid solution was added to the reaction solution, and the mixture was extracted with ethyl acetate. The extract was washed with aqueous sodium chloride solution, dried over magnesium sulfate and concentrated under reduced pressure. The obtained residue was subjected to silica gel column chromatography (ethyl acetate:hexane=1:5-1:2) to give the title compound (1.66 g, yield 70%) as a colorless oil.

$^1$H NMR (CDCl$_3$) δ: 2.00(6H, s), 2.33(3H, s), 4.73(2H, d, J=6.2 Hz), 6.94(2H, s), 7.00-7.42(4H, m).

REFERENCE EXAMPLE 26

(2',6'-dimethyl-6-methoxybiphenyl-3-yl)methanol

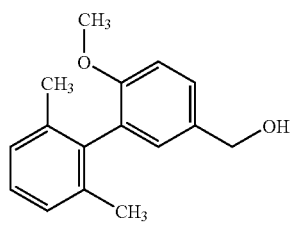

In the same manner as in Reference Examples 22 and 25, the title compound was obtained as a colorless oil from 1-bromo-2,6-dimethylbenzene and (2-methoxy-5-formylphenyl)boronic acid. yield 76%.

$^1$H NMR (CDCl$_3$) δ: 2.01(6H, s), 3.74(3H, s), 4.65(2H, d, J=5.2 Hz), 6.97(1H, d, J=8.4 Hz), 7.03(1H, d, J=2.2 Hz), 7.06-7.24(3H, m), 7.35(1H, dd, J=8.4, 2.6 Hz).

REFERENCE EXAMPLE 27

3-(1-benzothien-5-yl)benzaldehyde

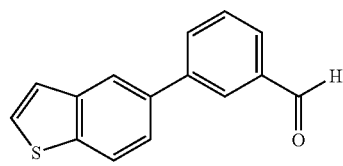

In the same manner as in Reference Example 22, the title compound was obtained as a pale-yellow oil from 5-bromo-1-benzothiophene and (3-formylphenyl)boronic acid. yield 70%.

MS m/z 239 (MH$^+$).

REFERENCE EXAMPLE 28

[3-(1-benzothien-5-yl)phenyl]methanol

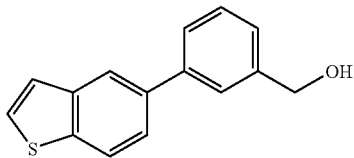

3-(1-Benzothien-5-yl)benzaldehyde (3.9 g, 16.4 mmol) was dissolved in ethanol (80 mL) and tetrahydrofuran (20 mL), and the mixture was ice-cooled. Sodium borohydride (0.62 g, 16.4 mmol) was added to this solution, and the mixture was stirred under ice-cooling for 3 hr. Aqueous citric acid solution was added to the reaction solution, and the mixture was extracted with ethyl acetate. The extract was washed with aqueous sodium chloride solution, dried over magnesium sulfate and concentrated under reduced pressure. The obtained oil was crystallized from ethyl acetate-hexane to give the title compound (3.9 g, yield 99%) as colorless prism crystals.

$^1$H NMR (CDCl$_3$) δ: 1.73(1H, t, J=6.0 Hz), 4.79(2H, d, J=6.0 Hz), 7.35-7.63(6H, m), 7.68(1H, s), 7.94(1H, d, J=8.1 Hz), 8.04(1H, d, J=1.8 Hz).

REFERENCE EXAMPLE 29

3-(1-benzothien-3-yl)benzaldehyde

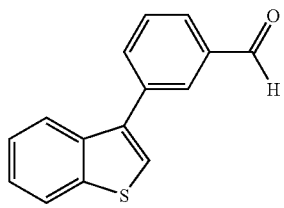

(3-Formylphenyl)boronic acid (1.7 g, 11.3 mmol), 3-bromo-1-benzothiophene (2.0 g, 9.39 mmol) and cesium carbonate (4.6 g, 14.1 mmol) were added to a mixed solvent of ethanol (10 mL) and toluene (50 mL). After argon substitution, tetrakis(triphenylphosphine)palladium(0) (0.20 g, 0.17 mmol) was added. The reaction mixture was stirred under an argon atmosphere at 70° C. for 18 hr. The reaction mixture was cooled, and the insoluble material was filtered through celite, and the filtrate was concentrated under reduced pressure. The obtained residue was subjected to silica gel column chromatography (ethyl acetate:hexane=1:10-1:5) to give the title compound (2.1 g, yield 94%) as a pale-yellow oil.

MS m/z 239 (MH$^+$)

REFERENCE EXAMPLE 30

[3-(1-benzothien-3-yl)phenyl]methanol

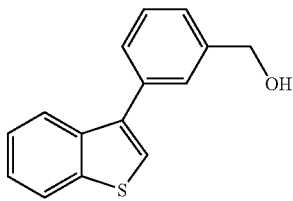

To a solution of 3-(1-benzothien-3-yl)benzaldehyde (2.1 g, 8.81 mmol) in anhydrous tetrahydrofuran (30 mL) was added lithium aluminum hydride (0.37 g, 9.75 mmol) under ice-cooling, and the mixture was stirred at room temperature for 2 hr. The reaction solution was ice-cooled, and sodium sulfate decahydrate (3.0 g, 5.74 mmol) was added, and the mixture was stirred at room temperature for 1 hr. The precipitated insoluble material was filtered through celite, and the filtrate was concentrated under reduced pressure. The obtained residue was subjected to silica gel column chromatography (ethyl acetate:hexane=1:5-1:3) to give the title compound (2.0 g, yield 95%) as a colorless oil.

$^1$H NMR (CDCl$_3$) δ: 1.72(1H, t, J=5.8 Hz), 4.80(2H, d, J=5.8 Hz), 7.35-7.64(7H, m), 7.88-7.98(2H, m).

REFERENCE EXAMPLE 31

3-(2-methyl-1-naphthyl)benzaldehyde

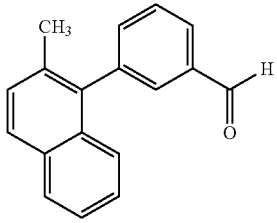

In the same manner as in Reference Example 5, the title compound was obtained as a pale-yellow oil from 1-bromo-2-methylnaphthalene and (3-formylphenyl)boronic acid. yield 65%.

MS m/z 247 (MH$^+$)

REFERENCE EXAMPLE 32

[3-(2-methyl-1-naphthyl)phenyl]methanol

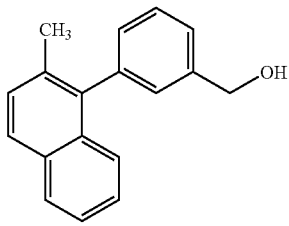

3-(2-Methyl-1-naphthyl)benzaldehyde (2.39 g, 9.70 mmol) was dissolved in a mixed solvent of 1,2-dimethoxyethane (10 mL) and tetrahydrofuran (10 mL), and sodium borohydride (0.189 g, 5.00 mmol) was added under ice-cooling, and the mixture was stirred at the same temperature for 3 hr. Diluted hydrochloric acid was added to the reaction mixture, and the mixture was extracted with ethyl acetate. The extract was washed with saturated brine, dried over anhydrous magnesium sulfate and concentrated under reduced pressure. The residue was purified by silica gel column chromatography (5%-30% ethyl acetate/hexane) to give the title compound (1.96 g, yield 81%) as a colorless viscous oil.

$^1$H NMR (CDCl$_3$) δ: 1.66(1H, t, J=5.9 Hz), 2.03(6H, s), 4.74(2H, d, J=5.9 Hz), 7.07-7.19(5H, m), 7.35(1H, d, J=7.5 Hz), 7.43(1H, t, J=7.5 Hz).

REFERENCE EXAMPLE 33

4'-hydroxy-2',6'-dimethyl-3-biphenylcarbaldehyde

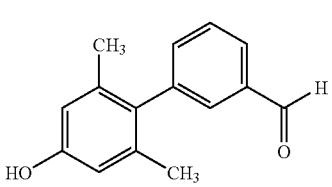

In the same manner as in Reference Example 5, the title compound was obtained as pale-yellow crystals from 4-bromo-3,5-dimethylphenol and (3-formylphenyl)boronic acid. yield 83%.

MS m/z 227 (MH$^+$).

REFERENCE EXAMPLE 34

2-(4-bromo-3-methylphenoxy)tetrahydro-2H-pyran

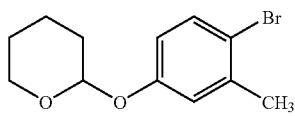

A solution of 4-bromo-3-methylphenol (4.72 g, 25.2 mmol), 3,4-dihydro-2H-pyran (3.18 g, 37.8 mmol) and pyridinium p-toluenesulfonate (0.628 g, 2.50 mmol) in dichloromethane (100 mL) was stirred at room temperature for 24 hr. The reaction mixture was washed with water and dried over anhydrous sodium sulfate. The solvent was evaporated under reduced pressure to give the title compound (7.11 g, including unreacted 3,4-dihydro-2H-pyran) as a yellow oil.

$^1$H NMR (CDCl$_3$) δ: 1.58-2.06(6H, m), 2.35(3H, s), 3.56-3.63(1H, m), 3.83-3.91(1H, m), 5.37(1H, t, J=3.1 Hz), 6.77 (1H, dd, J=8.8, 3.0 Hz), 6.95(1H, d, J=3.0 Hz), 7.39(1H, d, J=8.8 Hz).

REFERENCE EXAMPLE 35

2'-methyl-4'-(tetrahydro-2H-pyran-2-yloxy)biphenyl-3-carbaldehyde

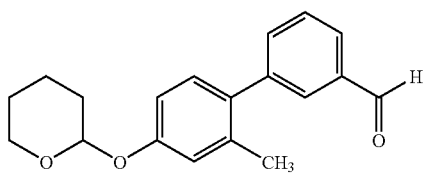

In the same manner as in Reference Example 5, the title compound was obtained as a pale-yellow oil from 2-(4-bromo-3-ethylphenoxy)tetrahydro-2H-pyran and (3-formylphenyl)boronic acid. yield 82% (2 steps).

$^1$H NMR (CDCl$_3$) δ: 1.53-1.77(3H, m), 1.86-1.91(2H, m), 1.98-2.09(1H, m), 2.25(3H, s), 3.61-3.68(1H, m), 3.91-3.99 (1H, m), 5.48(1H, t, J=3.2 Hz), 6.95-7.00(2H, m), 7.15(1H, d, J=8.3 Hz), 7.53-7.60(2H, m), 7.82-7.86(2H, m), 10.06(1H, s).

REFERENCE EXAMPLE 36

[2'-methyl-4'-(tetrahydro-2H-pyran-2-yloxy)biphenyl-3-yl]methanol

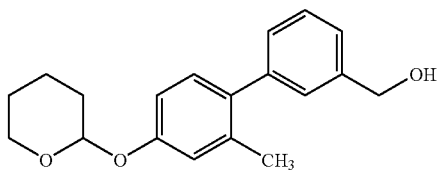

In the same manner as in Reference Example 6, the title compound was obtained as a colorless oil from 2'-methyl-4'-(tetrahydro-2H-pyran-2-yloxy)biphenyl-3-carbaldehyde. yield 89%.

$^1$H NMR (CDCl$_3$) δ: 1.59-1.76(4H, m), 1.85-1.90(2H, m), 1.97-2.11(1H, m), 2.25(3H, s), 3.60-3.67(1H, m), 3.91-3.99 (1H, m), 4.73(2H, d, J=5.8 Hz), 5.46(1H, t, J=3.1 Hz), 6.92-6.97(2H, m), 7.14(1H, d, J=8.1 Hz), 7.22-7.41(4H, m).

REFERENCE EXAMPLE 37 methyl [6-(3-chloropropoxy)-2,3-dihydro-1-benzofuran-3-yl]acetate

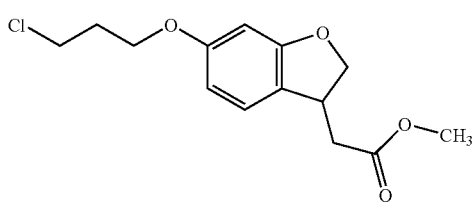

Methyl (6-hydroxy-2,3-dihydro-1-benzofuran-3-yl)acetate (2.71 g, 13.0 mmol) and 1-bromo-3-chloropropane (2.46 g, 15.6 mmol) were dissolved in N,N-dimethylformamide (15 mL), and potassium carbonate (1.98 g, 14.3 mmol) was added, and the mixture was stirred under nitrogen atmosphere at room temperature for 24 hr. The reaction mixture was concentrated under reduced pressure, and water added, and the mixture was extracted with ethyl acetate. The extract was washed with saturated brine, dried over anhydrous magnesium sulfate and concentrated under reduced pressure. The residue was purified by silica gel column chromatography (5%-30% ethyl acetate/hexane) to give the title compound (2.95 g, yield 80%) as a colorless oil.

MS m/z 285 (MH$^+$).

REFERENCE EXAMPLE 38 methyl 4-{[(2-phenylethyl)(4-phenyl-1,3-thiazol-2-yl)amino]methyl}benzoate

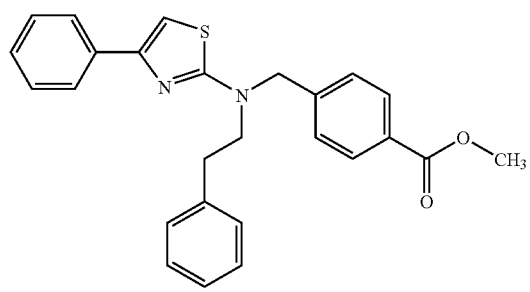

To a solution of 4-phenyl-N-(2-phenylethyl)-1,3-thiazol-2-amine (4.63 g, 16.5 mmol) in N,N-dimethylformamide (50 mL) was added sodium hydride (60% in oil, 990 mg, 24.8 mmol), and the mixture was stirred for 30 min. Methyl 4-(bromomethyl)benzoate (4.54 g, 19.8 mmol) was added and the mixture was stirred at room temperature for 2 hr. Water was added to the reaction mixture, and the mixture was extracted with ethyl acetate. The extract was washed with water and concentrated under reduced pressure. The residue was purified by silica gel column chromatography to give the title compound (3.39 g, yield 48%) as a yellow oil.

$^1$H NMR (CDCl$_3$) δ: 3.00(2H, t, J=7.8 Hz), 3.69(2H, t, J=7.8 Hz), 3.90(3H, s), 4.71(2H, s), 6.76(1H, s), 7.18-7.41 (10H, m), 7.86-7.88(2H, m), 7.98-8.00(2H, m).

REFERENCE EXAMPLE 39

(4-{[(2-phenylethyl)(4-phenyl-1,3-thiazol-2-yl)amino]methyl}phenyl)methanol

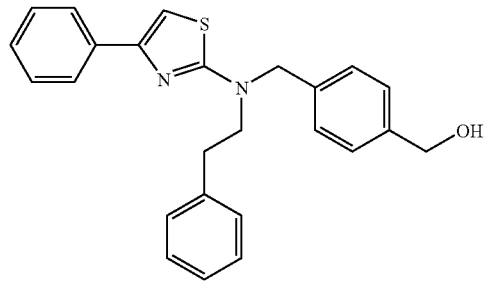

In the same manner as in Reference Example 41, the title compound was obtained as a colorless oil from methyl 4-{[(2-phenylethyl)(4-phenyl-1,3-thiazol-2-yl)amino]methyl}benzoate. yield 81%.

$^1$H NMR (CDCl$_3$) δ: 2.99(2H, t, J=8.1 Hz), 3.68(2H, t, J=8.1 Hz), 4.65-4.69(4H, m), 6.74(1H, s), 7.19-7.41(12H, m), 7.87-7.90(2H, m).

REFERENCE EXAMPLE 40 methyl 4-[(2-phenyl-1H-indol-1-yl)methyl]benzoate

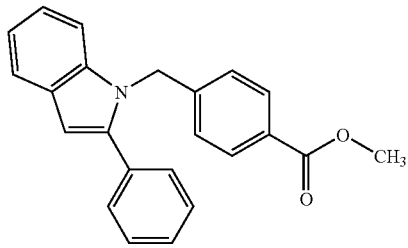

A solution of 2-phenylindole (4.2 g, 21.7 mmol) and sodium hydride (60% in oil, 0.96 g, 24 mmol) in a mixed solvent of tetrahydrofuran (90 mL) and N,N-dimethylformamide (10 mL) was stirred under ice-cooling for 20 min. Methyl 4-(bromomethyl)benzoate (5.0 g, 21.8 mmol) was added to the reaction mixture and the mixture was stirred at room temperature for 18 hr. Aqueous citric acid solution was added to the reaction mixture, and the mixture was extracted with ethyl acetate. The extract was washed with aqueous sodium chloride solution, dried over anhydrous magnesium sulfate and concentrated under reduced pressure. The obtained residue was subjected to silica gel chromatography (ethyl acetate:hexane=1:10-1:5-1:2) to give the title compound (2.8 g, yield 38%) as a pale-yellow oil.

MS m/z 242 (MH$^+$).

REFERENCE EXAMPLE 41

{4-[(2-phenyl-1H-indol-1-yl)methyl]phenyl}methanol

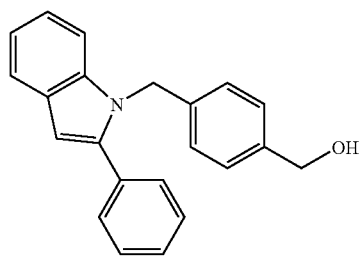

Methyl 4-[(2-phenyl-1H-indol-1-yl)methyl]benzoate (2.8 g, 8.20 mmol) was dissolved in anhydrous tetrahydrofuran (100 mL) and the mixture was ice-cooled. A solution (13.5 mL, 20.3 mmol) of 1.5 mol/L diisobutylaluminum hydride in toluene was added dropwise to the solution. This solution was stirred under ice-cooling for 4 hr, and aqueous citric acid solution was added to the reaction mixture, and the mixture was extracted with ethyl acetate. The extract was washed with aqueous sodium chloride solution, dried over anhydrous magnesium sulfate and concentrated under reduced pressure. The obtained residue was subjected to silica gel chromatography (ethyl acetate:hexane=1:4-1:2) to give the title compound (2.25 g, yield 88%) as a colorless oil.

MS m/z 314 (MH$^+$).

REFERENCE EXAMPLE 42

{4-[(2-methyl-1H-indol-1-yl)methyl]phenyl}methanol

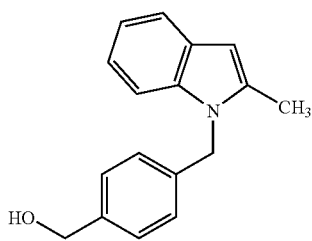

In the same manner as in Reference Examples 40 and 41, the title compound was obtained as pale-yellow crystals from 2-methylindole and methyl 4-(bromomethyl)benzoate. yield 14%

MS m/z 252 (MH$^+$).

REFERENCE EXAMPLE 43

4'-(benzyloxy)-2',6'-dimethyl-3-biphenylcarbaldehyde

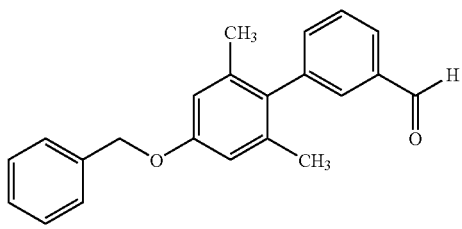

To a solution of 4'-hydroxy-2',6'-dimethyl-3-biphenylcarbaldehyde (2.26 g, 10.0 mmol) and benzyl bromide (3.42 g, 20.0 mmol) in N,N-dimethylformamide. (10 mL) was added potassium carbonate (2.76 g, 20.0 mmol), and the mixture was stirred at 70° C. for 2 hr. Water was added to the reaction mixture, and the mixture was extracted with ethyl acetate. The extract was washed with saturated brine, dried over anhydrous magnesium sulfate and concentrated under reduced pressure. The residue was purified by silica gel column chromatography (hexane-10% ethyl acetate/hexane) to give the title compound (2.90 g, yield 92%) as a colorless oil.

MS m/z 317 (MH$^+$).

REFERENCE EXAMPLE 44

[4'-(benzyloxy)-2',6'-dimethylbiphenyl-3-yl]methanol

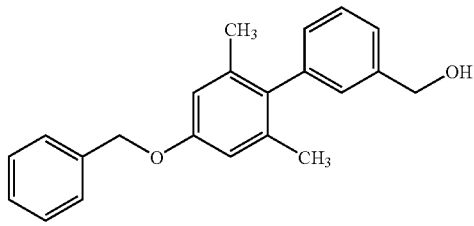

In the same manner as in Reference Example 6, the title compound was obtained as a colorless oil from 4'-(benzyloxy)-2',6'-dimethyl-3-biphenylcarbaldehyde. yield 95%.

$^1$H NMR (CDCl$_3$) δ: 1.65(1H, t, J=5.9 Hz), 2.01(6H, s), 4.73(2H, d, J=5.9 Hz), 5.07(2H, s), 6.75(2H, s), 7.07(1H, d, J=7.3 Hz), 7.13(1H, s), 7.30-7.48(7H, m).

REFERENCE EXAMPLE 45

4'-(2-ethoxyethoxy)-2',6'-dimethyl-3-biphenylcarbaldehyde

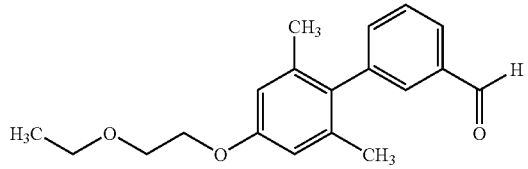

To a solution of 4'-hydroxy-2',6'-dimethyl-3-biphenylcarbaldehyde (8.52 g, 37.7 mmol) and 2-chloroethyl ethyl ether (6.15 g, 56.6 mmol) in N,N-dimethylformamide (40 mL) were added potassium carbonate (6.25 g, 45.2 mmol) and potassium iodide (1.25 g, 7.54 mmol), and the mixture was stirred at 80° C. for 18 hr. Water was added to the reaction mixture, and the mixture was extracted with ethyl acetate. The extract was washed with saturated brine, dried over anhydrous magnesium sulfate and concentrated under reduced pressure. The residue was purified by silica gel column chromatography (5%-25% ethyl acetate/hexane) to give the title compound (10.0 g, yield 89%) as a colorless oil.

MS m/z 299 (MH$^+$).

REFERENCE EXAMPLE 46

[4'-(2-ethoxyethoxy)-2',6'-dimethylbiphenyl-3-yl]methanol

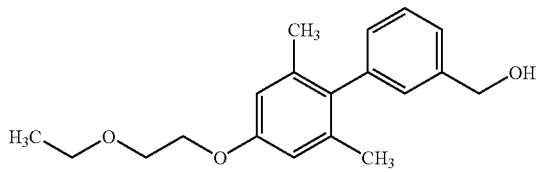

4'-(2-Ethoxyethoxy)-2',6'-dimethyl-3-biphenylcarbaldehyde (2.39 g, 9.70 mmol) was dissolved in a mixed solvent of 1,2-dimethoxyethane (20 mL) and tetrahydrofuran (20 mL), and sodium borohydride (0.227 g, 6.00 mmol) was added under ice-cooling, and the mixture was stirred at the same temperature for 3 hr. Aqueous ammonium chloride solution was added to the reaction mixture, and the mixture was extracted with ethyl acetate. The extract was washed with saturated brine, dried over anhydrous magnesium sulfate and concentrated under reduced pressure. The residue was purified by silica gel column chromatography (20%-50% ethyl acetate/hexane) to give the title compound (3.55 g, yield 98%) as colorless crystals.

MS m/z 301 (MH$^+$).

REFERENCE EXAMPLE 47

(6-benzyloxy-2',6'-dimethylbiphenyl-3-yl)methanol

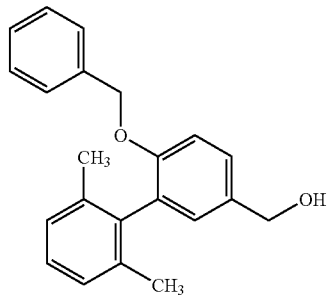

In the same manner as in Reference Examples 22 and 23, the title compound was obtained as a colorless oil from methyl 4-benzyloxy-3-bromobenzoate and (2,6-dimethylphenyl)boronic acid. yield 37%.

$^1$H NMR (CDCl$_3$) δ: 1.56(1H, t, J=5.6 Hz), 2.04(6H, s), 4.65(2H, d, J=5.6 Hz), 5.03(2H, s), 6.96-7.44(11H, m).

REFERENCE EXAMPLE 48

5-[(2',6'-dimethylbiphenyl-3-yl)methoxy]-1H-indole

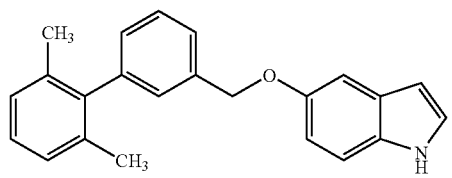

A solution of (2',6'-dimethylbiphenyl-3-yl)methanol (1.0 g, 4.71 mmol), 5-hydroxyindole (0.63 g, 4.73 mmol) and tributylphosphine (1.5 mL, 6.02 mmol) in tetrahydrofuran (30 mL) was stirred, and 1,1'-(azodicarbonyl)dipiperidine (1.6 g, 6.34 mmol) was added by portions, and the mixture was stirred at room temperature for 18 hr. Diethyl ether (30 mL) was added to the reaction mixture, and the precipitated insoluble material was filtered off, and the filtrate was concentrated under reduced pressure. The residue was purified by silica gel column chromatography (ethyl acetate:hexane=1:10-1:5) to give the title compound (0.95 g, yield 62%) as a pale-brown oil.

MS m/z 328 (MH$^+$).

REFERENCE EXAMPLE 49

2-amino-5,6-dihydro-1,3-benzothiazol-7(4H)-one hydrobromide

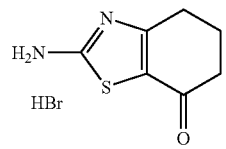

A mixture of 2-chloro-3-hydroxycyclohex-2-en-1-one (4.4 g, 30 mmol), thiourea (2.66 g, 35 mmol) and ethanol (15 mL) was heated under reflux for 1 hr. The reaction mixture was diluted with diisopropyl ether (50 mL), and the precipitated solid was collected by filtration, washed with diisopropyl ether, and air-dried to give the title compound (3.90 g, yield 52%) as colorless crystals.

$^1$H NMR (DMSO-d$_6$) δ: 2.0-2.2(2H, m), 2.44(2H, t, J=6.2 Hz), 2.77(2H, t, J=6.2 Hz), 9.38(3H, br s).

REFERENCE EXAMPLE 50

2-chloro-5,6-dihydro-1,3-benzothiazol-7-one

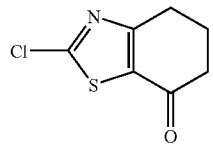

To a mixture of 2-amino-5,6-dihydro-1,3-benzothiazol-7-one hydrobromide (3.75 g, 15 mmol), anhydrous copper(II) chloride (2.01 g, 15 mmol), triethylamine (1.5 g, 15 mmol) and acetonitrile (50 mL) was added dropwise t-butyl nitrite (1.70 g, 16.5 mmol) under ice-cooling, and the mixture was stirred under ice-cooling for 1 hr. The reaction mixture was poured into water, and the mixture was extracted with ethyl acetate. The organic layer was washed successively with water and saturated brine, dried over anhydrous magnesium sulfate and concentrated under reduced pressure. The obtained residue was purified by silica gel column chromatography (AcOEt:hexane=1:19-1:1) to give the title compound (2.3 g, yield 82%) as a pale-yellow oil.

$^1$H NMR (CDCl$_3$) δ: 2.15-2.30(2H, m), 2.63(2H, t, J=6.1 Hz), 3.02(2H, t, J=6.1 Hz).

REFERENCE EXAMPLE 51

2-[(3-phenoxybenzyl)thio]-5,6-dihydro-1,3-benzothiazol-7(4H)-one

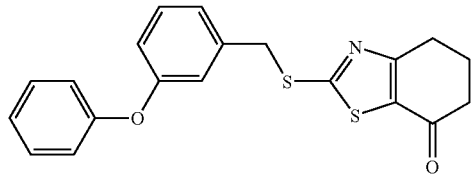

A mixture of 3-phenoxybenzyl chloride (2.84 g, 13.0 mmol), thiourea (1.22 g, 16 mmol) and ethanol (30 mL) was heated under reflux for 1 hr. 1 M aqueous sodium hydroxide solution (20 mL) was added to the reaction mixture and the mixture was further heated under reflux for 1 hr. The reaction mixture was cooled, and 2-chloro-5,6-dihydro-1,3-benzothiazol-7(4H)-one (1.55 g, 7.99 mmol) was added, and the mixture was stirred at room temperature for 3 hr. The reaction mixture was neutralized with 1 M hydrochloric acid, and the mixture was extracted with ethyl acetate. The organic layer was washed successively with water and saturated brine, dried over anhydrous magnesium sulfate and concentrated. The residue was purified by silica gel column chromatography (AcOEt:hexane=1:19-1:1) to give the title compound (2.67 g, yield 91%) as a pale-yellow oil.

$^1$H NMR (CDCl$_3$) δ: 2.12-2.23(2H, m), 2.55-2.62(2H, m), 2.96(2H, t, J=6.2 Hz), 4.44(2H, s), 6.90-6.96(1H, m), 6.97-7.04(2H, m), 7.04-7.17(3H, m), 7.27-7.39(3H, m).

REFERENCE EXAMPLE 52

2-[(3-phenoxybenzyl)thio]-4,5,6,7-tetrahydro-1,3-benzothiazol-7-ol

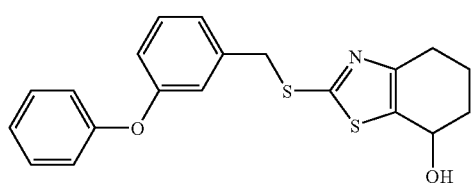

To a solution of 2-[(3-phenoxybenzyl)thio]-5,6-dihydro-1,3-benzothiazol-7(4H)-one (2.50 g, 6.80 mmol) in tetrahydrofuran (50 mL) was added by portions lithium aluminum hydride (280 mg) under ice-cooling, and the mixture was stirred at the same temperature for 1 hr. Sodium sulfate decahydrate (1.5 g) was added to reaction mixture, and the mixture was stirred at room temperature for 1 hr. The insoluble material was filtered off, and the filtrate was concentrated under reduced pressure to give the title compound (2.20 g, yield 87%) as a colorless oil.

$^1$H NMR (CDCl$_3$) δ: 1.77-2.11(5H, m), 2.59-2.85(2H, m), 4.35(2H, s), 4.85-4.92(1H, m), 6.87-6.93(1H, m), 6.96-7.04(3H, m), 7.07-7.15(2H, m), 7.23-7.37(3H, m).

REFERENCE EXAMPLE 53 diethyl {2-[(3-phenoxybenzyl)thio]-4,5,6,7-tetrahydro-1,3-benzothiazol-7-yl}malonate

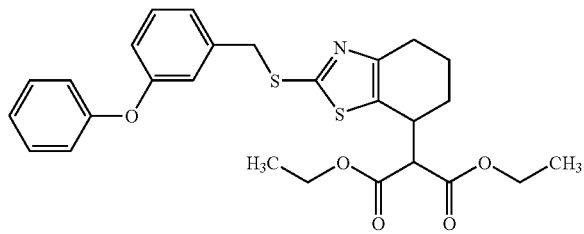

A mixture of 2-[(3-phenoxybenzyl)thio]-4,5,6,7-tetrahydro-1,3-benzothiazol-7-ol (2.00 g, 5.41 mmol), thionyl chloride (0.723 mL) and toluene (10 mL) was stirred at room temperature for 3 hr. The reaction mixture was concentrated, and the residue was dissolved in tetrahydrofuran (10 mL). The solution was added to a mixture of diethyl malonate (1.60 g, 10 mmol), sodium hydride (60% in oil, 400 mg) and tetrahydrofuran (20 mL) at room temperature, and the mixture was stirred at the same temperature for 3 hr. The reaction mixture was neutralized with 1 M hydrochloric acid and extracted with ethyl acetate. The organic layer was washed successively with water and saturated brine, dried over anhydrous magnesium sulfate and concentrated. The residue was purified by silica gel column chromatography (AcOEt:hexane=1:19-2:1) to give the title compound (2.73 g, quantitative) as a pale-yellow oil.

$^1$H NMR (CDCl$_3$) δ: 1.19-1.33(6H, m), 1.69-1.95(4H, m), 2.73(2H, t, J=4.9 Hz), 3.52(1H, d, J=9.0 Hz), 3.63-3.75(1H, m), 4.06-4.27(4H, m), 4.31(2H, s), 6.85-7.15(6H, m), 7.21-7.37(3H, m).

EXAMPLE 1 ethyl {6-[(3-phenoxybenzyl)oxy]-3,4-dihydronaphthalen-1-yl}acetate

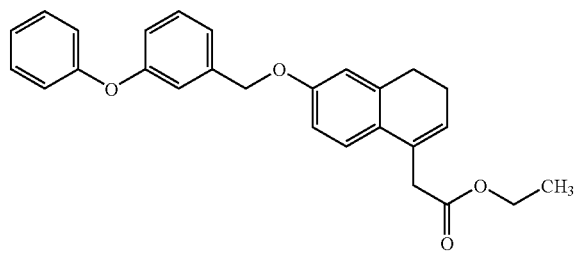

[Step 1]

To an ice-cooled solution of triethyl phosphonoacetate (20.2 g, 90.0 mmol) in toluene (100 mL) was added by portions sodium hydride (60% in oil, 3.60 g, 90.0 mmol), and the mixture was heated to 50° C. under nitrogen atmosphere and stirred for 1.5 hr. The reaction mixture was ice-cooled, and a solution of 6-methoxy-1-tetralone (10.6 g, 60.0 mmol) in toluene (100 mL) was added dropwise. The mixture was heated under reflux for 10 hr and cooled to room temperature. Water was added and the mixture was extracted with ethyl acetate. The extract was dried over anhydrous magnesium sulfate and concentrated under reduced pressure. The residue was purified by silica gel column chromatography (10%-50% ethyl acetate/hexane) to give a mixture (11.0 g) of ethyl (6-methoxy-3,4-dihydronaphthalen-1-yl)acetate and ethyl (2E)-(6-methoxy-3,4-dihydronaphthalen-1(2H)-ylidene)acetate as a pale-yellow oil.

[Step 2]

This product was dissolved in dichloromethane (300 mL), and a 1 M solution of boron tribromide in dichloromethane (135 mL, 135 mmol) was added dropwise under nitrogen atmosphere at −78° C. The mixture was stirred at the same temperature for 4 hr, warmed to room temperature and stirred for 1 hr. The reaction mixture was added to ice-cooled saturated aqueous sodium hydrogen carbonate solution, and the mixture was stirred at room temperature for 12 hr. The organic layer was separated, washed with saturated brine, dried over anhydrous magnesium sulfate and concentrated under reduced pressure. The residue was purified by silica gel column chromatography (15%-50% ethyl acetate/hexane) to give a mixture (5.5 g) of ethyl (6-hydroxy-3,4-dihydronaphthalen-1-yl)acetate and ethyl (2E)-(6-hydroxy-3,4-dihydronaphthalen-1(2H)-ylidene)acetate, as a pale-brown oil.

[Step 3]

This product was dissolved in toluene (25 mL), and 3-phenoxybenzyl alcohol (2.40 g, 12.0 mmol) and tributylphosphine (2.99 mL, 12.0 mmol) were added. The mixture was ice-cooled, and 1,1'-(azodicarbonyl)dipiperidine (3.03 g, 12.0 mmol) and tetrahydrofuran (150 mL) were added, and the mixture was stirred under nitrogen atmosphere at room temperature for 8 hr. The reaction mixture was concentrated under reduced pressure, and a mixed solvent of toluene/hexane (2:1) was added to the residue. The resulting insoluble material was filtered off. The filtrate was concentrated under reduced pressure, and the obtained residue was purified by silica gel column chromatography (5%-10% ethyl acetate/hexane) to give the title compound (2.33 g, yield 70%) as a main product as a colorless oil.

MS m/z 415 (MH$^+$).

EXAMPLE 2

{6-[(3-phenoxybenzyl)oxy]-3,4-dihydronaphthalen-1-yl}acetic acid

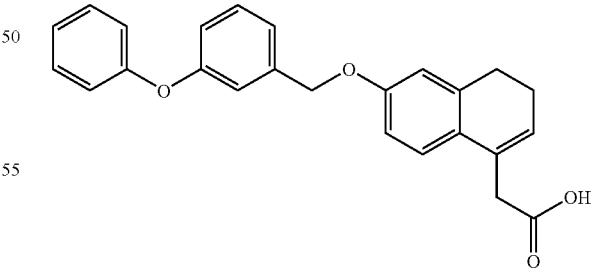

To a solution of ethyl {6-[(3-phenoxybenzyl)oxy]-3,4-dihydronaphthalen-1-yl}acetate (0.622 g, 1.50 mmol) in a mixed solvent of ethanol (3 mL) and tetrahydrofuran (3 mL) was added 2 M aqueous sodium hydroxide solution (3 mL), and the mixture was stirred at room temperature for 1 hr and further at 70° C. for 5 hr. Water was added to the reaction mixture, and the mixture was acidified with 1 M hydrochloric acid and extracted with ethyl acetate. The extract was washed with saturated brine, dried over anhydrous magnesium sulfate and concentrated under reduced pressure. The residue was purified by silica gel column chromatography (20%-80% ethyl acetate/hexane) and recrystallized from ethyl acetate-hexane to give the title compound (0.198 g, yield 34%) as colorless needle crystals.

MS m/z 387 (MH$^+$).

EXAMPLE 3 ethyl (2E)-[6-[(3-phenoxybenzyl)oxy]-3,4-dihydronaphthalen-1(2H)-ylidene]acetate

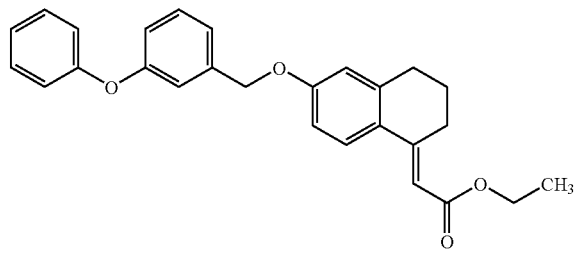

The title compound (0.42 g, 13%, colorless oil) was obtained as a byproduct of Example 1.

$^1$H NMR (CDCl$_3$) δ: 1.31(3H, t, J=7.2 Hz), 1.79-1.88(2H, m), 2.76(2H, t, J=6.1 Hz), 3.15-3.20(2H, m), 4.19(2H, q, J=7.2 Hz), 5.04(2H, s), 6.23(1H, s), 6.71(1H, d, J=2.5 Hz), 6.79(1H, dd, J=8.9, 2.5 Hz), 6.96(1H, dd, J=8.1, 1.9 Hz), 7.01(2H, dd, J=8.6, 1.0 Hz), 7.08-7.17(3H, m), 7.31-7.37(3H, m), 7.61(1H, d, J=8.9 Hz).

EXAMPLE 4

(2E)-[6-[(3-phenoxybenzyl)oxy]-3,4-dihydronaphthalen-1(2H)-yldene]acetic acid

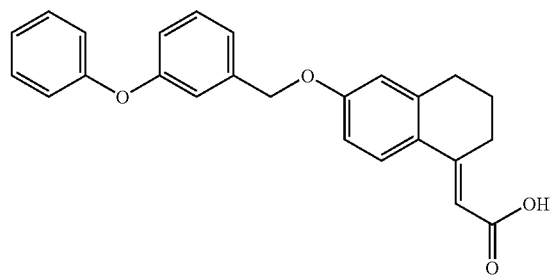

In the same manner as in Example 2, the title compound was obtained as colorless needle crystals from ethyl (2E)-[6-[(3-phenoxybenzyl)oxy]-3,4-dihydronaphthalen-1(2H)-ylidene]acetate. yield 41% (recrystallized from hexane-ethyl acetate).

MS m/z 387 (MH$^+$).

EXAMPLE 5 ethyl (6-((3-phenoxybenzyl)oxy)-1,2,3,4-tetrahydro-1-naphthalenyl)acetate

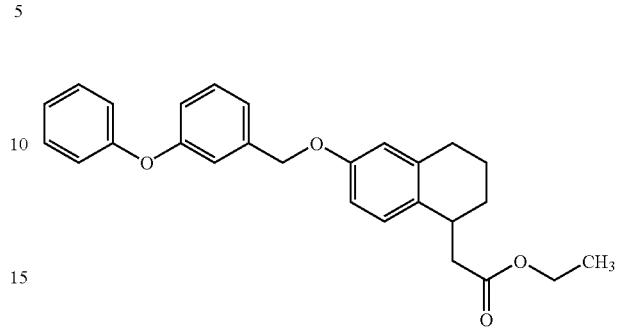

To a solution of ethyl (6-((3-phenoxybenzyl)oxy)-3,4-dihydro-1-naphthalenyl)acetate (1.04 g, 2.51 mmol) and 2,2'-bipyridyl (0.197 g, 1.26 mmol) in 1,4-dioxane (10 mL) was added 10% palladium on carbon (50%, water wet, 0.2 g), and the mixture was stirred under hydrogen atmosphere (balloon pressure) at room temperature for 24 hr. The catalyst was filtered off, and the filtrate was concentrated under reduced pressure. The residue was purified by silica gel column chromatography (hexane-30% ethyl acetate/hexane) to give the title compound (0.481 g, yield 46%) as a colorless oil.

MS m/z 417 (MH$^+$).

EXAMPLE 6

(6-((3-phenoxybenzyl)oxy)-1,2,3,4-tetrahydro-1-naphthalenyl)acetic acid

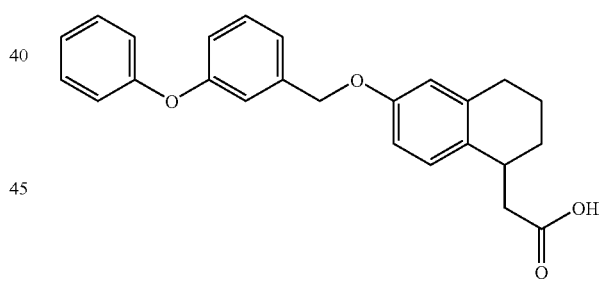

To a solution of ethyl (6-((3-phenoxybenzyl)oxy)-1,2,3,4-tetrahydro-1-naphthalenyl)acetate (0.481 g, 1.15 mmol) in a mixed solvent of ethanol (4 mL) and tetrahydrofuran (4 mL) was added 2 M aqueous sodium hydroxide solution (2 mL), and the mixture was stirred at room temperature for 9 hr. Water was added to the reaction mixture, and the mixture was neutralized with 10% aqueous citric acid solution and extracted with ethyl acetate. The extract was washed with saturated brine, dried over anhydrous magnesium sulfate and concentrated under reduced pressure. The residue was recrystallized from ethyl acetate-hexane to give the title compound (0.360 g, yield 81%) as colorless needle crystals.

$^1$H NMR (CDCl$_3$) δ: 1.68-2.00(4H, m), 2.56(1H, dd, J=15.5, 9.9 Hz), 2.65-2.81(3H, m), 3.27-3.35(1H, m), 4.99 (2H, s), 6.67(1H, d, J=2.6 Hz), 6.76(1H, dd, J=8.4, 2.6 Hz), 6.92-6.96(1H, m), 6.99-7.03(2H, m), 7.08-7.17(4H, m), 7.31-7.37(3H, m).

EXAMPLE 7

{6-[(3-phenoxybenzyl)oxy]-1H-inden-3-yl}acetic acid

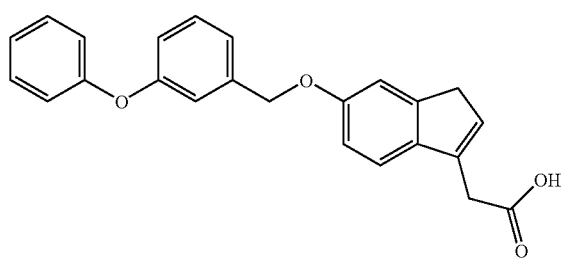

In the same manner as in Examples 1 and 2, the title compound was obtained as a pale-brown viscous oil from 5-methoxy-1-indanone and 3-phenoxybenzyl alcohol. yield 4%.

MS m/z 373 (MH$^+$).

EXAMPLE 8 ethyl 8-[(3-phenoxybenzyl)oxy]-2,3,4,5-tetrahydro-1-benzoxepine-4-carboxylate

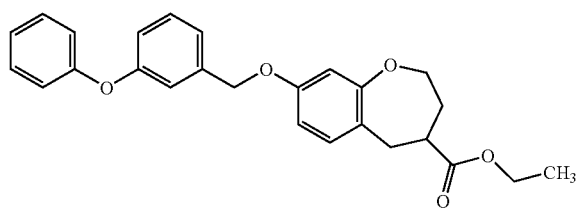

A solution of ethyl 8-hydroxy-2,3,4,5-tetrahydro-1-benzoxepine-4-carboxylate (0.189 g, 0.800 mmol), 3-phenoxybenzyl alcohol (0.240 g, 1.20 mmol) and tributylphosphine (0.299 mL, 1.20 mmol) in toluene (8 mL) was stirred under ice-cooling. 1,1'-(Azodicarbonyl)dipiperidine (0.279 g, 1.20 mmol) was added by small portions, and the mixture was stirred under nitrogen atmosphere at room temperature for 8 hr. Hexane (4 mL) was added to the reaction mixture, and the precipitated insoluble material was filtered off, and the filtrate was concentrated under reduced pressure. The residue was purified by silica gel column chromatography (5%-20% ethyl acetate/hexane) to give the title compound (0.20 g, yield 60%) as a colorless oil.

MS m/z 419 (MH$^+$).

EXAMPLE 9

8-[(3-phenoxybenzyl)oxy]-2,3,4,5-tetrahydro-1-benzoxepine-4-carboxylic acid

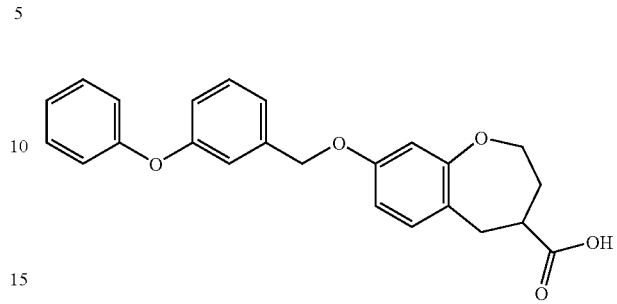

In the same manner as in Example 6, the title compound was obtained as colorless prism crystals from ethyl 8-[(3-phenoxybenzyl)oxy]-2,3,4,5-tetrahydro-1-benzoxepine-4-carboxylate. yield 87%.

MS m/z 391 (MH$^+$).

EXAMPLE 10 ethyl {6-[(2',6'-dimethylbiphenyl-3-yl)methoxy]-1,2,3,4-tetrahydronaphthalen-1-yl}acetate

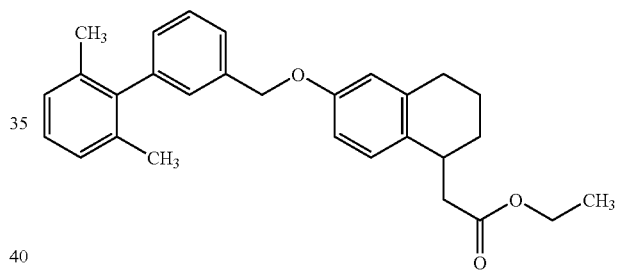

In the same manner as in Example 8, the title compound was obtained as a colorless oil from ethyl (6-hydroxy-1,2,3,4-tetrahydronaphthalen-1-yl)acetate and (2',6'-dimethylbiphenyl-3-yl)methanol. yield 23%.

MS m/z 429 (MH$^+$).

EXAMPLE 11

{6-[(2',6'-dimethylbiphenyl-3-yl)methoxy]-1,2,3,4-tetrahydronaphthalen-1-yl}acetic acid

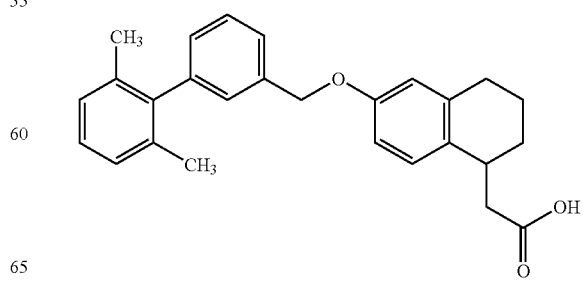

To a solution of ethyl (6-[(2',6'-dimethylbiphenyl-3-yl)methoxy]-1,2,3,4-tetrahydronaphthalen-1-yl)acetate (0.15 g, 0.35 mmol) in a mixed solvent of ethanol (1 mL) and tetrahydrofuran (1 mL) was added 2 M aqueous sodium hydroxide solution (0.5 mL), and the mixture was stirred at room temperature for 18 hr. Water was added to the reaction mixture, and the mixture was acidified with 1 M hydrochloric acid and extracted with ethyl acetate. The extract was washed with saturated brine, dried over anhydrous magnesium sulfate and concentrated under reduced pressure. The residue was recrystallized from ethyl acetate-hexane to give the title compound (0.08 g, yield 57%) as colorless prism crystals.

$^1$H NMR (CDCl$_3$) δ: 1.67-1.98(4H, m), 2.01(6H, s), 2.55 (1H, dd, J=15.5, 9.9 Hz), 2.70-2.77(3H, m), 3.26-3.34(1H, m), 5.08(2H, s), 6.68(1H, d, J=2.6 Hz), 6.78(1H, dd, J=8.5, 2.6 Hz), 7.07-7.19(6H, m), 7.37-7.46(2H, m).

EXAMPLE 12 ethyl 8-[(2',6'-dimethylbiphenyl-3-yl)methoxy]-2,3,4,5-tetrahydro-1-benzoxepine-4-carboxylate

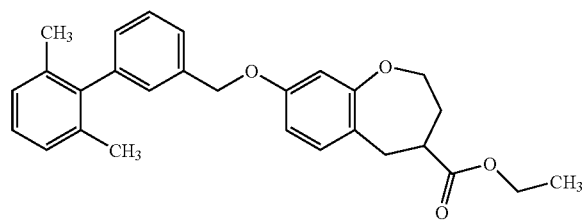

In the same manner as in Example 8, the title compound was obtained as a colorless oil from ethyl 8-hydroxy-2,3,4,5-tetrahydro-1-benzoxepine-4-carboxylate and (2',6'-dimethylbiphenyl-3-yl)methanol. yield 33%.

MS m/z 431 (MH$^+$).

EXAMPLE 13

8-[(2',6'-dimethylbiphenyl-3-yl)methoxy]-2,3,4,5-tetrahydro-1-benzoxepine-4-carboxylic acid

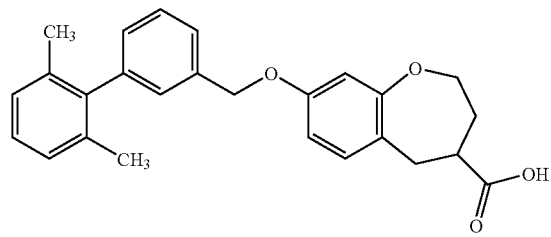

In the same manner as in Example 6, the title compound was obtained as colorless prism crystals from ethyl 8-[(2',6'-dimethylbiphenyl-3-yl)methoxy]-2,3,4,5-tetrahydro-1-benzoxepine-4-carboxylate. yield 87%.

MS m/z 403 (MH$^+$)

EXAMPLE 14 ethyl {5-[(3-phenoxybenzyl)oxy]-2,3-dihydro-1H-inden-1-yl}acetate

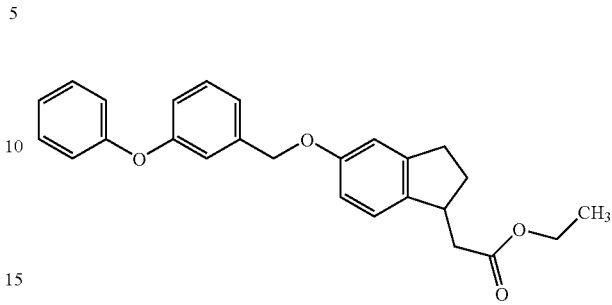

In the same manner as in Example 8, the title compound was obtained as a colorless oil from ethyl (5-hydroxy-2,3-dihydro-1H-inden-1-yl)acetate and 3-phenoxybenzyl alcohol. yield 83%.

MS m/z 403 (MH$^+$)

EXAMPLE 15

{5-[(3-phenoxybenzyl)oxy]-2,3-dihydro-1H-inden-1-yl}acetic acid

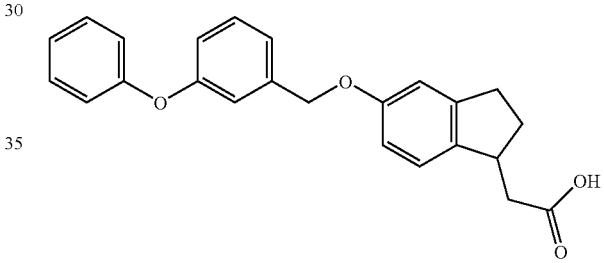

In the same manner as in Example 11, the title compound was obtained as colorless prism crystals from ethyl {5-[(3-phenoxybenzyl)oxy]-2,3-dihydro-1H-inden-1-yl}acetate. yield 79% (recrystallized from hexane-ethyl acetate).

$^1$H NMR (CDCl$_3$) δ: 1.72-1.84(1H, m), 2.37-2.52(2H, m), 2.76-2.97(3H, m), 3.49-3.59(1H, m), 5.01(2H, s), 6.77(1H, dd, J=8.3, 2.5 Hz), 6.83(1H, s), 6.94(1H, dd, J=8.0, 1.6 Hz), 6.99-7.04(2H, m), 7.08-7.17(4H, m), 7.31-7.37(3H, m).

EXAMPLE 16 ethyl {5-[(2',6'-dimethylbiphenyl-3-yl)methoxy]-2,3-dihydro-1H-inden-1-yl}acetate

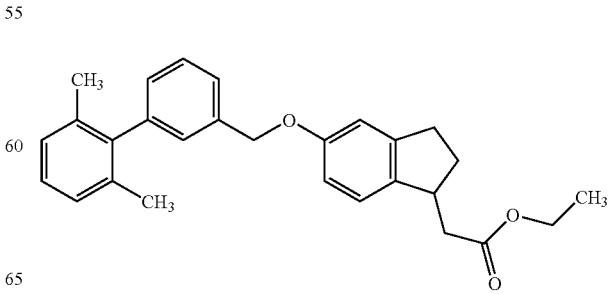

In the same manner as in Example 8, the title compound was obtained as a colorless oil from ethyl (5-hydroxy-2,3-dihydro-1H-inden-1-yl)acetate and (2',6'-dimethylbiphenyl-3-yl)methanol. yield 24%.

MS m/z 415 (MH⁺).

EXAMPLE 17

{5-[(2',6'-dimethylbiphenyl-3-yl)methoxy]-2,3-dihydro-1H-inden-1-yl}acetic acid

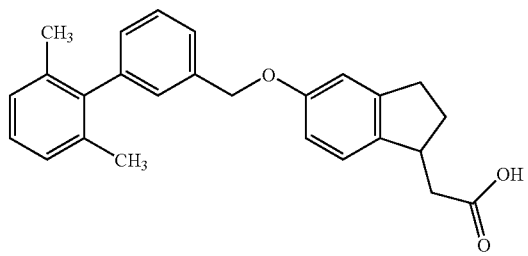

In the same manner as in Example 11, the title compound was obtained as colorless prism crystals from ethyl {5-[(2',6'-dimethylbiphenyl-3-yl)methoxy]-2,3-dihydro-1H-inden-1-yl}acetate. yield 53% (recrystallized from hexane-ethyl acetate).

¹H NMR (CDCl₃) δ: 1.71-1.83(1H, m), 2.01(6H, s), 2.36-2.51(2H, m), 2.76-2.96(3H, m), 3.49-3.58(1H, m), 5.09(2H, s), 6.79(1H, dd, J=8.3, 2.5 Hz), 6.85(1H, s), 7.08-7.17(5H, m), 7.20(1H, s), 7.38-7.47(2H, m).

EXAMPLE 18 ethyl {6-[(4-{[(4-phenyl-1,3-thiazol-2-yl)(propyl)amino]methyl}benzyl)oxy]-1,2,3,4-tetrahydronaphthalen-1-yl}acetate In the same manner as in Example 8, the title compound was obtained as a pale-yellow oil from ethyl (6-hydroxy-1,2,3,4-tetrahydronaphthalen-1-yl)acetate and (4-{[(4-phenyl-1,3-thiazol-2-yl)(propyl)amino]methyl}phenyl)methanol. yield 64%.

MS m/z 555 (MH⁺).

EXAMPLE 19

{6-[(4-{[(4-phenyl-1,3-thiazol-2-yl)(propyl)amino]methyl}benzyl)oxy]-1,2,3,4-tetrahydronaphthalen-1-yl}acetic acid

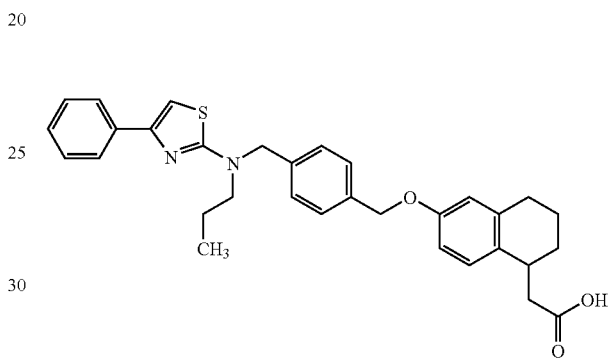

In the same manner as in Example 6, the title compound was obtained as a pale-yellow viscous oil from ethyl {6-[(4-{[(4-phenyl-1,3-thiazol-2-yl)(propyl)amino]methyl}benzyl)oxy]-1,2,3,4-tetrahydronaphthalen-1-yl}acetate. yield 99%.

MS m/z 527 (MH⁺).

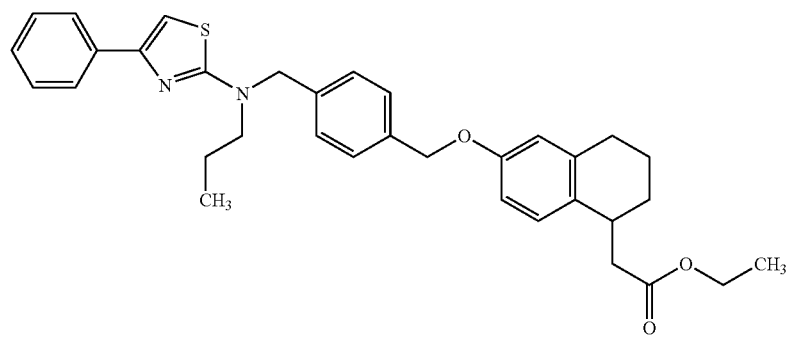

EXAMPLE 20 ethyl 8-[(4-{[(4-phenyl-1,3-thiazol-2-yl)(propyl)amino]methyl}benzyl)oxy]-2,3,4,5-tetrahydro-1-benzoxepine-4-carboxylate

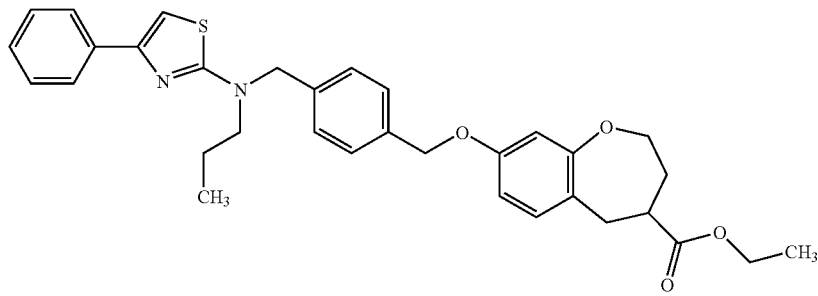

In the same manner as in Example 8, the title compound was obtained as a yellow oil from ethyl 8-hydroxy-2,3,4,5-tetrahydro-1-benzoxepine-4-carboxylate and (4-{[(4-phenyl-1,3-thiazol-2-yl)(propyl)amino]methyl}phenyl)methanol. yield 76%.

MS m/z 557 (MH$^+$).

EXAMPLE 21

8-[(4-{[(4-phenyl-1,3-thiazol-2-yl)(propyl)amino]methyl}benzyl)oxy]-2,3,4,5-tetrahydro-1-benzoxepine-4-carboxylic acid

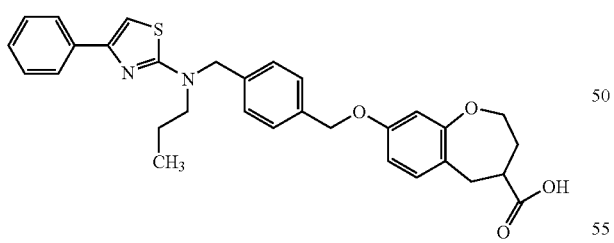

In the same manner as in Example 6, the title compound was obtained as colorless prism crystals from ethyl 8-[(4-{[(4-phenyl-1,3-thiazol-2-yl)(propyl)amino]methyl}benzyl)oxy]-2,3,4,5-tetrahydro-1-benzoxepine-4-carboxylate. yield 72% (recrystallized from hexane-ethyl acetate).

MS m/z 529 (MH$^+$).

EXAMPLE 22 ethyl {2-[(3-phenoxybenzyl)oxy]-6,7,8,9-tetrahydro-5H-benzo[7]annulen-5-yl}acetate

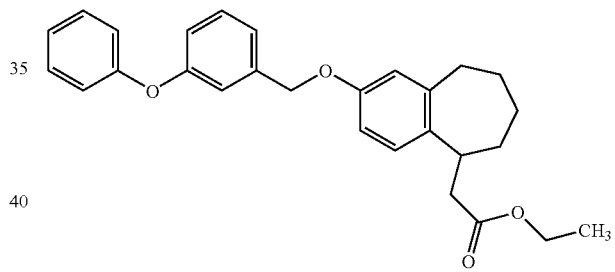

In the same manner as in Example 8, the title compound was obtained as a colorless oil from ethyl (2-hydroxy-6,7,8,9-tetrahydro-5H-benzo[7]annulen-5-yl)acetate and 3-phenoxybenzyl alcohol. yield 73%.

MS m/z 431 (MH$^+$)

EXAMPLE 23

{2-[(3-phenoxybenzyl)oxy]-6,7,8,9-tetrahydro-5H-benzo[7]annulen-5-yl}acetic acid

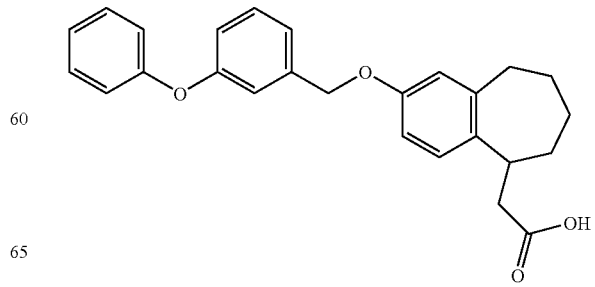

In the same manner as in Example 11, the title compound was obtained as colorless needle crystals from ethyl {2-[(3-phenoxybenzyl)oxy]-6,7,8,9-tetrahydro-5H-benzo[7]annulen-5-yl}acetate. yield 67% (recrystallized from hexane-ethyl acetate).

$^1$H NMR (CDCl$_3$) δ: 1.46-1.91(6H, m), 2.68-2.89(4H, m), 3.37-3.44(1H, m), 4.99(2H, s), 6.69(1H, dd, J=8.4, 2.7 Hz), 6.74(1H, d, J=2.7 Hz), 6.94(1H, dd, J=8.1, 1.9 Hz), 6.99-7.03 (3H, m), 7.08-7.17(3H, m), 7.31-7.36(3H, m).

EXAMPLE 24 ethyl {2-[(2',6'-dimethylbiphenyl-3-yl)methoxy]-6,7,8,9-tetrahydro-5H-benzo[7]annulen-5-yl}acetate

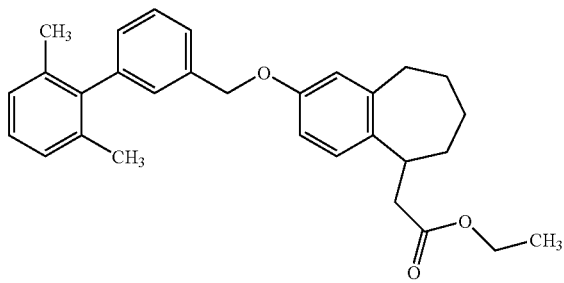

In the same manner as in Example 8, the title compound was obtained as a colorless oil from ethyl (2-hydroxy-6,7,8,9-tetrahydro-5H-benzo[7]annulen-5-yl)acetate and (2',6'-dimethylbiphenyl-3-yl)methanol. yield 72%.

MS m/z 443 (MH$^+$).

EXAMPLE 25

{2-[(2',6'-dimethylbiphenyl-3-yl)methoxy]-6,7,8,9-tetrahydro-5H-benzo[7]annulen-5-yl}acetic acid

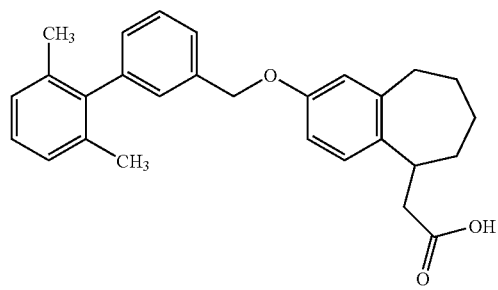

In the same manner as in Example 11, the title compound was obtained as a colorless crystalline powder from ethyl {2-[(2',6'-dimethylbiphenyl-3-yl)methoxy]-6,7,8,9-tetrahydro-5H-benzo[7]annulen-5-yl}acetate. yield 60% (recrystallized from hexane-ethyl acetate).

$^1$H NMR (CDCl$_3$) δ: 1.44-1.92(6H, m), 2.01(6H, s), 2.68-2.89(4H, m), 3.36-3.44(1H, m), 5.08(2H, s), 6.70-6.75(2H, m), 7.00(1H, d, J=8.3 Hz), 7.06-7.19(5H, m), 7.37-7.46(2H, m).

EXAMPLE 26 methyl {6-[(3-phenoxybenzyl)oxy]-1-benzofuran-3-yl}acetate

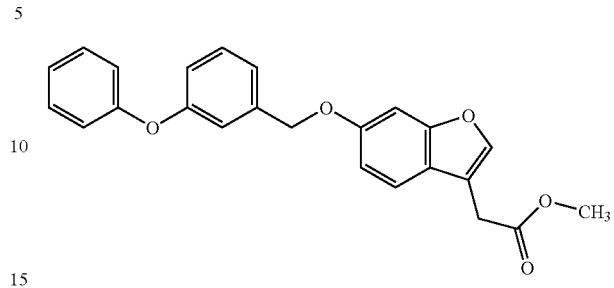

In the same manner as in Example 8, the title compound was obtained as a colorless oil from methyl (6-hydroxy-1-benzofuran-3-yl)acetate and 3-phenoxybenzyl alcohol. yield 91%.

MS m/z 389 (MH$^+$).

EXAMPLE 27

{6-[(3-phenoxybenzyl)oxy]-1-benzofuran-3-yl}acetic acid

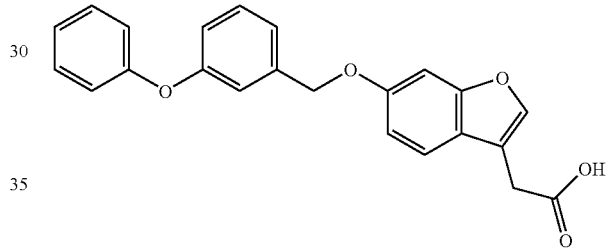

In the same manner as in Example 11, the title compound was obtained as colorless plate crystals from methyl {6-[(3-phenoxybenzyl)oxy]-1-benzofuran-3-yl}acetate. yield 77% (recrystallized from hexane-ethyl acetate).

MS m/z 375 (MH$^+$).

EXAMPLE 28 methyl {6-[(2',6'-dimethylbiphenyl-3-yl)methoxy]-1-benzofuran-3-yl}acetate

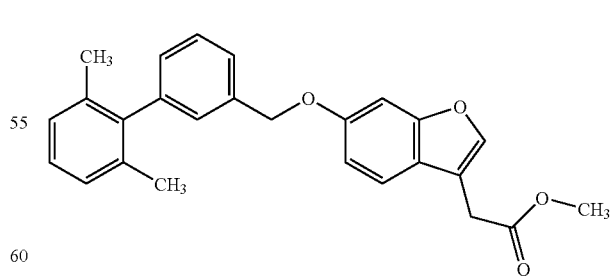

In the same manner as in Example 8, the title compound was obtained as a colorless oil from methyl (6-hydroxy-1-benzofuran-3-yl)acetate and (2',6'-dimethylbiphenyl-3-yl)methanol. yield 96%.

MS m/z 401 (MH$^+$).

EXAMPLE 29

{6-[(2',6'-dimethylbiphenyl-3-yl)methoxy]-1-benzo-furan-3-yl}acetic acid

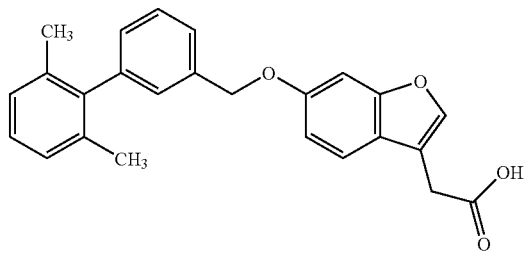

In the same manner as in Example 11, the title compound was obtained as colorless-plate crystals from methyl {6-[(2',6'-dimethylbiphenyl-3-yl)methoxy]-1-benzofuran-3-yl}acetate. yield 80% (recrystallized from hexane-ethyl acetate).
MS m/z 387 (MH$^+$).

EXAMPLE 30 methyl {6-[(3-phenoxybenzyl)oxy]-2,3-dihydro-1-benzofuran-3-yl}acetate

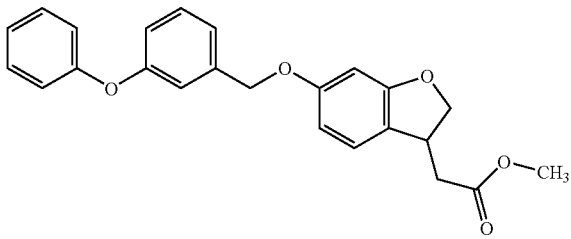

In the same manner as in Example 8, the title compound was obtained as a colorless oil from methyl (6-hydroxy-2,3-dihydro-1-benzofuran-3-yl)acetate and 3-phenoxybenzyl alcohol. yield 77%.
MS m/z 391 (MH$^+$).

EXAMPLE 31

{6-[(3-phenoxybenzyl)oxy]-2,3-dihydro-1-benzofuran-3-yl}acetic acid

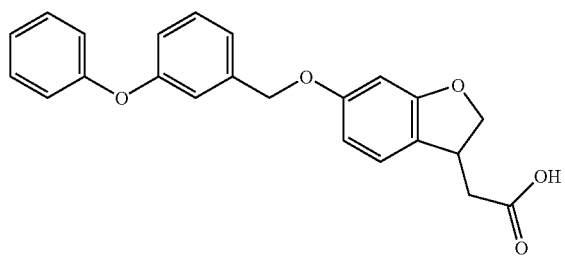

In the same manner as in Example 11, the title compound was obtained as colorless needle crystals from methyl {6-[(3-phenoxybenzyl)oxy]-2,3-dihydro-1-benzofuran-3-yl}acetate. yield 78% (recrystallized from hexane-ethyl acetate).
MS m/z 377 (MH$^+$).

EXAMPLE 32 methyl {6-[(2',6'-dimethylbiphenyl-3-yl)methoxy]-2,3-dihydro-1-benzofuran-3-yl}acetate

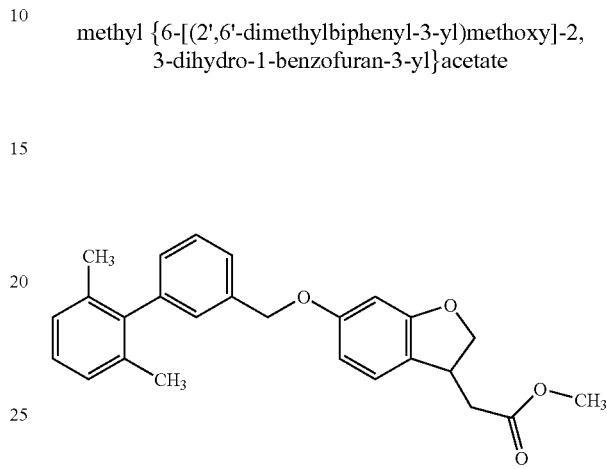

In the same manner as in Example 8, the title compound was obtained as a colorless oil from methyl (6-hydroxy-2,3-dihydro-1-benzofuran-3-yl)acetate and (2',6'-dimethylbiphenyl-3-yl)methanol. yield 72%.
MS m/z 403 (MH$^+$).

EXAMPLE 33

{6-[(2',6'-dimethylbiphenyl-3-yl)methoxy]-2,3-dihydro-1-benzofuran-3-yl}acetic acid

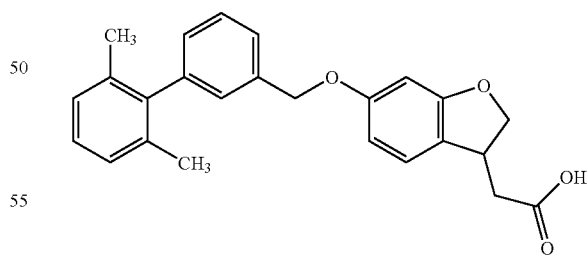

In the same manner as in Example 11, the title compound was obtained as colorless needle crystals from methyl {6-[(2',6'-dimethylbiphenyl-3-yl)methoxy]-2,3-dihydro-1-benzofuran-3-yl}acetate. yield 73% (recrystallized from hexane-ethyl acetate).
MS m/z 389 (MH$^+$).

EXAMPLE 34 methyl {6-[(4-{[(4-phenyl-1,3-thiazol-2-yl)(propyl)amino]methyl}benzyl)oxy]-2,3-dihydro-1-benzofuran-3-yl}acetate

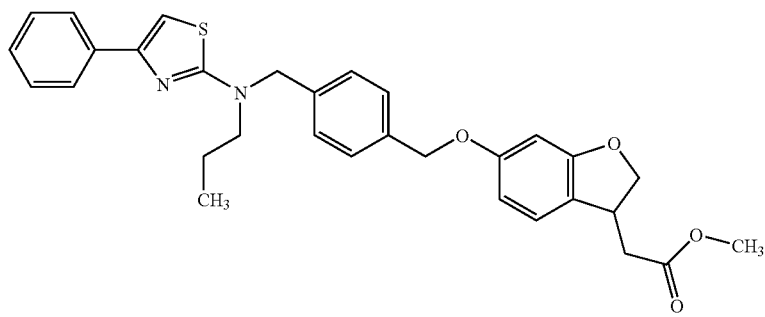

In the same manner as in Example 8, the title compound was obtained as a colorless oil from methyl (6-hydroxy-2,3-dihydro-1-benzofuran-3-yl)acetate and (4-{[(4-phenyl-1,3-thiazol-2-yl)(propyl)amino]methyl}phenyl)methanol. yield 73%.

MS m/z 529 (MH$^+$).

EXAMPLE 35

{6-[(4-{[(4-phenyl-1,3-thiazol-2-yl)(propyl)amino]methyl}benzyl)oxy]-2,3-dihydro-1-benzofuran-3-yl}acetic acid

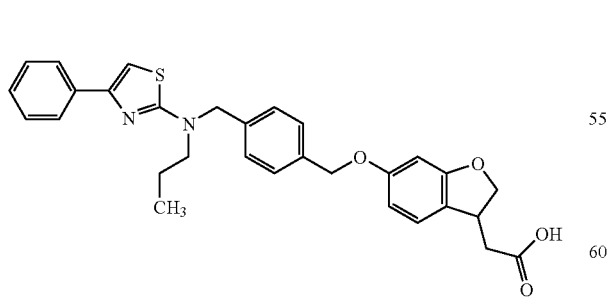

In the same manner as in Example 6, the title compound was obtained as a pale-green crystalline powder from methyl {6-[(4-{[(4-phenyl-1,3-thiazol-2-yl)(propyl)amino]methyl}benzyl)oxy]-2,3-dihydro-1-benzofuran-3-yl}acetate. yield 65% (recrystallized from hexane-ethyl acetate).

MS m/z 515 (MH$^+$).

EXAMPLE 36 methyl {6-[(2',4'-dimethylbiphenyl-3-yl)methoxy]-2,3-dihydro-1-benzofuran-3-yl}acetate

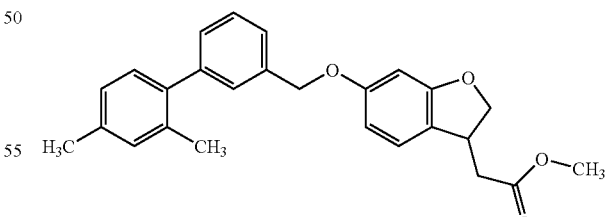

In the same manner as in Example 8, the title compound was obtained as a colorless oil from methyl (6-hydroxy-2,3-dihydro-1-benzofuran-3-yl)acetate and (2',4'-dimethylbiphenyl-3-yl)methanol. yield 67%.

MS m/z 403 (MH$^+$)

EXAMPLE 37

{6-[(2',4'-dimethylbiphenyl-3-yl)methoxy]-2,3-dihydro-1-benzofuran-3-yl}acetic acid

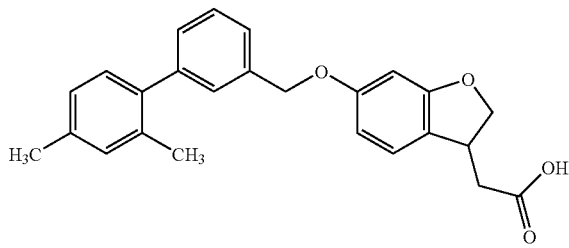

In the same manner as in Example 11, the title compound was obtained as colorless prism crystals from methyl (6-((2',4'-dimethyl-1,1'-biphenyl-3-yl)methoxy)-2,3-dihydro-1-benzofuran-3-yl)acetate. yield 92% (recrystallized from hexane-ethyl acetate).
MS m/z 389 (MH$^+$).

EXAMPLE 38 methyl {6-[(2',4',6'-trimethylbiphenyl-3-yl)methoxy]-2,3-dihydro-1-benzofuran-3-yl}acetate

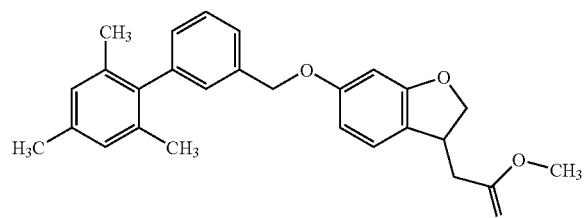

In the same manner as in Example 8, the title compound was obtained as a colorless oil from methyl (6-hydroxy-2,3-dihydro-1-benzofuran-3-yl)acetate and (2',4',6'-trimethylbiphenyl-3-yl)methanol. yield 78%.
MS m/z 417 (MH$^+$).

EXAMPLE 39

{6-[(2',4',6'-trimethylbiphenyl-3-yl)methoxy]-2,3-dihydro-1-benzofuran-3-yl}acetic acid

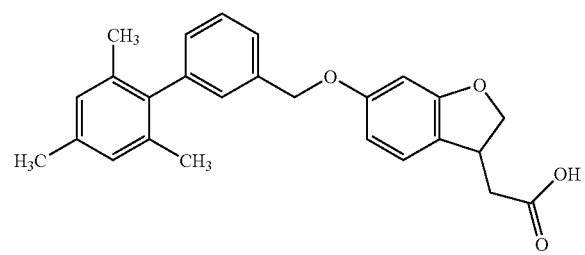

In the same manner as in Example 11, the title compound was obtained as colorless plate crystals from methyl {6-[(2',4',6'-trimethylbiphenyl-3-yl)methoxy]-2,3-dihydro-1-benzofuran-3-yl}acetate. yield 75% (recrystallized from hexane-ethyl acetate).
MS m/z 403 (MH$^+$).

EXAMPLE 40 methyl {6-[(6-methoxy-2',6'-dimethylbiphenyl-3-yl)methoxy]-2,3-dihydro-1-benzofuran-3-yl}acetate

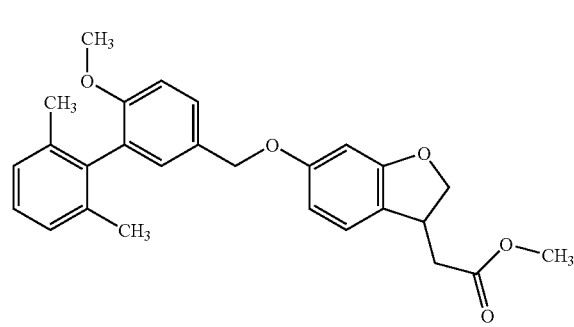

In the same manner as in Example 8, the title compound was obtained as a colorless oil from methyl (6-hydroxy-2,3-dihydro-1-benzofuran-3-yl)acetate and (6-methoxy-2',6'-dimethylbiphenyl-3-yl)methanol. yield 73%.
$^1$H NMR (CDCl$_3$) δ: 2.00(6H, s), 2.55(1H, dd, J=16.4, 9.2 Hz), 2.74(1H, dd, J=16.4, 5.4 Hz), 3.71(3H, s), 3.74(3H, s), 3.77-3.85(1H, m), 4.25(1H, dd, J=9.2, 6.0 Hz), 4.74(1H, t, J=9.2 Hz), 4.97(2H, s), 6.45-6.49(2H, m), 6.97-7.03(2H, m), 7.07-7.18(4H, m), 7.39(1H, dd, J=8.4, 2.2 Hz).

EXAMPLE 41

{6-[(6-methoxy-2',6'-dimethylbiphenyl-3-yl)methoxy]-2,3-dihydro-1-benzofuran-3-yl}acetic acid

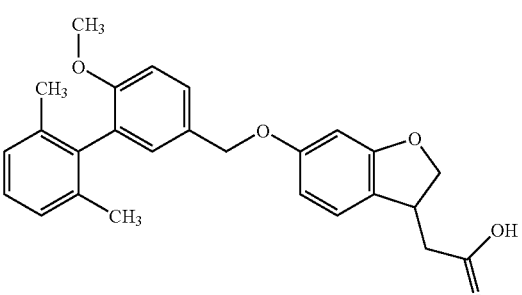

In the same manner as in Example 11, the title compound was obtained as colorless prism crystals from methyl {6-[(6-methoxy-2',6'-dimethylbiphenyl-3-yl)methoxy]-2,3-dihydro-1-benzofuran-3-yl}acetate. yield 58% (recrystallized from hexane-ethyl acetate).
$^1$H NMR (CDCl$_3$) δ: 2.00(6H, s), 2.61(1H, dd, J=16.8, 9.2 Hz), 2.80(1H, dd, J=16.8, 5.4 Hz), 3.74(3H, s), 3.77-3.85(1H, m), 4.28(1H, dd, J=9.2, 6.0 Hz), 4.75(1H, t, J=9.2 Hz), 4.98 (2H, s), 6.45-6.50(2H, m), 6.97-7.19(6H, m), 7.39(1H, dd, J=8.5, 2.3 Hz).

EXAMPLE 42 methyl (6-((3-(1-benzothien-5-yl)benzyl)oxy)-2,3-dihydro-1-benzofuran-3-yl)acetate

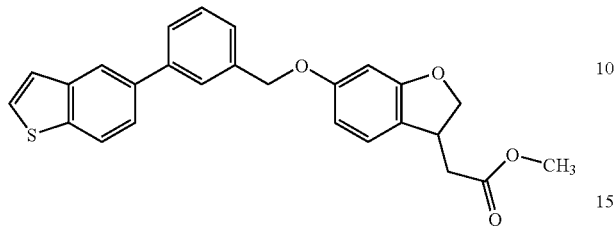

In the same manner as in Example 8, the title compound was obtained as a colorless oil from methyl (6-hydroxy-2,3-dihydro-1-benzofuran-3-yl)acetate and [3-(1-benzothien-5-yl)phenyl]methanol. yield 74%.

MS m/z 431 (MH$^+$).

EXAMPLE 43

(6-{[3-(1-benzothien-5-yl)benzyl]oxy}-2,3-dihydro-1-benzofuran-3-yl)acetic acid

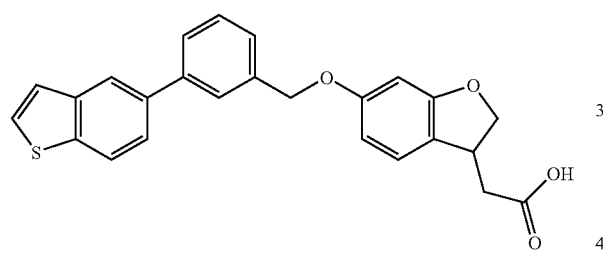

In the same manner as in Example 11, the title compound was obtained as colorless plate crystals from methyl (6-{[3-(1-benzothien-5-yl)benzyl]oxy}-2,3-dihydro-1-benzofuran-3-yl)acetate. yield 84% (recrystallized from hexane-ethyl acetate).

MS m/z 417 (MH$^+$).

EXAMPLE 44 methyl (6-{[3-(1-benzothien-3-yl)benzyl]oxy}-2,3-dihydro-1-benzofuran-3-yl)acetate

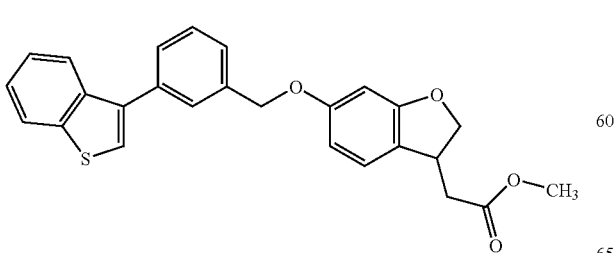

In the same manner as in Example 8, the title compound was obtained as a colorless oil from methyl (6-hydroxy-2,3-dihydro-1-benzofuran-3-yl)acetate and [3-(1-benzothien-3-yl)phenyl]methanol. yield 72%.

MS m/z 431 (MH$^+$).

EXAMPLE 45

(6-{[3-(1-benzothien-3-yl)benzyl]oxy}-2,3-dihydro-1-benzofuran-3-yl)acetic acid

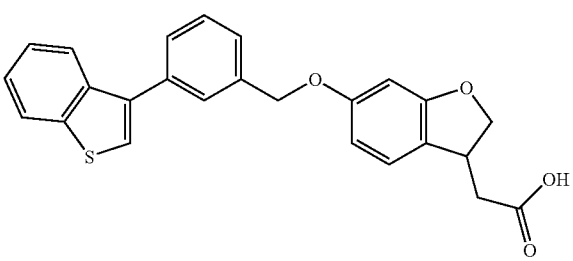

In the same manner as in Example 11, the title compound was obtained as colorless needle crystals from methyl (6-{[3-(1-benzothien-3-yl)benzyl]oxy}-2,3-dihydro-1-benzofuran-3-yl)acetate. yield 69% (recrystallized from hexane-ethyl acetate).

MS m/z 417 (MH$^+$).

EXAMPLE 46 methyl (6-{[3-(2-methyl-1 naphthyl)benzyl]oxy}-2,3-dihydro-1-benzofuran-3-yl)acetate

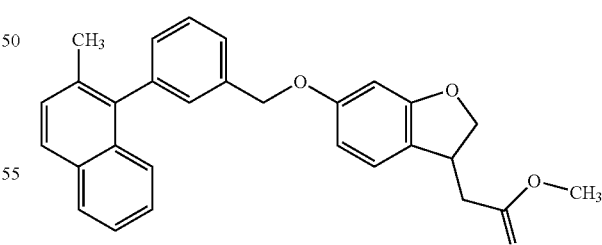

In the same manner as in Example 8, the title compound was obtained as a colorless oil from methyl (6-hydroxy-2,3-dihydro-1-benzofuran-3-yl)acetate and [3-(2-methyl-1-naphthyl)phenyl]methanol. yield 91%.

MS m/z 439 (MH$^+$).

EXAMPLE 47

(6-{[3-(2-methyl-1-naphthyl)benzyl]oxy}-2,3-dihydro-1-benzofuran-3-yl)acetic acid

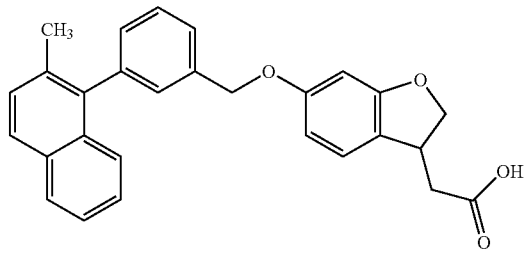

To a solution of methyl (6-{[3-(2-methyl-1-naphthyl)benzyl]oxy}-2,3-dihydro-1-benzofuran-3-yl)acetate (0.801 g, 1.90 mmol) in a mixed solvent of methanol (6 mL) and tetrahydrofuran (6 mL) was added 2 M aqueous sodium hydroxide solution (3 mL), and the mixture was stirred at room temperature for 20 hr. Water was added to the reaction mixture, and the mixture was acidified with 1 M hydrochloric acid and extracted with ethyl acetate. The extract was washed with saturated brine, dried over anhydrous magnesium sulfate and concentrated under reduced pressure. The residue was purified by silica gel column chromatography (30% ethyl acetate/hexane-ethyl acetate), and recrystallized from ethyl acetate-hexane to give the title compound (0.444 g, yield 55%) as colorless needle crystals.

MS m/z 425 (MH$^+$).

EXAMPLE 48 ethyl {5-[(4-{[(4-phenyl-1,3-thiazol-2-yl)(propyl)amino]methyl}benzyl)oxy]-2,3-dihydro-1H-indn-1-yl}acetate

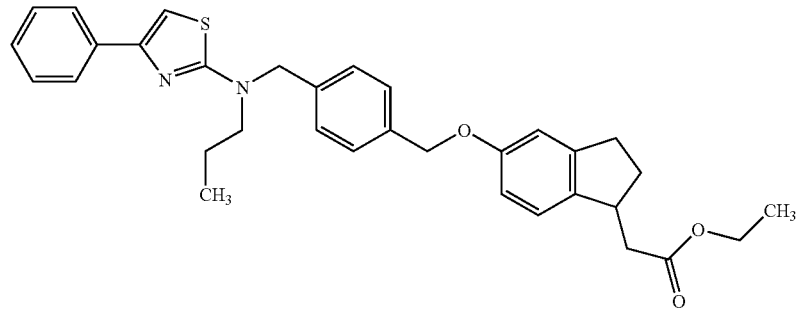

In the same manner as in Example 8, the title compound was obtained as a colorless oil from ethyl (5-hydroxy-2,3-dihydro-1H-inden-1-yl)acetate and (4-{[(4-phenyl-1,3-thiazol-2-yl)(propyl)amino]methyl}phenyl)methanol. yield 70%.

MS m/z 541 (MH$^+$).

EXAMPLE 49

{5-[(4-{[(4-phenyl-1,3-thiazol-2-yl)(propyl)amino]methyl}benzyl)oxy]-2,3-dihydro-1H-inden-1-yl}acetic acid

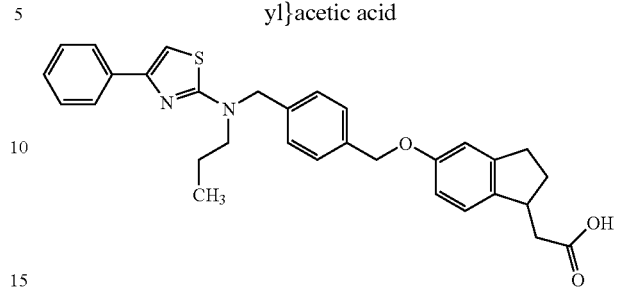

To a solution of ethyl {5-[(4-{[(4-phenyl-1,3-thiazol-2-yl)(propyl)amino]methyl}benzyl)oxy]-2,3-dihydro-1H-inden-1-yl}acetate (0.684 g, 1.17 mmol) in a mixed solvent of ethanol (6 mL) and tetrahydrofuran (6 mL) was added 2 M aqueous sodium hydroxide solution (2 mL), and the mixture was stirred at room temperature for 24 hr. Water was added to the reaction mixture, and the mixture was neutralized with 10% aqueous citric acid solution and extracted with ethyl acetate. The extract was washed with saturated brine, dried over anhydrous magnesium sulfate and concentrated under reduced pressure. The residue was purified by silica gel column chromatography (30%-80% ethyl acetate/hexane) and recrystallized from ethyl acetate-hexane to give the title compound (0.393 g, yield 66%) as colorless prism crystals.

MS m/z 513 (MH$^+$).

EXAMPLE 50 methyl (6-{[2'-methyl-4'-(tetrahydro-2H-pyran-2-yloxy)biphenyl-3-yl]methoxy}-2,3-dihydro-1-benzofuran-3-yl)acetate

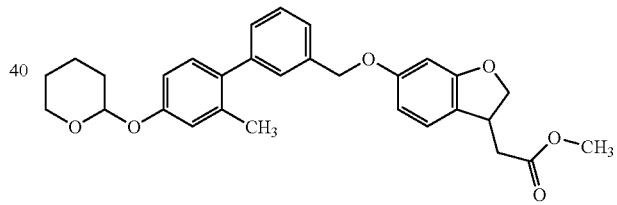

In the same manner as in Example 8, the title compound was obtained as a colorless oil from methyl (6-hydroxy-2,3-dihydro-1-benzofuran-3-yl)acetate and [2'-methyl-4'-(tetrahydro-2H-pyran-2-yloxy)biphenyl-3-yl]methanol. yield 84%.

MS m/z 489 (MH$^+$).

EXAMPLE 51 methyl {6-[(4'-hydroxy-2'-methylbiphenyl-3-yl)methoxy]-2,3-dihydro-1-benzofuran-3-yl}acetate

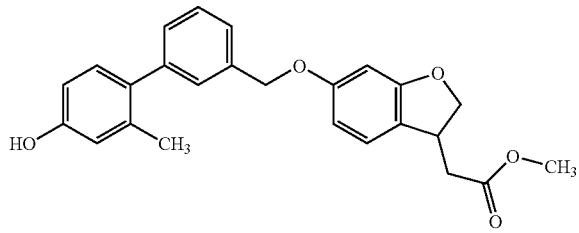

A solution of methyl (6-{[2'-methyl-4'-(tetrahydro-2H-pyran-2-yloxy)biphenyl-3-yl]methoxy}-2,3-dihydro-1-benzofuran-3-yl)acetate (4.49 g, 9.19 mmol) and p-toluenesulfonic acid monohydrate (0.175 g, 0.919 mmol) in methanol (50 mL) was stirred at room temperature for 30 hr. The reaction solvent was evaporated under reduced pressure, and the residue was diluted with ethyl acetate, washed with saturated brine, dried over anhydrous magnesium sulfate and concentrated under reduced pressure. The residue was purified by silica gel column chromatography (20%-60% ethyl acetate/hexane) to give the title compound (3.21 g, yield 86%) as a colorless viscous oil.
MS m/z 405 (MH+).

EXAMPLE 52

{6-[(4'-hydroxy-2'-methylbiphenyl-3-yl)methoxy]-2,3-dihydro-1-benzofuran-3-yl}acetic acid

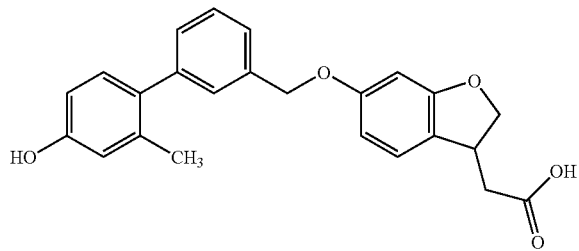

In the same manner as in Example 11, the title compound was obtained as colorless prism crystals from methyl {6-[(4'-hydroxy-2'-methylbiphenyl-3-yl)methoxy]-2,3-dihydro-1-benzofuran-3-yl}acetate. yield 45% (recrystallized from hexane-ethyl acetate).
m/z 391 (MH+).

EXAMPLE 53 methyl {6-[(4'-methoxy-2'-methylbiphenyl-3-yl)methoxy]-2,3-dihydro-1-benzofuran-3-yl}acetate

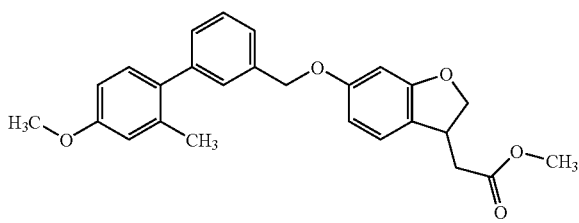

In the same manner as in Example 8, the title compound was obtained as a colorless oil from methyl {6-[(4'-hydroxy-2'-methylbiphenyl-3-yl)methoxy]-2,3-dihydro-1-benzofuran-3-yl}acetate and methanol. yield 97%.
MS m/z 419 (MH+).

EXAMPLE 54

{6-[(4'-methoxy-2'-methylbiphenyl-3-yl)methoxy]-2,3-dihydro-1-benzofuran-3-yl}acetic acid

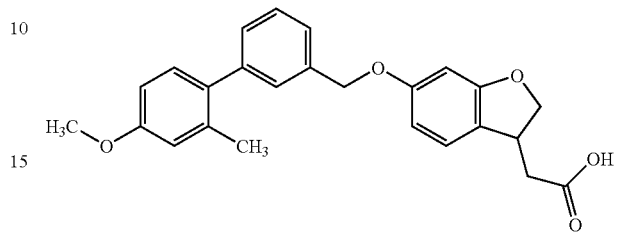

In the same manner as in Example 6, the title compound was obtained as colorless prism crystals from methyl {6-[(4'-methoxy-2'-methylbiphenyl-3-yl)methoxy]-2,3-dihydro-1-benzofuran-3-yl}acetate. yield 82% (recrystallized from hexane-ethyl acetate).
MS m/z 405 (MH+).

EXAMPLE 55 methyl (6-{[4'-(cyclopropylmethoxy)-2'-methylbiphenyl-3-yl]methoxy}-2,3-dihydro-1-benzofuran-3-

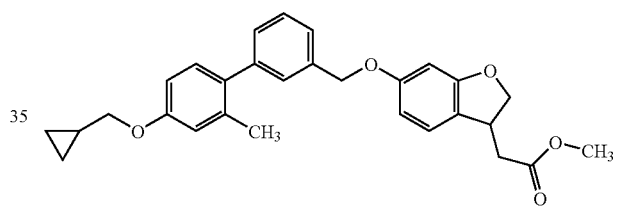

In the same manner as in Example 8, the title compound was obtained as colorless oil from methyl {6-[(4'-hydroxy-2'-methylbiphenyl-3-yl)methoxy]-2,3-dihydro-1-benzofuran-3-yl}acetate and cyclopropylmethanol. yield 81%.
MS m/z 459 (MH+).

EXAMPLE 56

(6-{[4'-(cyclopropylmethoxy)-2'-methylbiphenyl-3-yl]methoxy}-2,3-dihydro-1-benzofuran-3-yl)acetic acid

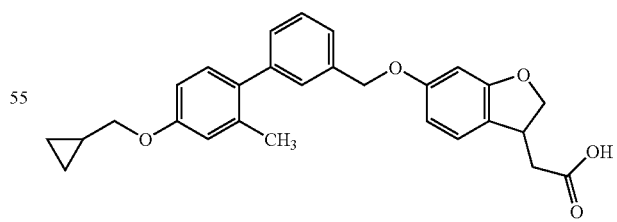

In the same manner as in Example 6, the title compound was obtained as a colorless prism crystals from methyl (6-{[4'-(cyclopropylmethoxy)-2'-methylbiphenyl-3-yl]methoxy}-2,3-dihydro-1-benzofuran-3-yl)acetate. yield 63% (recrystallized from hexane-ethyl acetate).
MS m/z 445 (MH+).

EXAMPLE 57 methyl (6-{[4'-(2-butoxyethoxy)-2'-methylbiphenyl-3-yl]methoxy}-2,3-dihydro-1-benzofuran-3-yl)acette

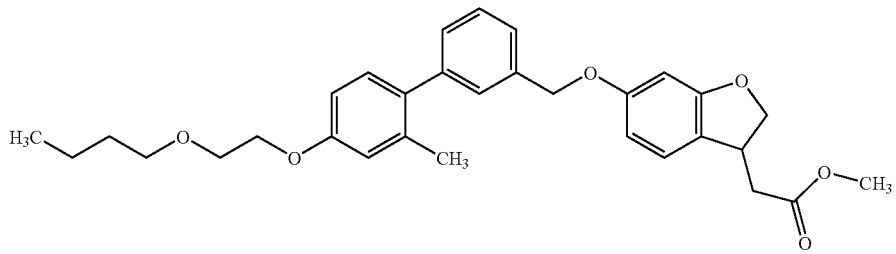

In the same manner as in Example 8, the title compound was obtained as a colorless oil from methyl {6-[(4'-hydroxy-2'-methylbiphenyl-3-yl)methoxy]-2,3-dihydro-1-benzofuran-3-yl}acetate and 2-butoxyethanol. yield 72%.
MS m/z 505 (MH$^+$).

EXAMPLE 58

(6-{[4'-(2-butoxyethoxy)-2'-methylbiphenyl-3-yl]methoxy}-2,3-dihydro-1-benzofuran-3-yl)acetic acid

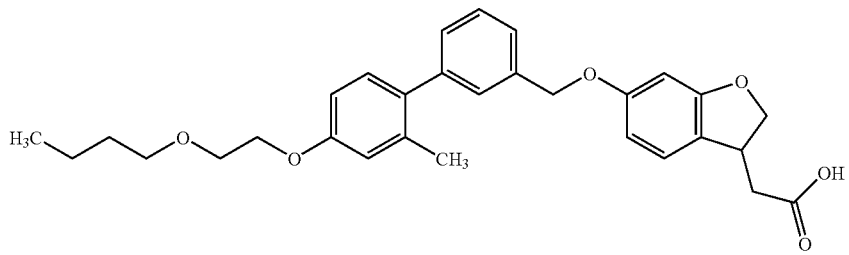

In the same manner as in Example 49, the title compound as obtained as colorless crystals from methyl (6-{[4'-(2-butoxyethoxy)-2'-methylbiphenyl-3-yl]methoxy}-2,3-dihydro-1-benzofuran-3-yl)acetate. yield 83% (recrystallized from heptane).
MS m/z 491 (MH$^+$).

EXAMPLE 59 methyl (6-{[2'-methyl-4'-(1-propylbutoxy)biphenyl-3-yl]methoxy}-2,3-dihydro-1-benzofuran-3-yl)acetate

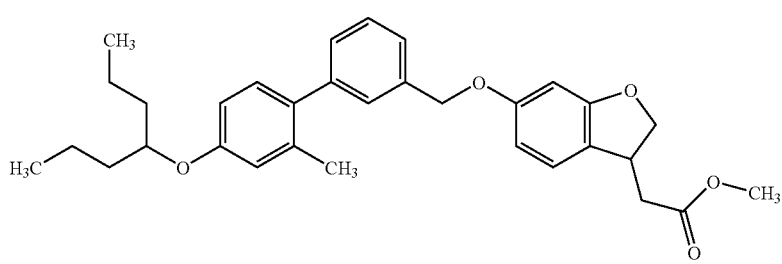

In the same manner as in Example 8, the title compound was obtained as a colorless oil from methyl {6-[(4'-hydroxy-2'-methylbiphenyl-3-yl)methoxy]-2,3-dihydro-1-benzofuran-3-yl}acetate and 4-heptanol. yield 63%.
MS m/z 503 (MH$^+$).

EXAMPLE 60

(6-{[2'-methyl-4'-(1-propylbutoxy)biphenyl-3-yl]methoxy}-2,3-dihydro-1-benzofuran-3-yl)acetic acid

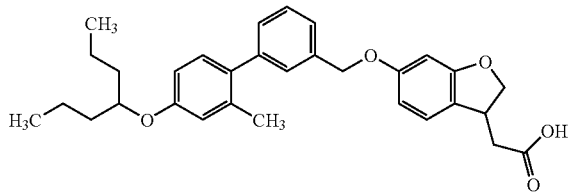

In the same manner as in Example 49, the title compound was obtained as colorless needle crystals from methyl (6-{[2'-methyl-4'-(1-propylbutoxy)biphenyl-3-yl]methoxy}-2,3-dihydro-1-benzofuran-3-yl)acetate. yield 82% (recrystallized from hexane-ethyl acetate).

MS m/z 489 (MH$^+$).

EXAMPLE 61 methyl (6-{[4'-(2-ethylbutoxy)-2'-methylbiphenyl-3-yl]methoxy}-2,3-dihydro-1-benzofuran-3-yl)acetate

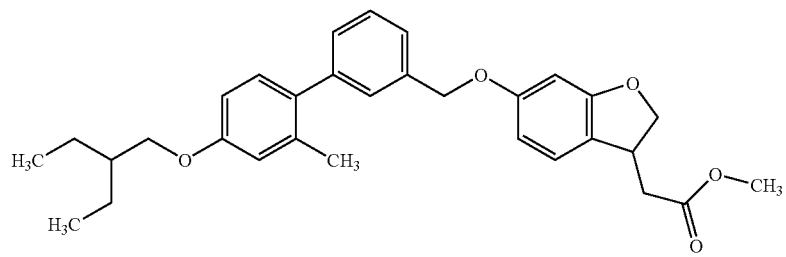

In the same manner as in Example 8, the title compound was obtained as a colorless oil from methyl {6-[(4'-hydroxy-2'-methylbiphenyl-3-yl)methoxy]-2,3-dihydro-1-benzofuran-3-yl}acetate and 2-ethyl-1-butanol. yield 37%.

MS m/z 489 (MH$^+$).

EXAMPLE 62

(6-{[4'-(2-ethylbutoxy)-2'-methylbiphenyl-3-yl]methoxy}-2,3-dihydro-1-benzofuran-3-yl)acetic acid

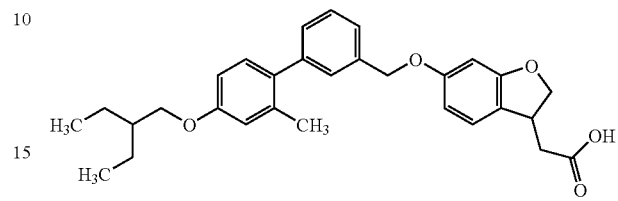

In the same manner as in Example 6, the title compound was obtained as colorless prism crystals from methyl (6-{[4'-(2-ethylbutoxy)-2'-methylbiphenyl-3-yl]methoxy}-2,3-dihydro-1-benzofuran-3-yl)acetate. yield 93% (recrystallized from hexane-ethyl acetate).

MS m/z 475 (MH$^+$).

EXAMPLE 63 methyl {6-[(4-{[(2-phenylethyl)(4-phenyl-1,3-thiazol-2-yl)amino]methyl}benzyl)oxy]-2,3-dihydro-1-benzofuran-3-yl}acetate

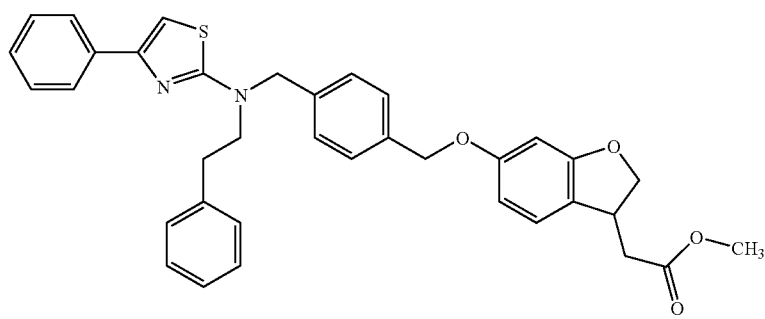

In the same manner as in Example 8, the title compound was obtained as a yellow oil from methyl (6-hydroxy-2,3-dihydro-1-benzofuran-3-yl)acetate and (4-{[(2-phenylethyl)(4-phenyl-1,3-thiazol-2-yl)amino]methyl}phenyl)methanol. yield 89%.

MS m/z 591 (MH+).

EXAMPLE 64

{6-[(4-{[(2-phenylethyl)(4-phenyl-1,3-thiazol-2-yl)amino]methyl}benzyl)oxy]-2,3-dihydro-1-benzofuran-3-yl}acetic acid

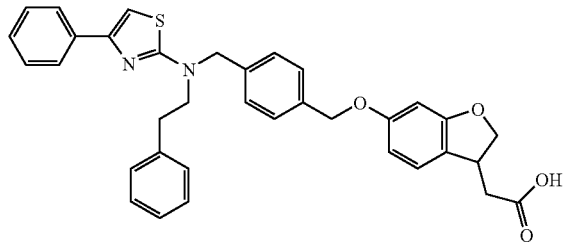

In the same manner as in Example 49, the title compound was obtained as a yellow viscous oil from methyl {6-[(4-{[(2-phenylethyl)(4-phenyl-1,3-thiazol-2-yl)amino]methyl}benzyl)oxy]-2,3-dihydro-1-benzofuran-3-yl}acetate. yield 97%.

MS m/z 577 (MH+).

EXAMPLE 65 methyl [6-({4-[(2-phenyl-1H-indol-1-yl)methyl]benzyl}oxy)-2,3-dihydro-1-benzofuran-3-yl]acetate

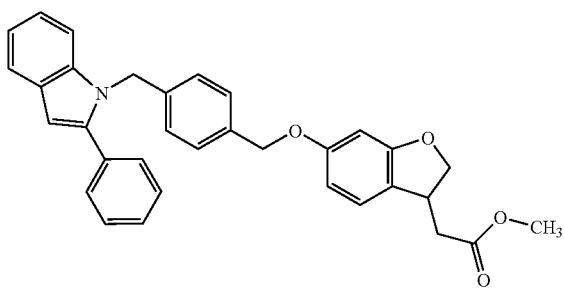

In the same manner as in Example 8, the title compound was obtained as a pale-yellow oil from methyl (6-hydroxy-2,3-dihydro-1-benzofuran-3-yl)acetate and {4-[(2-phenyl-1H-indol-1-yl)methyl]phenyl}methanol. yield 88%.

m/z 504 (MH+).

EXAMPLE 66

[6-({4-[(2-phenyl-1H-indol-1-yl)methyl]benzyl}oxy)-2,3-dihydro-1-benzofuran-3-yl]acetic acid

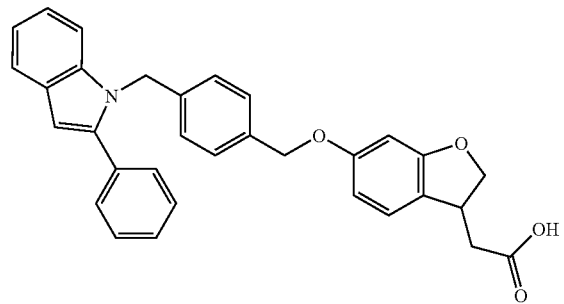

In the same manner as in Example 6, the title compound was obtained as pale-yellow prism crystals from methyl [6-({4-[(2-phenyl-1H-indol-1-yl)methyl]benzyl}oxy)-2,3-dihydro-1-benzofuran-3-yl]acetate. yield 81% (recrystallized from hexane-ethyl acetate).

MS m/z 490 (MH+).

EXAMPLE 67 methyl [6-({4-[(2-methyl-1H-indol-1-yl)methyl]benzyl}oxy)-2,3-dihydro-1-benzofuran-3-yl]acetate

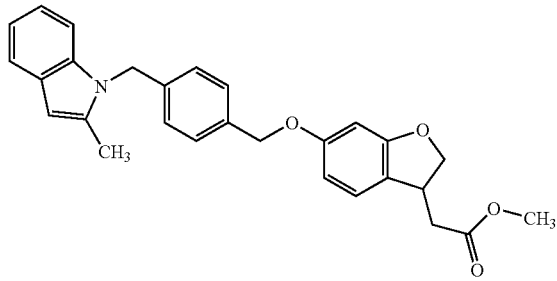

In the same manner as in Example 8, the title compound was obtained as a pale-yellow oil from methyl (6-hydroxy-2,3-dihydro-1-benzofuran-3-yl)acetate and {4-[(2-methyl-1H-indol-1-yl)methyl]phenyl}methanol. yield 95%.

MS m/z 442 (MH+).

EXAMPLE 68

[6-({4-[(2-methyl-1H-indol-1-yl)methyl]benzyl}oxy)-2,3-dihydro-1-benzofuran-3-yl]acetic acid

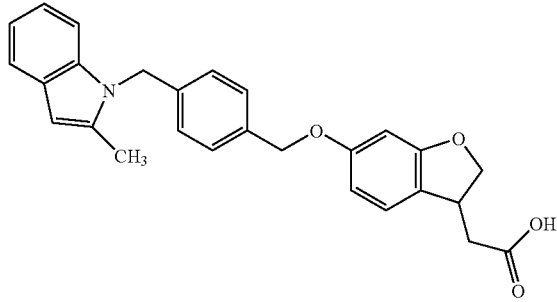

In the same manner as in Example 6, the title compound was obtained as a pale-red crystalline powder from methyl [6-({4-[(2-methyl-1H-indol-1-yl)methyl]benzyl}oxy)-2,3-dihydro-1-benzofuran-3-yl]acetate. yield 84% (recrystallized from hexane-ethyl acetate).

MS m/z 428 (MH+).

EXAMPLE 69 methyl (6-{[4'-(benzyloxy)-2',6'-dimethylbiphenyl-3-yl]methoxy}-2,3-dihydro-1-benzofuran-3-yl)acetate

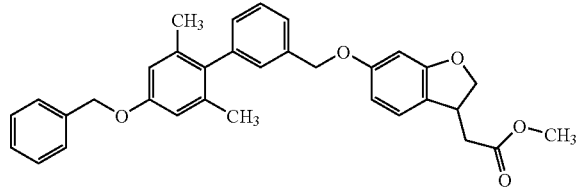

In the same manner as in Example 8, the title compound was obtained as a colorless oil from methyl (6-hydroxy-2,3-dihydro-1-benzofuran-3-yl)acetate and [4'-(benzyloxy)-2',6'-dimethylbiphenyl-3-yl]methanol. yield 93%.

MS m/z 509 (MH+).

EXAMPLE 70

(6-{[4'-(benzyloxy)-2',6'-dimethylbiphenyl-3-yl]methoxy}-2,3-dihydro-1-benzofuran-3-yl)acetic acid

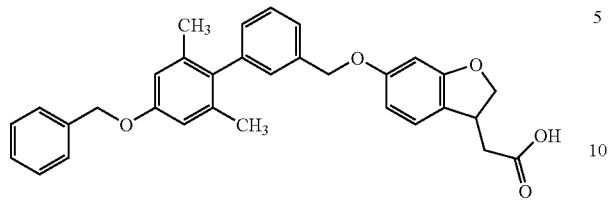

In the same manner as in Example 6, the title compound was obtained as colorless prism crystals from methyl (6-{[4'-(benzyloxy)-2',6'-dimethylbiphenyl-3-yl]methoxy}-2,3-dihydro-1-benzofuran-3-yl)acetate. yield 91% (recrystallized from hexane-ethyl acetate).
MS m/z 495 (MH$^+$).

EXAMPLE 71 methyl (6-{[4'-(2-ethoxyethoxy)-2',6'-dimethylbiphenyl-3-yl]methoxy}-2,3-dihydro-1-benzofuran-3-yl)acetate

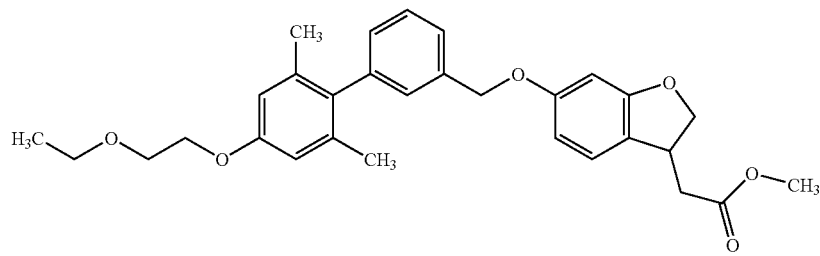

In the same manner as in Example 8, the title compound was obtained as a colorless oil from methyl (6-hydroxy-2,3-dihydro-1-benzofuran-3-yl)acetate and [4'-(2-ethoxyethoxy)-2',6'-dimethylbiphenyl-3-yl]methanol. yield 89%.
MS m/z 491 (MH$^+$).

EXAMPLE 72

(6-{[4'-(2-ethoxyethoxy)-2',6'-dimethylbiphenyl-3-yl]methoxy}-2,3-dihydro-1-benzofuran-3-yl)acetic acid

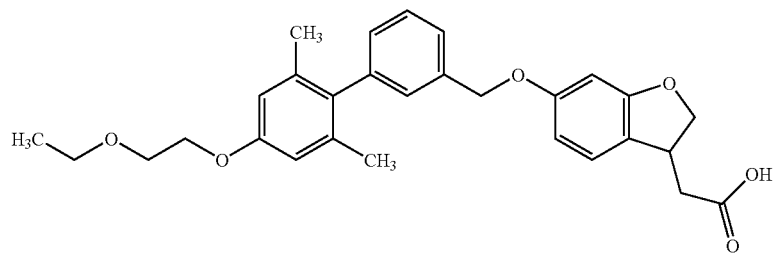

In the same manner as in Example 49, the title compound was obtained as colorless prism crystals from methyl (6-{[4'-(2-ethoxyethoxy)-2',6'-dimethylbiphenyl-3-yl]methoxy}-2,3-dihydro-1-benzofuran-3-yl)acetate. yield 68% (recrystallized from hexane-ethyl acetate).
MS m/z 477 (MH$^+$).

EXAMPLE 73 calcium {6-[(4-{[(2-phenylethyl)(4-phenyl-1,3-thiazol-2-yl)amino]methyl}benzyl)oxy]-2,3-dihydro-1-benzofuran-3-yl}acetate

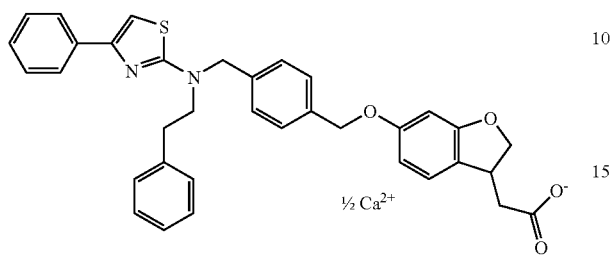

To a solution of {6-[(4-{[(2-phenylethyl)(4-phenyl-1,3-thiazol-2-yl)amino]methyl}benzyl)oxy]-2,3-dihydro-1-benzofuran-3-yl}acetic acid (0.541 g, 0.938 mmol) in methanol (5 mL) was added 2 M aqueous sodium hydroxide solution (1 mL), and the mixture was concentrated under reduced pressure. Water (50 mL) and methanol (20 mL) were added to the obtained residue, and a solution of calcium chloride (0.111 g, 1.00 mmol) in water (5 mL) was added thereto. The mixture was concentrated under reduced pressure, and the precipitated solid was collected by filtration and washed with water to give the title compound (0.454 g, yield 81%) as a pale-yellow amorphous solid.

$^1$H NMR (DMSO-$d_6$) δ: 2.16(1H, dd, J=15.5, 9.3 Hz), 2.43(1H, dd, J=15.5, 5.6 Hz), 2.90-3.00(2H, m), 3.58-3.73 (3H, m), 4.10-4.19(1H, m), 4.62-4.73(3H, m), 4.97(2H, s), 6.36-6.42(2H, m), 7.09(1H, d, J=8.7 Hz), 7.17-7.42(13H, m), 7.87(1H, d, J=7.3 Hz).

EXAMPLE 74 methyl (6-{[6-(benzyloxy)-2',6'-dimethylbiphenyl-3-yl]methoxy}-2,3-dihydro-1-benzofuran-3-yl)acetate

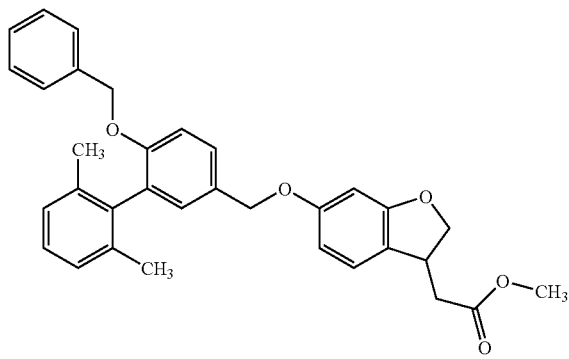

In the same manner as in Example 8, the title compound was obtained as a colorless oil from methyl (6-hydroxy-2,3-dihydro-1-benzofuran-3-yl)acetate and [6-(benzyloxy)-2',6'-dimethyl-3-biphenylyl]methanol. yield 50%.

MS m/z 509 (MH$^+$).

EXAMPLE 75

(6-{[6-(benzyloxy)-2',6'-dimethylbiphenyl-3-yl]methoxy}-2,3-dihydro-1-benzofuran-3-yl)acetic acid

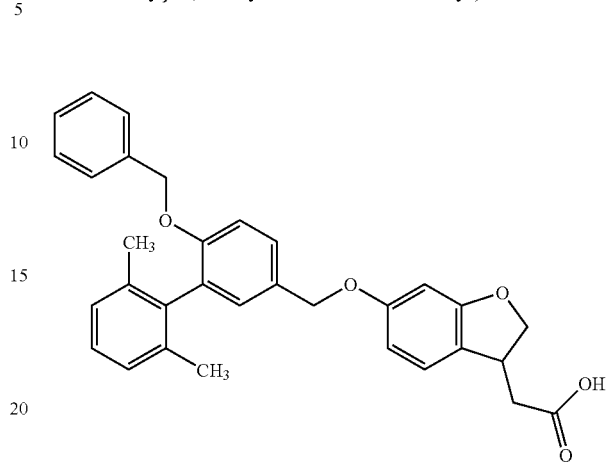

In the same manner as in Example 49, the title compound was obtained as colorless prism crystals from methyl (6-{[6-(benzyloxy)-2',6'-dimethylbiphenyl-3-yl]methoxy}-2,3-dihydro-1-benzofuran-3-yl)acetate. yield 76% (recrystallized from heptane-ethyl acetate).

MS m/z 495 (MH$^+$).

EXAMPLE 76 ethyl {5-[(2',6'-dimethylbiphenyl-3-yl)methoxy]-1H-indol-1-yl}acetate

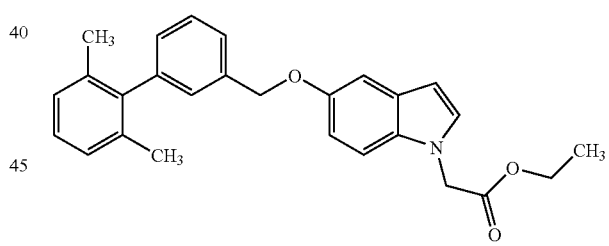

5-[(2',6'-Dimethylbiphenyl-3-yl)methoxy]-1H-indole (0.95 g, 2.90 mmol) was dissolved in a mixed solvent of tetrahydrofuran (30 mL) and N,N-dimethylformamide (4 mL). The solution was ice-cooled, and sodium hydride (60% in oil, 0.12 g, 3.0 mmol) was added, and the mixture was stirred at the same temperature for 20 min. Then, ethyl bromoacetate (0.36 mL, 3.25 mmol) was added to the solution, and the mixture was allowed to warm to room temperature and stirred for 2 days. The reaction solution was diluted with ethyl acetate, washed successively with aqueous citric acid solution, water and brine, dried over magnesium sulfate and concentrated under reduced pressure. The residue was purified by silica gel column chromatography (ethyl acetate:hexane=1:10-1:5) to give the title compound (1.0 g, yield 83%) as a pale-yellow oil.

MS m/z 414 (MH$^+$).

EXAMPLE 77

{5-[(2',6'-dimethylbiphenyl-3-yl)methoxy]-1H-indol-1-yl}acetic acid

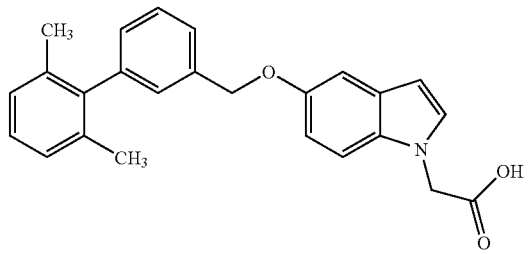

To a solution of ethyl {5-[(2',6'-dimethylbiphenyl-3-yl)methoxy]-1H-indol-1-yl}acetate (0.27 g, 0.65 mmol) in a mixed solvent of methanol (10 mL) and tetrahydrofuran (10 mL) was added 85% aqueous solution (5 mL) of potassium hydroxide (0.13 g, 1.97 mmol), and the mixture was stirred at room temperature for 18 hr. Water was added to the reaction mixture, and the mixture was made weak acidic with 10% aqueous citric acid solution and extracted with ethyl acetate. The extract was washed with saturated brine, dried over anhydrous sodium sulfate and concentrated under reduced pressure. The residue was purified by silica gel column chromatography (ethyl acetate:hexane=1:2-2:1) to give the title compound (0.19 g, yield 76%) as a pale-yellow amorphous solid.

MS m/z 386 (MH$^+$).

EXAMPLE 78

{2-[(3-phenoxybenzyl)thio]-4,5,6,7-tetrahydro-1,3-benzothiazol-7-yl}acetic acid

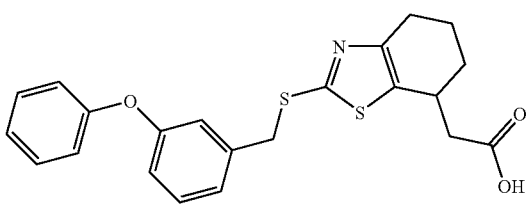

A mixture of diethyl {2-[(3-phenoxybenzyl)thio]-4,5,6,7-tetrahydro-1,3-benzothiazol-7-yl}malonate (1.21 g, 2.36 mmol), 37% hydrochloric acid (10 mL) and acetic acid (10 mL) was heated with stirring at 120° C. for 12 hr. The reaction mixture was concentrated, and the residue was diluted with ethyl acetate, washed successively with 10% aqueous sodium hydrogen carbonate solution and saturated brine, dried over anhydrous magnesium sulfate and concentrated under reduced pressure to give the title compound (890 mg, 92%) as a pale-yellow oil.

$^1$H NMR (CDCl$_3$) δ: 1.53-2.13(6H, m), 2.47-2.77(2H, m), 3.33-3.42(1H, m), 4.31(2H, s), 6.90(1H, dd, J=7.7, 2.1 Hz), 6.96-7.02(3H, m), 7.06-7.14(2H, m), 7.21-7.37(3H, m).

EXAMPLE 79 methyl [6-({2-methyl-5-[4-(trifluoromethyl)phenyl]-3-furyl}methoxy)-2,3-dihydro-1-benzofuran-3-yl]acetate

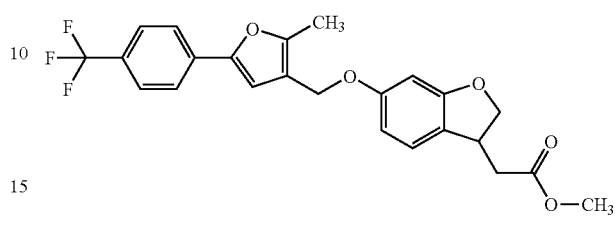

In the same manner as in Example 8, the title compound was obtained as colorless prism crystals from methyl (6-hydroxy-2,3-dihydro-1-benzofuran-3-yl)acetate and {2-methyl-5-[4-(trifluoromethyl)phenyl]-3-furyl}methanol. yield 84% (recrystallized from hexane-ethyl acetate).

melting point: 131-132° C.

EXAMPLE 80

[6-({2-methyl-5-[4-(trifluoromethyl)phenyl]-3-furyl}methoxy)-2,3-dihydro-1-benzofuran-3-yl]acetic acid

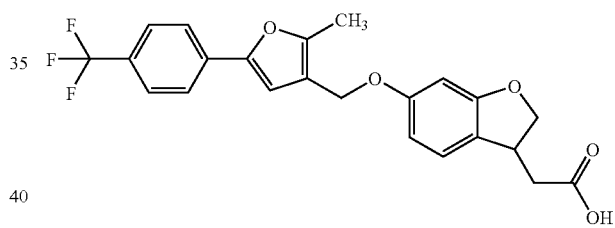

In the same manner as in Example 6, the title compound was obtained as colorless prism crystals from methyl [6-({2-methyl-5-[4-(trifluoromethyl)phenyl]-3-furyl}methoxy)-2,3-dihydro-1-benzofuran-3-yl]acetate. yield 95% (recrystallized from hexane-ethyl acetate).

melting point: 180-181° C.

EXAMPLE 81 methyl {6-[(2-phenyl-1,3-thiazol-4-yl)methoxy]-2,3-dihydro-1-benzofuran-3-yl}acetate

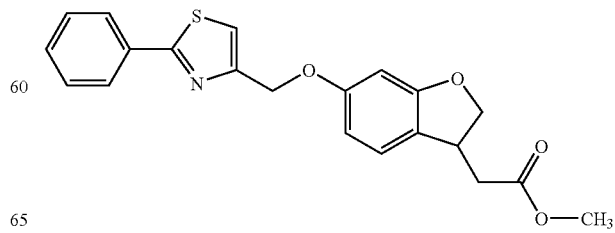

Methyl (6-hydroxy-2,3-dihydro-1-benzofuran-3-yl)acetate (200 mg, 0.961 mmol) and 4-(chloromethyl)-2-phenyl-1,3-thiazole (240 mg, 1.14 mmol) were dissolved in N,N-dimethylformamide (5 mL), and potassium carbonate (160 mg, 1.16 mmol) was added, and the mixture was stirred at 60-70° C. for 3 hr. Water was added to the reaction mixture, and the mixture was neutralized with 2 M hydrochloric acid. The precipitated crystals were recrystallized from ethyl acetate-diisopropyl ether to give the title compound (270 mg, yield 74%) as colorless prism crystals.

melting point: 116-117° C.

EXAMPLE 82

{6-[(2-phenyl-1,3-thiazol-4-yl)methoxy]-2,3-dihydro-1-benzofuran-3-yl}acetic acid

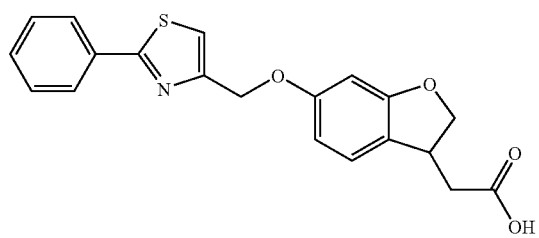

In the same manner as in Example 6, the title compound was obtained as colorless needle crystals from methyl {6-[(2-phenyl-1,3-thiazol-4-yl)methoxy]-2,3-dihydro-1-benzofuran-3-yl}acetate. yield 98% (recrystallized from ethyl acetate-methanol).

melting point: 169-170° C.

EXAMPLE 83 methyl {6-[(2-pyrazin-2-yl-1,3-thiazol-4-yl)methoxy]-2,3-dihydro-1-benzofuran-3-yl}acetate

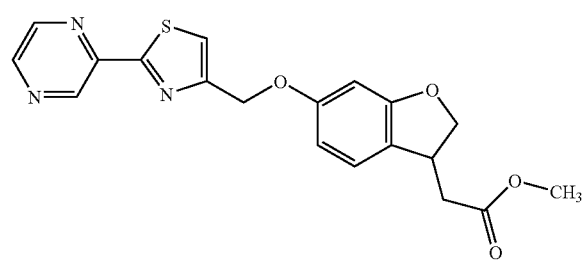

In the same manner as in Example 8, the title compound was obtained as colorless crystals from methyl (6-hydroxy-2,3-dihydro-1-benzofuran-3-yl)acetate and (2-pyrazin-2-yl-1,3-thiazol-4-yl)methanol. yield 35%.

MS m/z 384 (MH$^+$).

EXAMPLE 84

{6-[(2-pyrazin-2-yl-1,3-thiazol-4-yl)methoxy]-2,3-dihydro-1-benzofuran-3-yl}acetic acid

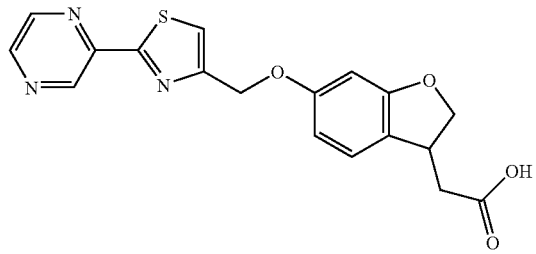

In the same manner as in Example 6, the title compound was obtained as colorless needle crystals from methyl {6-[(2-pyrazin-2-yl-1,3-thiazol-4-yl)methoxy]-2,3-dihydro-1-benzofuran-3-yl}acetate. yield 87% (recrystallized from ethyl acetate).

MS m/z 370 (MH$^+$).

EXAMPLE 85 methyl {6-[3-(2-phenyl-1H-indol-1-yl)propoxy]-2,3-dihydro-1-benzofuran-3-yl}acetate

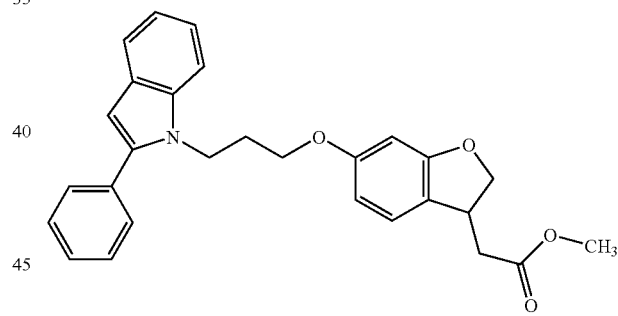

To a solution of 2-phenyl-1H-indole (0.425 g, 2.20 mmol) in N,N-dimethylformamide (2 mL) was added sodium hydride (60% in oil, 88 mg, 2.20 mmol), and the mixture was stirred at room temperature for 30 min. A solution of sodium iodide (0.330 g, 2.20 mmol) and methyl [6-(3-chloropropoxy)-2,3-dihydro-1-benzofuran-3-yl]acetate (0.589 g, 2.07 mmol) in N,N-dimethylformamide (3 mL) was added to the reaction mixture, and the mixture was stirred at room temperature for 18 hr. Water and saturated aqueous ammonium chloride solution were added to the reaction mixture, and the mixture was extracted with ethyl acetate. The extract was washed with saturated brine, dried over anhydrous magnesium sulfate and concentrated under reduced pressure. The residue was purified by silica gel column chromatography (10%-40% ethyl acetate/hexane) to give the title compound (0.160 g, yield 18%) as a colorless oil.

MS m/z 442 (MH$^+$).

EXAMPLE 86

{6-[3-(2-phenyl-1H-indol-1-yl)propoxy]-2,3-dihydro-1-benzofuran-yl}acetic acid

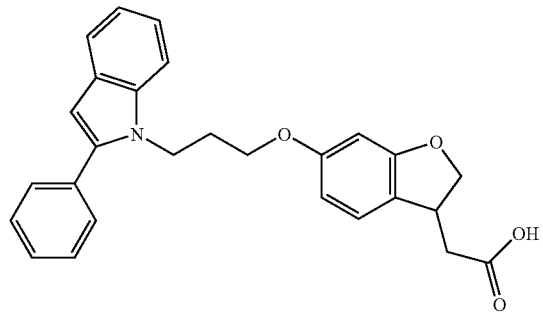

In the same manner as in Example 6, the title compound was obtained as colorless prism crystals from methyl {6-[3-(2-phenyl-1H-indol-1-yl)propoxy]-2,3-dihydro-1-benzofuran-3-yl}acetate. yield 83% (recrystallized from hexane-ethyl acetate).

MS m/z 428 (MH$^+$).

The compounds described in Examples 87-95 and Examples 97-118 were synthesized in the same manner as in Example 96.

EXAMPLE 87

(6-{[4-(2-benzoyl-4-chlorophenyl)-4H-1,2,4-triazol-3-yl]methoxy}-2,3-dihydro-1-benzofuran-3-yl)acetic acid

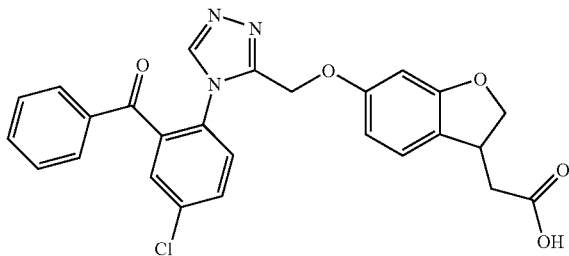

yield 43%. MS (ESI+, m/e) 490 (M+1).

EXAMPLE 88

(6-{2-[cyclohexyl(2-nitrobenzyl)amino]ethoxy}-2,3-dihydro-1-benzofuran-3-yl)acetic acid trifluoroacetate

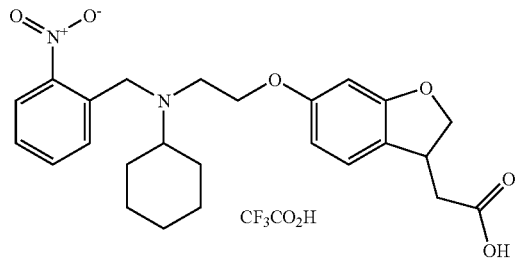

yield 24%. MS (ESI+, m/e) 455 (M+1).

EXAMPLE 89

{6-[4-(imidazo[1,2-a]pyridin-8-yloxy)butoxy]-2,3-dihydro-1-benzofuran-3-yl}acetic acid trifluoroacetate

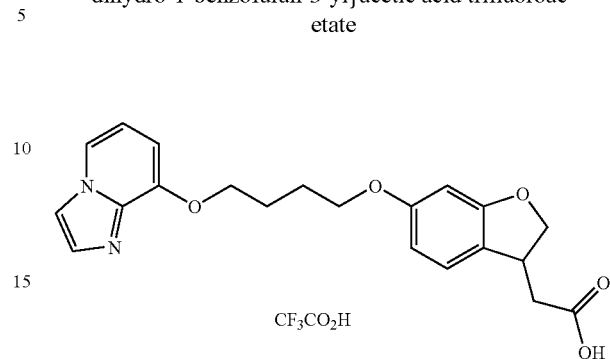

yield 2%. MS (ESI+, m/e) 383 (M+1).

EXAMPLE 90

(6-{[3-benzyl-2-(2-thienyl)-3H-thieno[2,3-d]imidazol-5-yl]methoxy}-2,3-dihydro-1-benzofuran-3-yl)acetic acid

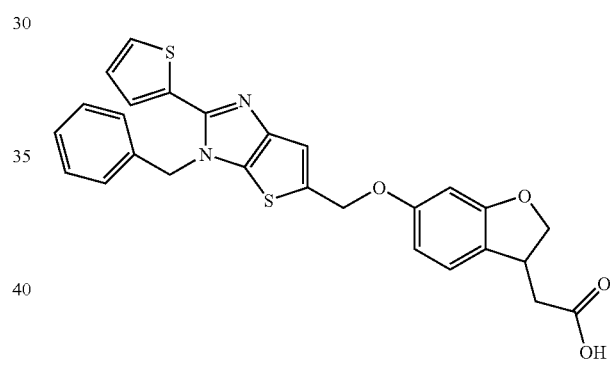

yield 16%. MS (ESI+, m/e) 503 (M+1).

EXAMPLE 91

(6-{[1-benzyl-2-phenyl-4-(phenylthio)-1H-imidazol-5-yl]methoxy}-2,3-dihydro-1-benzofuran-3-yl)acetic acid

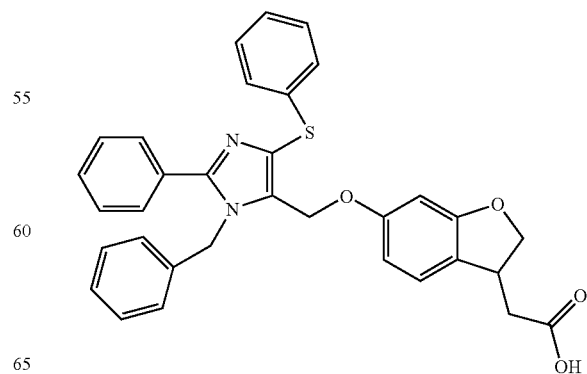

yield 29%. MS (ESI+, m/e) 549 (M+1).

EXAMPLE 92

(6-{[2-(5-methyl-2-furyl)-1,3-oxazol-4-yl]methoxy}-2,3-dihydro-1-benzofuran-3-yl)acetic acid

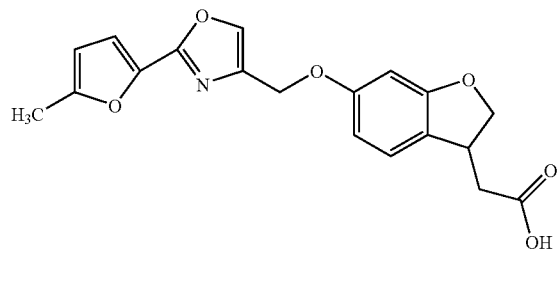

yield 67%. MS (ESI+, m/e) 356 (M+1).

EXAMPLE 93

(6-{[2-(3-furyl)-1,3-oxazol-4-yl]methoxy}-2,3-dihydro-1-benzofuran-3-yl)acetic acid

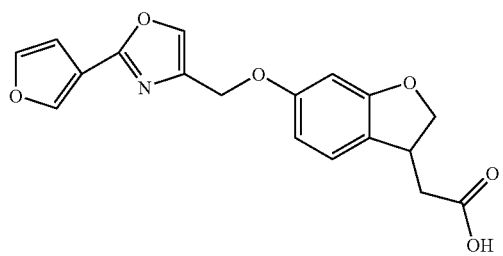

yield 55%. MS (ESI+, m/e) 342 (M+1).

EXAMPLE 94

(6-{[3-(2-thienyl)-1,2,4-oxadiazol-5-yl]methoxy}-2,3-dihydro-1-benzofuran-3-yl)acetic acid

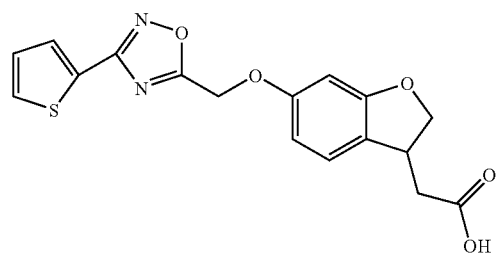

yield 48%. MS (ESI+, m/e) 359 (M+1).

EXAMPLE 95

{6-[(5-oxo-2-phenyl-4,5-dihydropyrazolo[1,5-a]pyrimidin-7-yl)methoxy]-2,3-dihydro-1-benzofuran-3-yl}acetic acid

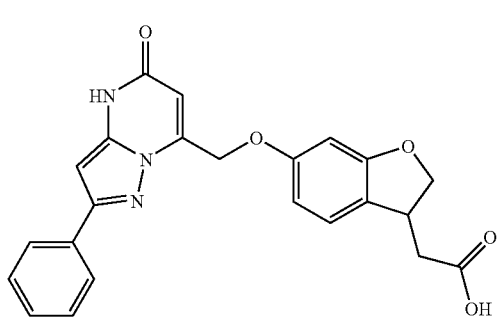

yield 3%. MS (ESI+, m/e) 418 (M+1).

EXAMPLE 96

[6-({4-[(dibenzylamino)carbonyl]benzyl}oxy)-2,3-dihydro-1-benzofuran-3-yl]acetic acid

[Step 1]
To a solution of methyl (6-hydroxy-2,3-dihydro-1-benzofuran-3-yl)acetate (30 mg, 0.14 mmol) in DMF (1 mL) were added a solution of N,N-dibenzyl-4-(chloromethyl)benzamide (63 mg, 0.18 mmol) in DMF (0.5 mL) and potassium carbonate (29 mg, 0.21 mmol), and the mixture was stirred at 70° C. for 20 hr. Water (2 mL) was added to the reaction mixture, and the mixture was extracted with dichloromethane (2 mL). The organic layer was concentrated under reduced pressure using GeneVac centrifugal evaporator.

[Step 2]
The obtained product was dissolved in methanol (2 mL), and 1 M aqueous sodium hydroxide solution (0.25 mL, 0.25 mmol) was added, and the mixture was stirred at room temperature for 18 hr. The reaction mixture was acidified with 1 M hydrochloric acid and extracted with dichloromethane (2 mL). The organic layer was concentrated under reduced pressure using GeneVac centrifugal evaporator. The residue was purified by preparative HPLC to give the title compound (48.8 mg, yield 68%).

$^1$H NMR (DMSO-d$_6$) δ: 2.46(1H, dd, J=9.0, 16.5 Hz), 2.68(1H, dd, J=5.4, 16.5 Hz), 3.62-3.72(1H, m), 4.18(1H, dd, J=6.9, 9.0 Hz), 4.41(2H, br), 4.58(2H, br), 4.68(1H, t, J=9.0 Hz), 5.06(2H, s), 6.44-6.48(2H, m), 7.10(1H, d, J=7.5 Hz), 7.16-7.36(10H, m), 7.48(4H, s).

EXAMPLE 97

[6-({4-[(4-phenyl-1-piperazinyl)carbonyl] benzyl}oxy)-2,3-dihydro-1-benzofuran-3-yl]acetic acid trifluoroacetate

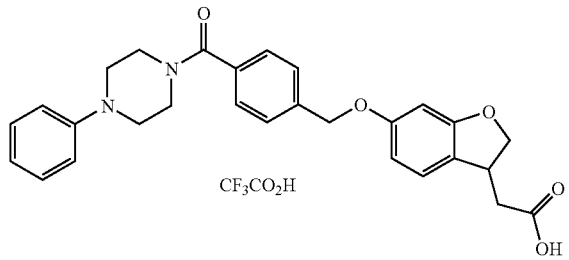

yield 30%. MS (ESI+, m/e) 473 (M+1).

EXAMPLE 98

(6-{2-[4-(diphenylmethyl)-1-piperazinyl]ethoxy}-2, 3-dihydro-1-benzofuran-3-yl)acetic acid 2 trifluoroacetate

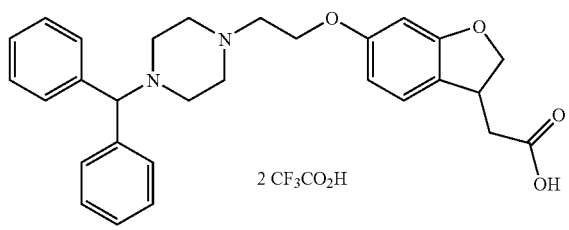

yield 79%. MS (ESI+, m/e) 473 (M+1).

EXAMPLE 99

{6-[(3'-fluoro-4-biphenylyl)methoxy]-2,3-dihydro-1-benzofuran-3-yl}acetic acid

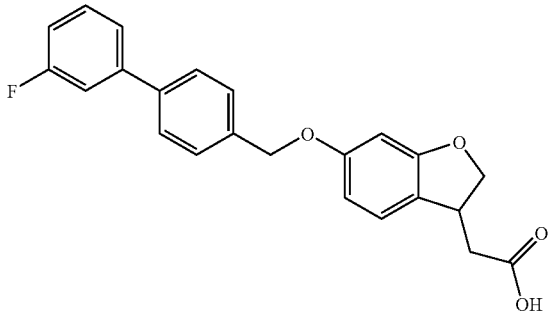

yield 48%. MS (ESI+, m/e) 379 (M+1).

EXAMPLE 100

(6-{[8-(benzyloxy)imidazo[1,2-a]pyridin-2-yl]methoxy}-2,3-dihydro-1-benzofuran-3-yl)acetic acid trifluoroacetate

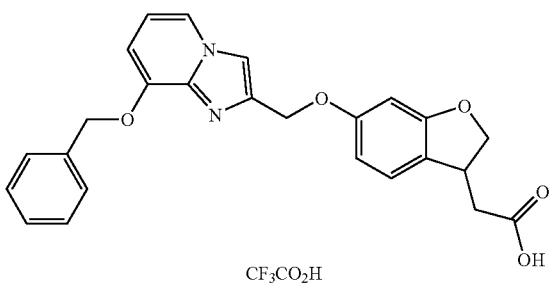

yield 23%. MS (ESI+, m/e) 431 (MH$^+$).

EXAMPLE 101

(6-{3-[(4'-cyano-4-biphenylyl)oxy]propoxy}-2,3-dihydro-1-benzofuran-3-yl)acetic acid

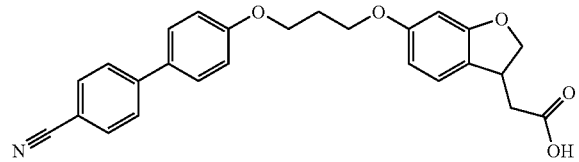

yield 37%. MS (ESI+, m/e) 430 (M+1).

EXAMPLE 102

4-[4-(3-{[3-(carboxymethyl)-2,3-dihydro-1-benzofuran-6-yl]oxy}propoxy)phenoxy]benzoic acid

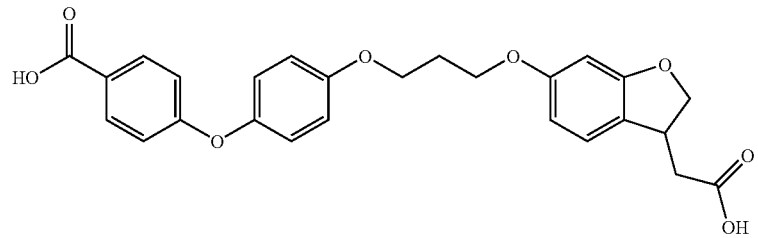

yield 9%. MS (ESI+, m/e) 465 (M+1).

EXAMPLE 103

[6-(3-{4-[(7-oxo-3-azepanyl)methyl]phenoxy}propoxy)-2,3-dihydro-1-benzofuran-3-yl]acetic acid

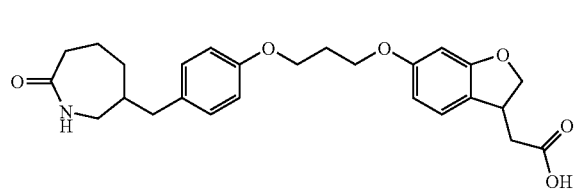

yield 48%. MS (ESI+, m/e) 454 (M+1).

EXAMPLE 104

(6-{[4-(1H-pyrazol-1-yl)benzyl]oxy}-2,3-dihydro-1-benzofuran-3-yl)acetic acid

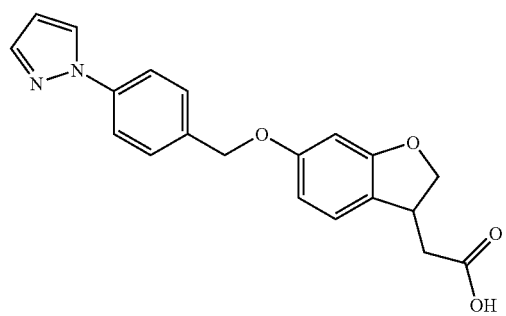

yield 60%. MS (ESI+, m/e) 351 (M+1).

EXAMPLE 105

(6-{[4-(1H-imidazol-1-yl)benzyl]oxy}-2,3-dihydro-1-benzofuran-3-yl)acetic acid trifluoroacetate

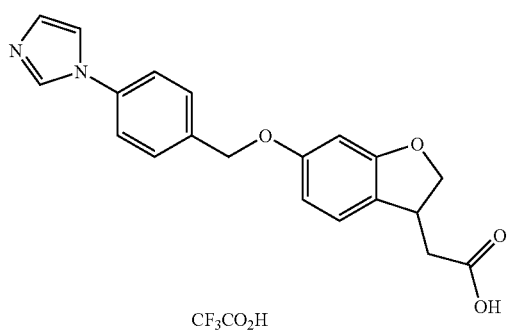

yield 12%. MS (ESI+, m/e) 351 (M+1).

EXAMPLE 106

(6-{[4-(1,3-oxazol-5-yl)benzyl]oxy}-2,3-dihydro-1-benzofuran-3-yl)acetic acid

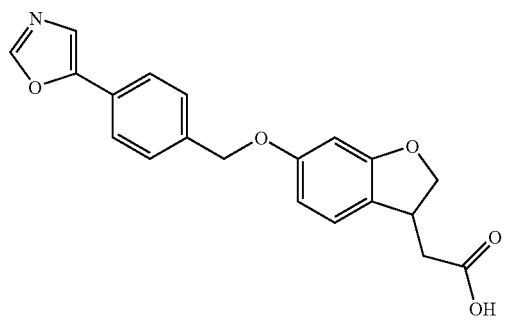

yield 10%. MS (ESI+, m/e) 352 (M+1).

EXAMPLE 107

(6-{[4-(1H-1,2,4-triazol-1-yl)benzyl]oxy}-2,3-dihydro-1-benzofuran-3-yl)acetic acid

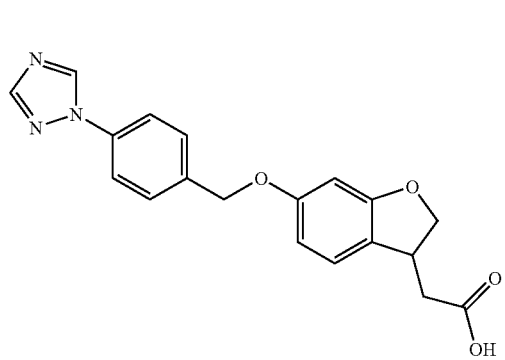

yield 13%. MS (ESI+, m/e) 352 (M+1).

EXAMPLE 108

[6-({3,5-dimethoxy-4-[(5-methyl-2-phenyl-1,3-oxazol-4-yl)methoxy]benzyl}oxy)-2,3-dihydro-1-benzofuran-3-yl]acetic acid

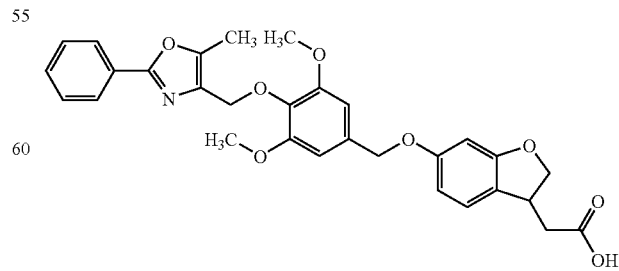

yield 59%. MS (ESI+, m/e) 532 (M+1).

EXAMPLE 109

{6-[(5-phenylpentyl)oxy]-2,3-dihydro-1-benzofuran-3-yl}acetic acid

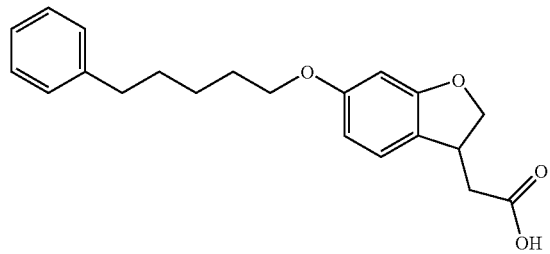

yield 65%. MS (ESI+, m/e) 341 (M+1).

EXAMPLE 110

(6-{3-[4-(3-chlorophenyl)-1-piperazinyl]propoxy}-2,3-dihydro-1-benzofuran-3-yl)acetic acid 2 trifluoroacetate

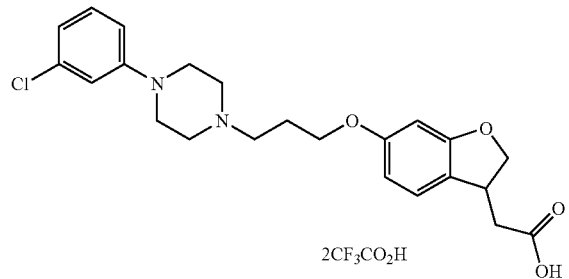

yield 30%. MS (ESI+, m/e) 431 (M+1).

EXAMPLE 111

{6-[(1-benzyl-1H-imidazol-2-yl)methoxy]-2,3-dihydro-1-benzofuran-3-yl}acetic acid

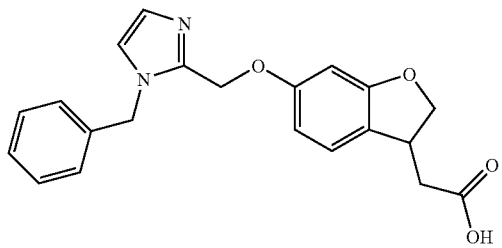

yield 25%. MS (ESI+, m/e) 365 (M+1).

EXAMPLE 112

(6-{[5-(2-methoxyphenyl)-1,2,4-oxadiazol-3-yl]methoxy}-2,3-dihydro-1-benzofuran-3-yl)acetic acid

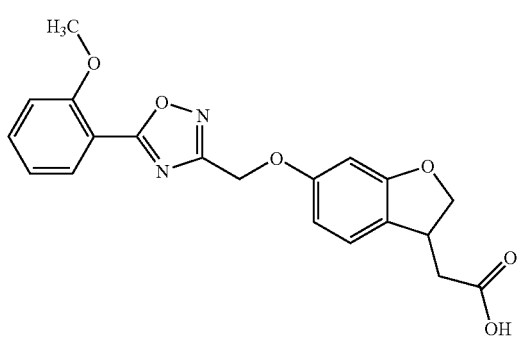

yield 69%. MS (ESI+, m/e) 383 (M+1).

EXAMPLE 113

(6-{[5-(4-methoxyphenyl)-1,2,4-oxadiazol-3-yl]methoxy}-2,3-dihydro-1-benzofuran-3-yl)acetic acid

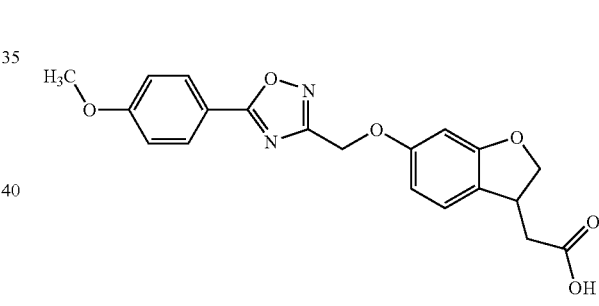

yield 50%. MS (ESI+, m/e) 383 (M+1).

EXAMPLE 114

{6-[(5-phenyl-1,2,4-oxadiazol-3-yl)methoxy]-2,3-dihydro-1-benzofuran-3-yl}acetic acid

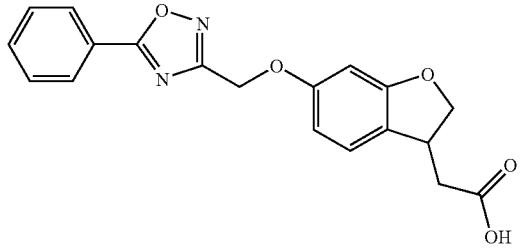

yield 67%. MS (ESI+, m/e) 353 (M+1).

EXAMPLE 115

[6-(3-phenoxypropoxy)-2,3-dihydro-1-benzofuran-3-yl]acetic acid

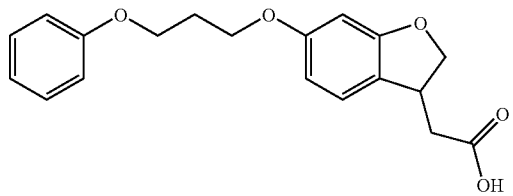

yield 23%. MS (ESI+, m/e) 329 (M+1).

EXAMPLE 116

(6-{[2-(4-chlorophenyl)-1,3-thiazol-4-yl]methoxy}-2,3-dihydro-1-benzofuran-3-yl)acetic acid

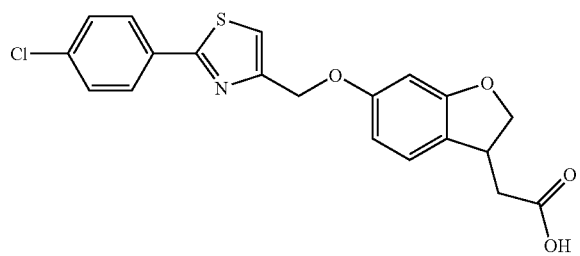

yield 50%. MS (ESI+, m/e) 402 (M+1).

EXAMPLE 117

[6-(4-phenoxybutoxy)-2,3-dihydro-1-benzofuran-3-yl]acetic acid

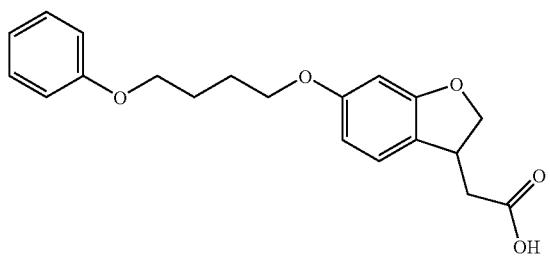

yield 37%. MS (ESI+, m/e) 343 (M+1).

EXAMPLE 118

(6-{2-oxo-2-[4-(1-pyrrolidinyl)phenyl]ethoxy}-2,3-dihydro-1-benzofuran-3-yl)acetic acid trifluoroacetate

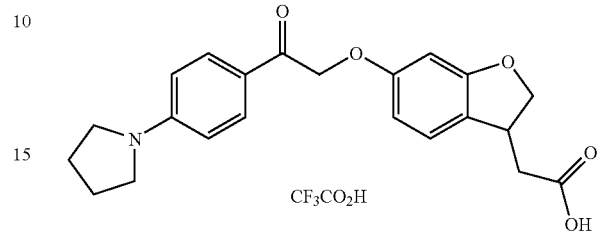

yield 36%. MS (ESI+, m/e) 382 (M+1).

The compounds described in Examples 119-140 and Examples 142-152 were synthesized in the same manner as in Example 141.

EXAMPLE 119

{6-[(4-butoxybenzyl)oxy]-2,3-dihydro-1-benzofuran-3-yl}acetic acid

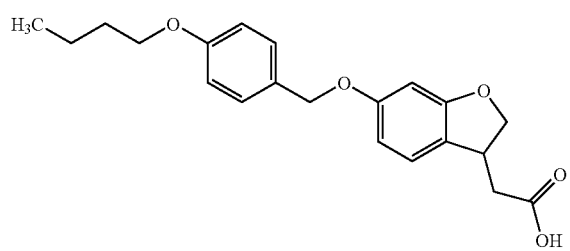

yield 17%. MS (ESI+, m/e) 357 (M+1).

EXAMPLE 120

(6-{2-[[4-(methoxycarbonyl)phenyl](methyl)amino]ethoxy}-2,3-dihydro-1-benzofuran-3-yl)acetic acid trifluoroacetate

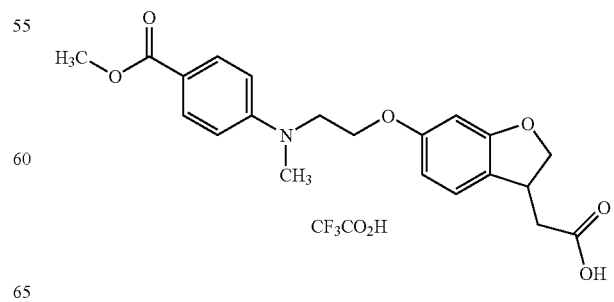

yield 23%. MS (ESI+, m/e) 386 (M+1).

EXAMPLE 121

(6-{2-[(6-methoxy-2-phenyl-4-pyrimidinyl)thio] ethoxy}-2,3-dihydro-1-benzofuran-3-yl)acetic acid

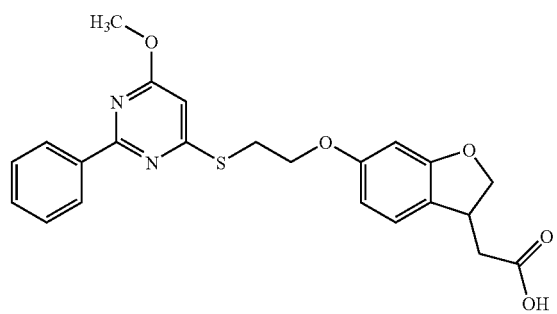

yield 3%. MS (ESI+, m/e) 439 (M+1).

EXAMPLE 122

[6-(2-{5-[(4-pyridinylmethyl)thio]-1H-tetrazol-1-yl}ethoxy)-2,3-dihydro-1-benzofuran-3-yl]acetic acid trifluoroacetate

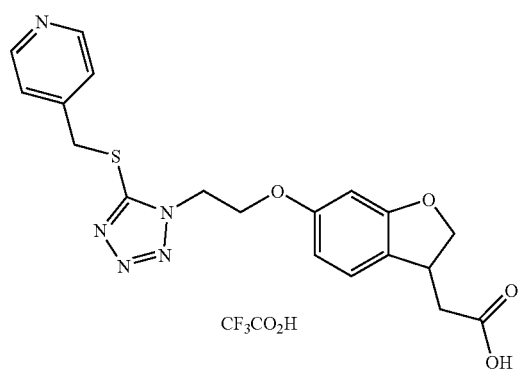

yield 3%. MS (ESI+, m/e) 414 (M+1).

EXAMPLE 123

(6-{[3-(4-acetylphenyl)-2-oxo-1,3-oxazolidin-5-yl]methoxy}-2,3-dihydro-1-benzofuran-3-yl)acetic acid

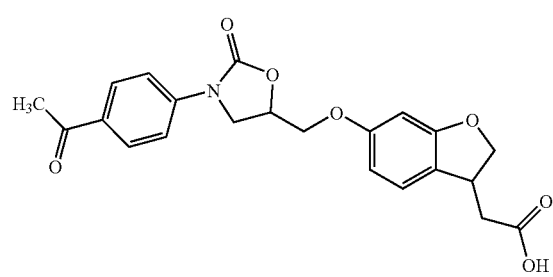

yield 42%. MS (ESI+, m/e) 412 (M+1).

EXAMPLE 124

(6-{[3-methyl-4-(2,2,2-trifluoroethoxy)-2-pyridinyl]methoxy}-2,3-dihydro-1-benzofuran-3-yl)acetic acid trifluoroacetate

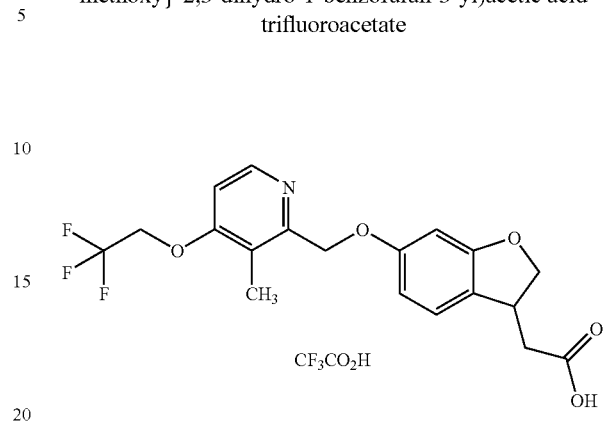

yield 29%. MS (ESI+, m/e) 398 (M+1).

EXAMPLE 125

(6-{[(2E)-3-(5,6,7,8-tetrahydro-2-naphthalenyl)-2-buten-1-yl]oxy}-2,3-dihydro-1-benzofuran-3-yl)acetic acid

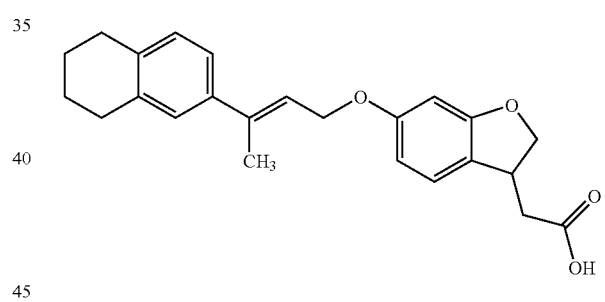

yield 43%. MS (ESI+, m/e) 379 (M+1).

EXAMPLE 126

{6-[3-(4-cyclohexylphenoxy)propoxy]-2,3-dihydro-1-benzofuran-3-yl}acetic acid

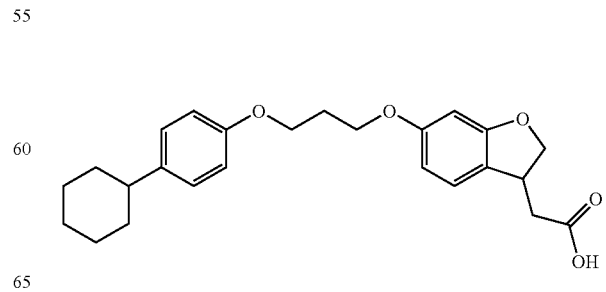

yield 5%. MS (ESI+, m/e) 411 (M+1).

EXAMPLE 127

(6-{[4-(1H-1,2,3-triazol-1-yl)benzyl]oxy}-2,3-dihydro-1-benzofuran-3-yl)acetic acid

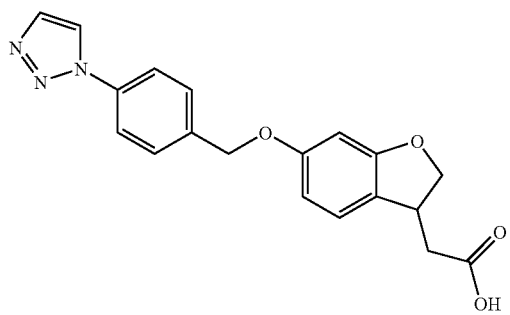

yield 64%. MS (ESI+, m/e) 352 (M+1).

EXAMPLE 128

{6-[(5-phenyl-1H-pyrazol-3-yl)methoxy]-2,3-dihydro-1-benzofuran-3-yl}acetic acid

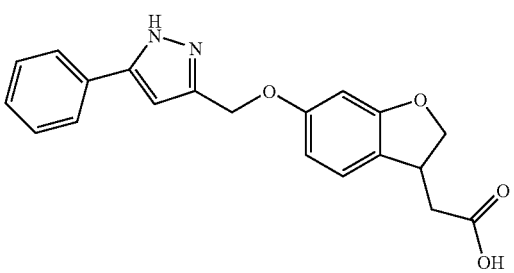

yield 7%. MS (ESI+, m/e) 351 (M+1).

EXAMPLE 129

(6-{[5-(4-fluorophenyl)-1-methyl-1H-pyrazol-3-yl]methoxy}-2,3-dihydro-1-benzofuran-3-yl)acetic acid

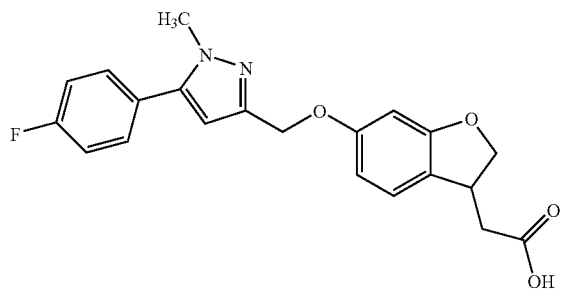

yield 43%. MS (ESI+, m/e) 383 (M+1).

EXAMPLE 130

(6-{[3-(4-fluorophenyl)-1-methyl-1H-pyrazol-5-yl]methoxy}-2,3-dihydro-1-benzofuran-3-yl)acetic acid

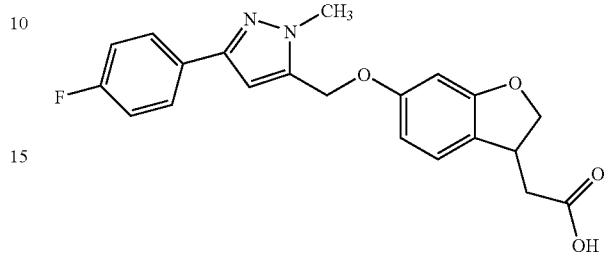

yield 13%. MS (ESI+, m/e) 383 (M+1).

EXAMPLE 131

{6-[(4-phenyl-1,3-thiazol-2-yl)methoxy]-2,3-dihydro-1-benzofuran-3-yl}acetic acid

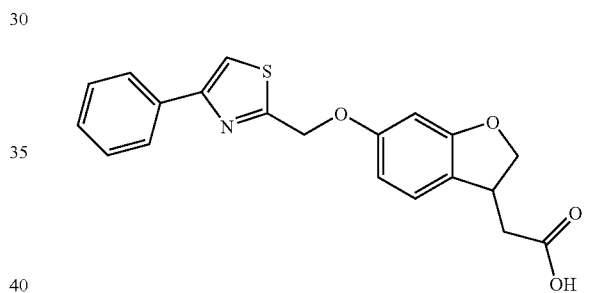

yield 37%. MS (ESI+, m/e) 368 (M+1).

EXAMPLE 132

(6-{[2-(4-pyridinyl)-1,3-thiazol-4-yl]methoxy}-2,3-dihydro-1-benzofuran-3-yl)acetic acid

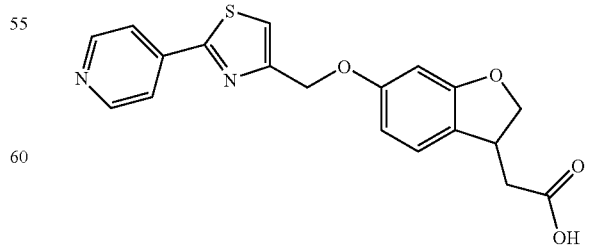

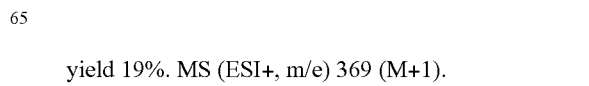

yield 19%. MS (ESI+, m/e) 369 (M+1).

EXAMPLE 133

(6-{[2-(2-furyl)-1,3-thiazol-4-yl]methoxy}-2,3-dihydro-1-benzofuran-3-yl)acetic acid

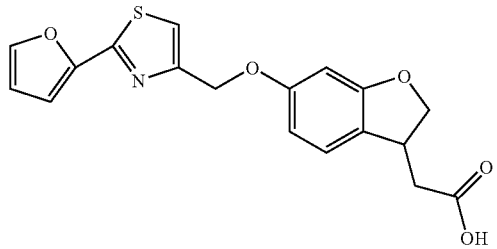

yield 16%. MS (ESI+, m/e) 358 (M+1).

EXAMPLE 134

(6-{[2-(2-thienyl)-1,3-thiazol-4-yl]methoxy}-2,3-dihydro-1-benzofuran-3-yl)acetic acid

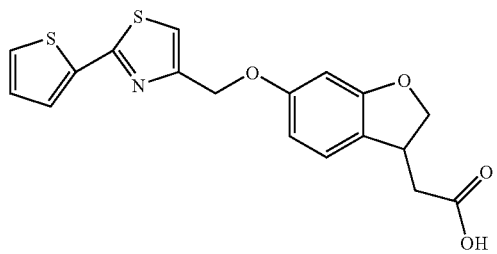

yield 45%. MS (ESI+, m/e) 374 (M+1).

EXAMPLE 135

{6-[(4-chloro-1-methyl-2-phenyl-1H-imidazol-5-yl)methoxy]-2,3-dihydro-1-benzofuran-3-yl}acetic acid

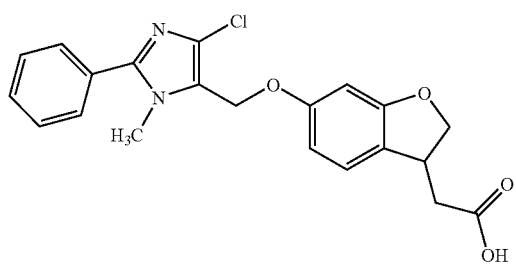

yield 41%. MS (ESI+, m/e) 399 (M+1).

EXAMPLE 136

(6-{[4-(4-chlorophenyl)-5-methyl-1,3-oxazol-2-yl]methoxy}-2,3-dihydro-1-benzofuran-3-yl)acetic acid

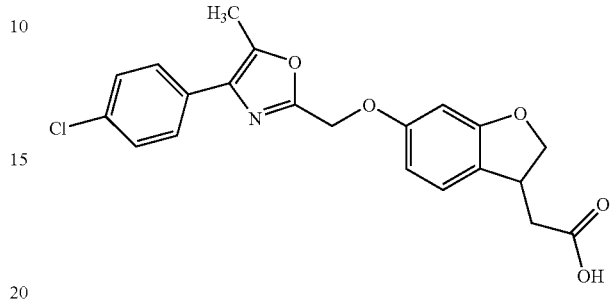

yield 40%. MS (ESI+, m/e) 400 (M+1).

EXAMPLE 137

{6-[2-(2-phenyl-1H-imidazol-4-yl)ethoxy]-2,3-dihydro-1-benzofuran-3-yl}acetic acid

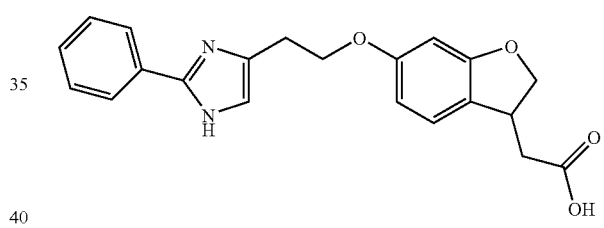

yield 39%. MS (ESI+, m/e) 365 (M+1).

EXAMPLE 138

(6-{[5-(4-chlorophenyl)-1,3-oxazol-4-yl]methoxy}-2,3-dihydro-1-benzofuran-3-yl)acetic acid

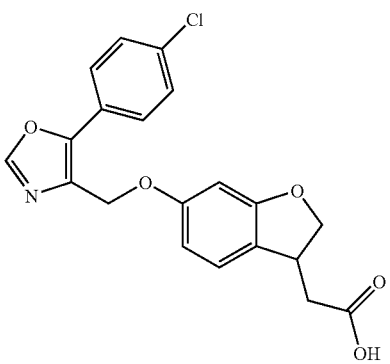

yield 52%. MS (ESI+, m/e) 386 (M+1).

EXAMPLE 139

(6-{[5-(4-fluorophenyl)-1,2,3-thiadiazol-4-yl]methoxy}-2,3-dihydro-1-benzofuran-3-yl)acetic acid

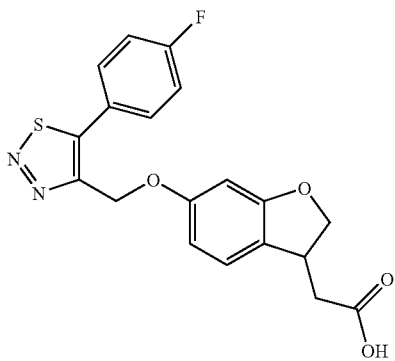

yield 15%. MS (ESI+, m/e) 387 (M+1).

EXAMPLE 140

{6-[(1,5-diphenyl-1H-pyrazol-4-yl)methoxy]-2,3-dihydro-1-benzofuran-3-yl}acetic acid

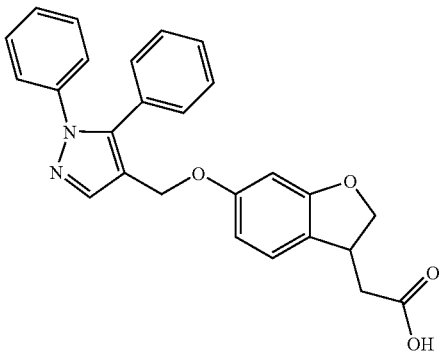

yield 52%. MS (ESI+, m/e) 427 (M+1).

EXAMPLE 141

{6-[3-(1-butyl-1H-indol-3-yl)propoxy]-2,3-dihydro-1-benzofuran-3-yl}acetic acid

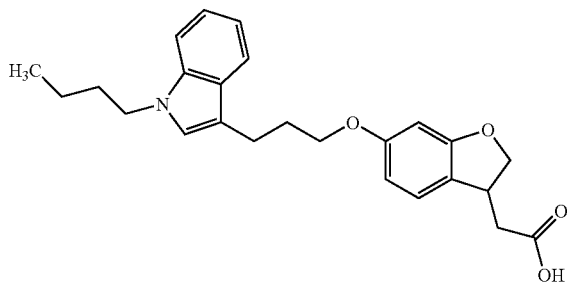

[Step 1]

To a suspension of PS-triphenylphosphine resin (manufactured by Argonout, 2.12 mmol/g) (200 mg, 0.42 mmol) in THF (1.5 mL) was added a solution of methyl (6-hydroxy-2,3-dihydro-1-benzofuran-3-yl)acetate (30 mg, 0.14 mmol) in THF (0.5 mL), and the mixture was shaken at room temperature for 15 min. Di-tert-butyl diazodicarboxylate (60 mg, 0.34 mmol) was added and the mixture was further shaken at room temperature for 20 min. A solution of 3-(1-butyl-1H-indol-3-yl)propan-1-ol (42 mg, 0.18 mmol) in THF (0.5 mL) was added, and the mixture was shaken at room temperature for 18 hr. Dichloromethane (1.5 mL) was added to the reaction mixture, and the insoluble material was filtered off. The filtrate was concentrated under reduced pressure using GeneVac centrifugal evaporator.

[Step 2]

The obtained product was dissolved in methanol (2 mL), and 1 M aqueous sodium hydroxide solution (0.25 mL, 0.25 mmol) was added, and the mixture was stirred at room temperature for 18 hr. The reaction mixture was acidified with 1 M hydrochloric acid and extracted with dichloromethane (2 mL). The organic layer was concentrated under reduced pressure using GeneVac centrifugal evaporator. The residue was purified by preparative HPLC to give the title compound (26.9 mg, yield 47%).

$^1$H NMR (CDCl$_3$) δ: 0.91(3H, t, J=7.4 Hz), 1.25-1.37(2H, m), 1.72-1.82(2H, m), 2.11-2.20(2H, m), 2.62(1H, dd, J=9.5, 16.7 Hz), 2.82(1H, dd, J=5.1, 16.8 Hz), 2.92(2H, t, J=7.4 Hz), 3.76-3.85(1H, m), 3.95(2H, t, J=6.2 Hz), 4.05(2H, t, J=7.4 Hz), 4.28(1H, dd, J=6.0, 9.0 Hz), 4.76(1H, t, J=9.0 Hz), 6.39-6.45(2H, m), 6.88(1H, s), 7.02-7.32(4H, m), 7.59(1H, dd, J=0.9, 7.8 Hz).

EXAMPLE 142

[6-({6-[2-(5-methyl-2-phenyl-1,3-oxazol-4-yl)ethoxy]-3-pyridinyl}methoxy)-2,3-dihydro-1-benzofuran-3-yl]acetic acid

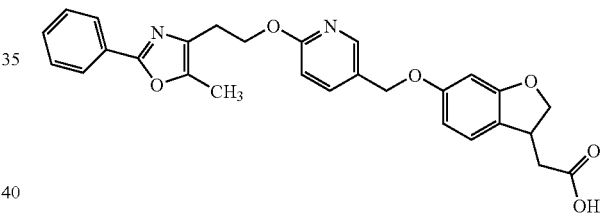

yield 37%. MS (ESI+, m/e) 487 (M+1).

EXAMPLE 143

[6-({2-[(5-methyl-2-phenyl-1,3-oxazol-4-yl)methoxy]benzyl}oxy)-2,3-dihydro-1-benzofuran-3-yl]acetic acid

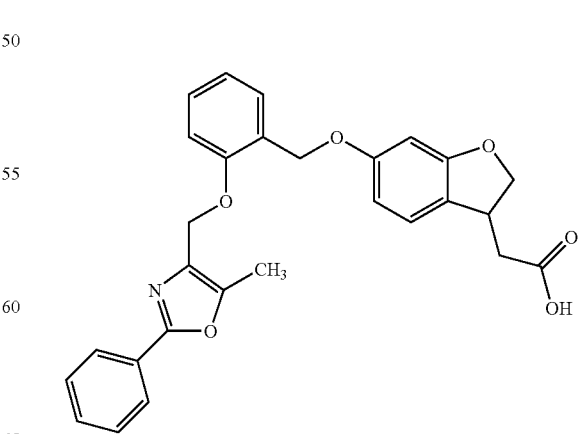

yield 53%. MS (ESI+, m/e) 472 (M+1).

EXAMPLE 144

[6-({4-[(4-phenyl-1,3-thiazol-2-yl)methoxy]benzyl}oxy)-2,3-dihydro-1-benzofuran-3-yl]acetic acid

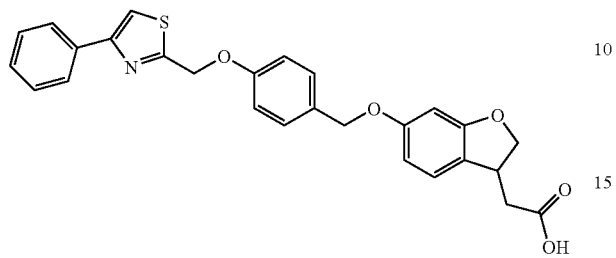

yield 10%. MS (ESI+, m/e) 474 (M+1).

EXAMPLE 145

[6-(3-{4-[(4-phenyl-1,3-thiazol-2-yl)methoxy]phenyl}propoxy)-2,3-dihydro-1-benzofuran-3-yl]acetic acid

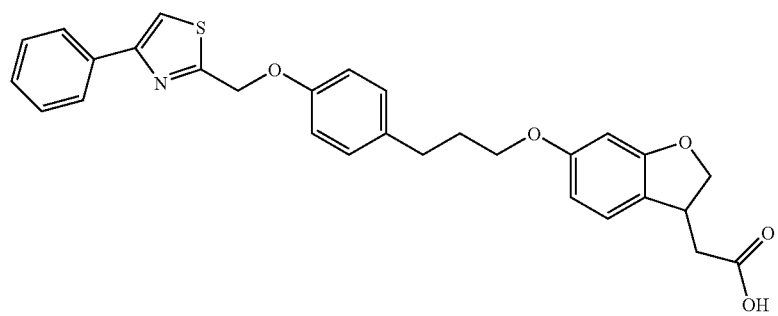

yield 11%. MS (ESI+, m/e) 502 (M+1).

EXAMPLE 146

[6-({4-[4-(trifluoromethyl)phenyl]-1,3-thiazol-2-yl}methoxy)-2,3-dihydro-1-benzofuran-3-yl]acetic acid

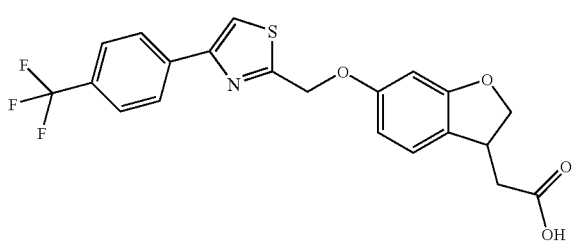

yield 18%. MS (ESI+, m/e) 436 (M+1).

EXAMPLE 147

(6-{[(2S)-2-(dibenzylamino)-3-phenylpropyl]oxy}-2,3-dihydro-1-benzofuran-3-yl)acetic acid trifluoroacetate

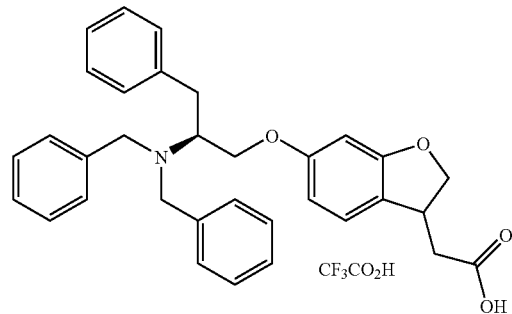

yield 14%. MS (ESI+, m/e) 508 (M+1).

EXAMPLE 148

{6-[3-(dibenzylamino)propoxy]-2,3-dihydro-1-benzofuran-3-yl}acetic acid trifluoroacetate

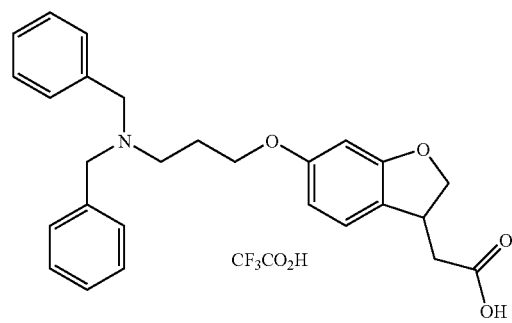

yield 66%. MS (ESI+, m/e) 432 (M+1).

EXAMPLE 149

[6-(3,3-diphenylpropoxy)-2,3-dihydro-1-benzofuran-3-yl]acetic acid

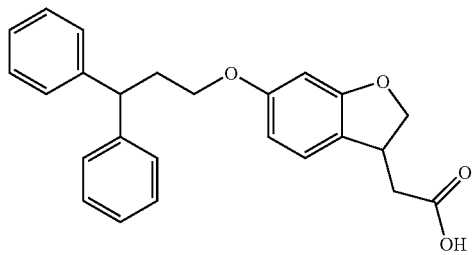

yield 46%. MS (ESI+, m/e) 389 (M+1).

EXAMPLE 150

{6-[2-(dibenzylamino)ethoxy]-2,3-dihydro-1-benzofuran-3-yl}acetic acid trifluoroacetate

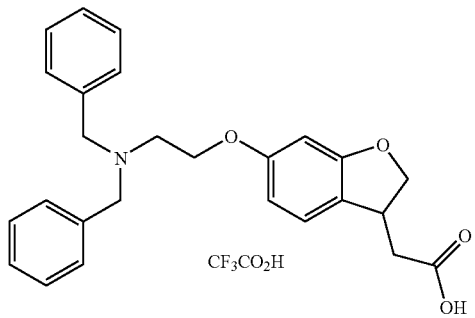

yield 58%. MS (ESI+, m/e) 432 (M+1).

EXAMPLE 151

(6-{[(1R,2S)-2-(benzylamino)cyclohexyl]methoxy}-2,3-dihydro-1-benzofuran-3-yl)acetic acid trifluoroacetate

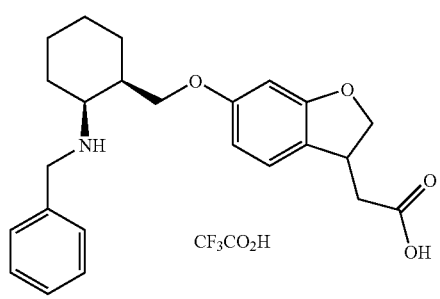

yield 12%. MS (ESI+, m/e) 396 (M+1).

EXAMPLE 152

{6-[2-(5-methyl-2-phenyl-1,3-oxazol-4-yl)ethoxy]-2,3-dihydro-1-benzofuran-3-yl}acetic acid

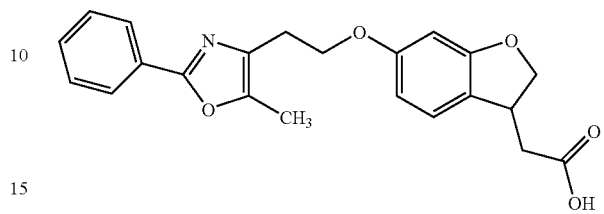

yield 70%. MS (ESI+, m/e) 380 (M+1).

EXAMPLE 153

{(2R)-6-[(5-methyl-2-phenyl-1,3-oxazol-4-yl)methoxy]-1,2,3,4-tetrahydronaphthalen-2-yl}acetic acid

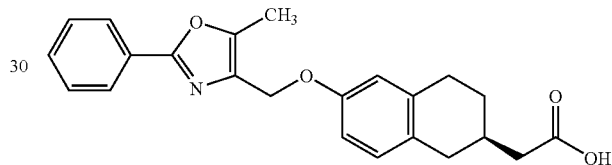

In the same manner as in Examples 81 and 6, the title compound was obtained as colorless needle crystals from methyl [(2R)-6-hydroxy-1,2,3,4-tetrahydronaphthalen-2-yl]acetate and 4-(chloromethyl)-5-methyl-2-phenyl-1,3-oxazole. yield 62% (recrystallized from hexane-ethyl acetate). MS m/z 378 (MH⁺).

EXAMPLE 154

[(2R)-6-({3-methyl-1-[5-(trifluoromethyl)pyridin-2-yl]-1H-pyrazol-4-yl}methoxy)-1,2,3,4-tetrahydronaphthalen-2-yl]acetic acid

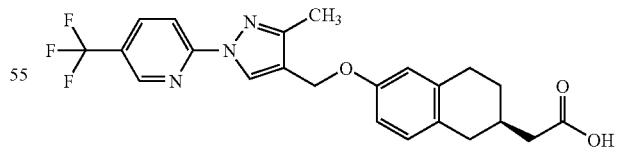

In the same manner as in Examples 8 and 6, the title compound was obtained as colorless needle crystals from methyl [(2R)-6-hydroxy-1,2,3,4-tetrahydronaphthalen-2-yl]acetate and {3-methyl-1-[5-(trifluoromethyl)pyridin-2-yl]-1H-pyrazol-4-yl}methanol. yield 53% (recrystallized from hexane-ethyl acetate).
MS m/z 446 (MH⁺)

EXAMPLE 155

((2R)-6-{[4-(cyclopropylmethoxy)benzyl]oxy}-1,2,3,4-tetrahydronaphthalen-2-yl)acetic acid

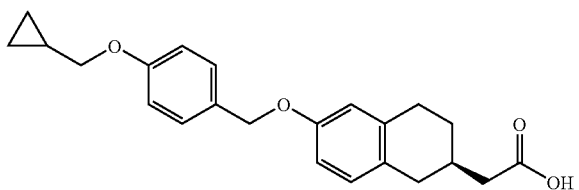

In the same manner as in Examples 8 and 6, the title compound was obtained as colorless needle crystals from methyl [(2R)-6-hydroxy-1,2,3,4-tetrahydronaphthalen-2-yl]acetate and [4-(cyclopropylmethoxy)phenyl]methanol. yield 48% (recrystallized from hexane-ethyl acetate).

$^1$H NMR (CDCl$_3$) δ: 0.32-0.37(2H, m), 0.61-0.68(2H, m), 1.21-1.34(1H, m), 1.42-1.55(1H, m), 1.94-2.03(1H, m), 2.21-2.33(1H, m), 2.41-2.50(3H, m), 2.79-2.91(3H, m), 3.80(2H, d, J=7.0 Hz), 4.94(2H, s), 6.69(1H, d, J=2.5 Hz), 6.74(1H, dd, J=8.3, 2.5 Hz), 6.90(2H, d, J=8.7 Hz), 6.96(1H, d, J=8.3 Hz), 7.33(2H, d, J=8.7 Hz).

FORMULATION EXAMPLE 1

Production of Capsule

| | |
|---|---|
| 1) compound of Example 1 | 30 mg |
| 2) microcrystalline cellulose | 10 mg |
| 3) lactose | 19 mg |
| 4) magnesium stearate | 1 mg |
| total | 60 mg |

The above-mentioned 1), 2), 3) and 4) are mixed and filled in a gelatin capsule.

FORMULATION EXAMPLE 2

Production of Tablet

| | |
|---|---|
| 1) compound of Example 1 | 30 g |
| 2) lactose | 50 g |
| 3) corn starch | 15 g |
| 4) carboxymethylcellulose calcium | 44 g |
| 5) magnesium stearate | 1 g |
| 1000 tablets total | 140 g |

The total amount of the above-mentioned 1), 2) and 3) and 30 g of 4) are kneaded with water, vacuum dried and granulated. The granulated powder is mixed with 14 g of 4) and 1 g of 5) and tableted with a tableting machine. In this way, 1000 tablets containing 30 mg of the compound of Example 1 per tablet are obtained.

EXPERIMENTAL EXAMPLE 1

Determination of EC$_{50}$ of the Compound of Example on Human GPR40

For determination of EC$_{50}$, CHO cell line that stably expressed human GPR40 was used. Unless otherwise indicated, the CHO cell line was cultured using α-MEM medium (Invitrogen) containing 10% fetal calf serum (Invitrogen).

The cells cultured to nearly confluent were rinsed with PBS (Invitrogen) on the previous day of the assay, peeled off with 0.05% Trypsin•EDTA solution (Invitrogen) and recovered by centrifugation. The number of the obtained cells was counted, and the cells were diluted such that 3×10$^5$ cells were contained per 1 mL of the medium, dispensed to a Black welled 96-well plate (coster) by 100 μL per well and cultured overnight in a CO$_2$ incubator. Various test samples were added to the CHO cells thus prepared, and the changes in the intracellular calcium concentration were measured using FLIPR (Molecular Device). The below-mentioned pre-treatment was applied to measure changes in the intracellular calcium concentration by FLIPR.

An assay buffer for adding a fluorescence dye Fluo3-AM (DOJIN) to the cells, or for washing the cells immediately before FLIPR assay was prepared. To a solution of 1M HEPES (pH 7.4, DOJIN, 20 mL) added to HBSS (Invitrogen, 1000 mL) (hereinafter HBSS/HEPES solution) was added a solution (10 mL) obtained by dissolving probenecid (Sigma, 710 mg) in 1N NaOH (5 mL), and adding and mixing an HBSS/HEPES solution (5 mL), and the resulting solution was used as an assay buffer. Fluo3-AM (50 μg) was dissolved in dimethyl sulfoxide (Wako, 21 μL), and an equivalent amount of 20% pluronic acid (Molecular Probes) was added and mixed. The solution was added to the assay buffer (10.6 mL) supplemented with fetal calf serum (105 μL) to give a fluorescence dye solution. On the previous day of assay, the medium of the CHO cells newly inoculated to the Black welled 96-well plate was removed, the fluorescence dye solution was immediately dispensed by 100 μL per well and the cells were cultured in a CO$_2$ incubator for 1 hr to allow intake of the fluorescence dye by the cells. The cells after the culture were washed with the above-mentioned assay buffer and set on FLIPR. The test sample was diluted with DMSO in advance, dispensed to polypropylene 96-well plate (sample plate) by 2 μL, and cryopreserved at −20° C. To the thawed sample plate was added an assay buffer containing 0.015% CHAPS (DOJIN) by 198 μL, and simultaneously set on FLIPR together with the cell plate. After the aforementioned pre-treatment, changes in the intracellular calcium concentration upon addition of various test samples were measured by FLIPR. Based on the results, a dose-response curve of each compound of Examples was formed and EC$_{50}$ was calculated. The results are shown in Table 1.

TABLE 1

| Receptor Function Modulating Action on GPR40 | |
|---|---|
| compound No. | EC$_{50}$ (nM) |
| Example 6 | <100 |
| Example 11 | <100 |

TABLE 1-continued

| Receptor Function Modulating Action on GPR40 | |
|---|---|
| compound No. | $EC_{50}$ (nM) |
| Example 13 | <100 |
| Example 15 | <100 |
| Example 17 | <100 |
| Example 19 | <1000 |
| Example 21 | <1000 |
| Example 25 | <1000 |
| Example 33 | <100 |
| Example 35 | <100 |
| Example 47 | <100 |
| Example 58 | <100 |
| Example 66 | <100 |
| Example 70 | <100 |
| Example 72 | <100 |
| Example 73 | <1000 |
| Example 75 | <100 |
| Example 78 | <100 |
| Example 125 | <1000 |

INDUSTRIAL APPLICABILITY

The compound of the present invention has a superior GPR40 receptor function modulating action and can be used as an agent for the prophylaxis or treatment of diabetes and the like.

This application is based on patent application Nos. 153986/2003 and 139144/2004 filed in Japan, the content of which is hereby incorporated by reference.

The invention claimed is:
1. A compound represented by the formula:

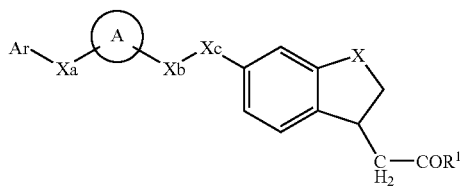

wherein Ar is cyclopropyl, cyclohexyl, phenyl, naphthyl, thienyl, furyl, thiazolyl, oxazolyl, imidazolyl, pyrazolyl, triazolyl, pyridyl, pyrazinyl, benzo[b]thienyl, indolyl or indanyl, each of which optionally is substituted by 1 to 5 substituent(s) selected from the group consisting of
(1) halogen atom;
(2) hydroxy group;
(3) amino group;
(4) nitro group;
(5) cyano group;
(6) optionally substituted $C_{1-6}$ alkyl group;
(7) optionally substituted $C_{2-6}$ alkenyl group;
(8) optionally substituted $C_{2-6}$ alkynyl group;
(9) $C_{6-14}$ aryl group optionally substituted by 1 to 3 substituent(s) selected from the group consisting of halogen atom, hydroxy group, amino group, nitro group, cyano group, optionally halogenated $C_{1-6}$ alkyl group, mono- or di-$C_{1-6}$ alkyl-amino group, $C_{6-14}$ aryl group, mono- or di-$C_{6-14}$ aryl-amino group, $C_{3-8}$ cycloalkyl group, $C_{1-6}$ alkoxy group, $C_{1-6}$ alkoxy-$C_{1-6}$ alkoxy group, $C_{1-6}$ alkylthio group, $C_{1-6}$ alkylsulfinyl group, $C_{1-6}$ alkylsulfonyl group, optionally esterified carboxyl group, carbamoyl group, thiocarbamoyl group, mono- or di-$C_{1-6}$ alkyl-carbamoyl group, mono- or di-$C_{6-14}$ aryl-carbamoyl group, sulfamoyl group, mono- or di-$C_{1-6}$ alkyl-sulfamoyl group and mono- or di-$C_{6-14}$ aryl-sulfamoyl group;
(10) $C_{6-14}$ aryloxy group optionally substituted by 1 to 3 substituent(s) selected from the group consisting of halogen atom, hydroxy group, amino group, nitro group, cyano group, optionally halogenated $C_{1-6}$ alkyl group, mono- or di-$C_{1-6}$ alkyl-amino group, $C_{6-14}$ aryl group, mono- or di-$C_{6-14}$ aryl-amino group, $C_{3-8}$ cycloalkyl group, $C_{1-6}$ alkoxy group, $C_{1-6}$ alkoxy-$C_{1-6}$ alkoxy group, $C_{1-6}$ alkylthio group, $C_{1-6}$ alkylsulfinyl group, $C_{1-6}$ alkylsulfonyl group, optionally esterified carboxyl group, carbamoyl group, thiocarbamoyl group, mono- or di-$C_{1-6}$ alkyl-carbamoyl group, mono- or di-$C_{6-14}$ aryl-carbamoyl group, sulfamoyl group, mono- or di-$C_{1-6}$ alkyl-sulfamoyl group and mono- or di-$C_{6-14}$ aryl-sulfamoyl group;
(11) $C_{7-16}$ aralkyloxy group optionally substituted by 1 to 3 substituent(s) selected from the group consisting of halogen atom, hydroxy group, amino group, nitro group, cyano group, optionally halogenated $C_{1-6}$ alkyl group, mono- or di-$C_{1-6}$ alkyl-amino group, $C_{6-14}$ aryl group, mono- or di-$C_{6-14}$ aryl-amino group, $C_{3-8}$ cycloalkyl group, $C_{1-6}$ alkoxy group, $C_{1-6}$ alkoxy-$C_{1-6}$ alkoxy group, $C_{1-6}$ alkylthio group, $C_{1-6}$ alkylsulfinyl group, $C_{1-6}$ alkylsulfonyl group, optionally esterified carboxyl group, carbamoyl group, thiocarbamoyl group, mono- or di-$C_{1-6}$ alkyl-carbamoyl group, mono- or di-$C_{6-14}$ aryl-carbamoyl group, sulfamoyl group, mono- or di-$C_{1-6}$ alkyl-sulfamoyl group and mono- or di-$C_{6-14}$ aryl-sulfamoyl group;
(12) heterocyclic group optionally substituted by 1 to 3 substituent(s) selected from the group consisting of halogen atom, hydroxy group, amino group, nitro group, cyano group, optionally halogenated $C_{1-6}$ alkyl group, mono- or di-$C_{1-6}$ alkyl-amino group, $C_{6-14}$ aryl group, mono- or di-$C_{6-14}$ aryl-amino group, $C_{3-8}$ cycloalkyl group, $C_{1-6}$ alkoxy group, $C_{1-6}$ alkoxy-$C_{1-6}$ alkoxy group, $C_{1-6}$ alkylthio group, $C_{1-6}$ alkylsulfinyl group, $C_{1-6}$ alkylsulfonyl group, optionally esterified carboxyl group, carbamoyl group, thiocarbamoyl group, mono- or di-$C_{1-6}$ alkyl-carbamoyl group, mono- or di-$C_{6-14}$ aryl-carbamoyl group, sulfamoyl group, mono- or di-$C_{1-6}$ alkyl-sulfamoyl group and mono- or di-$C_{6-14}$ aryl-sulfamoyl group;
(13) mono- or di-$C_{1-6}$ alkyl-amino group;
(14) mono- or di-$C_{6-14}$ aryl-amino group;
(15) mono- or di-$C_{7-16}$ aralkyl-amino group;
(16) N—$C_{1-6}$ alkyl-N-$C_{6-14}$ aryl-amino group;
(17) N—$C_{1-6}$ alkyl-N-$C_{7-16}$ aralkyl-amino group;
(18) $C_{3-8}$ cycloalkyl group;
(19) optionally substituted $C_{1-6}$ alkoxy group;
(20) $C_{1-6}$ alkylthio group;
(21) $C_{1-6}$ alkylsulfinyl group;
(22) $C_{1-6}$ alkylsulfonyl group;
(23) optionally esterified carboxyl group;
(24) $C_{1-6}$ alkyl-carbonyl group;
(25) $C_{3-8}$ cycloalkyl-carbonyl group;
(26) $C_{6-14}$ aryl-carbonyl group;
(27) carbamoyl group;
(28) thiocarbamoyl group;
(29) mono- or di-$C_{1-6}$ alkyl-carbamoyl group;
(30) mono- or di-$C_{6-14}$ aryl-carbamoyl group;
(31) mono- or di-5- to 7-membered heterocyclyl-carbamoyl group;
(32) sulfamoyl group;

(33) mono- or di-$C_{1-6}$ alkyl-sulfamoyl group; and
(34) mono- or di-$C_{6-14}$ aryl-sulfamoyl group;
ring A is benzene,
Xa is a bond,
Xb is $(CH_2)_n$ wherein n is 1 or 2,
Xc is O,
X=—O—, —$CH_2$—, —$CH_2CH_2$—, or —$CH_2CH_2CH_2$—, and
$R^1$ is a hydroxy group or $C_{1-10}$ alkoxy group,
or a salt thereof.

2. The compound of claim 1, wherein the cyclic group represented by Ar is a phenyl group which optionally is substituted by said 1 to 5 substituent(s).

3. The compound of claim 1, wherein Xb is —$CH_2$—.

4. The compound of claim 1, wherein $R^1$ is a hydroxy group.

5. The compound of claim 1, which is represented by the formula:

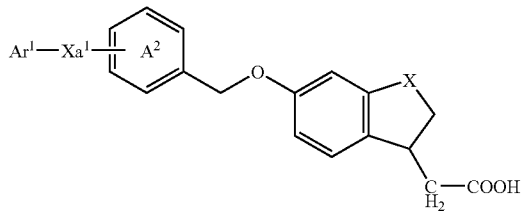

wherein $Ar^1$ is phenyl group or indanyl group, each of which optionally is substituted by said 1 to 5 substituent(s),
$Xa^1$ is a bond, and
ring $A^2$ is benzene.

6. The compound of claim 1, which is represented by the formula:

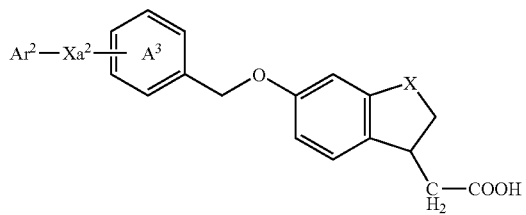

wherein $Ar^2$ is thiazolyl group which optionally is substituted by said 1 to 5 substituent(s),
$Xa^2$ is a bond, and
ring $A^3$ is benzene.

7. A pharmaceutical composition comprising the compound of claim 1 with a pharmacologically acceptable carrier.

* * * * *